US011109761B2

(12) United States Patent
Islam

(10) Patent No.: US 11,109,761 B2
(45) Date of Patent: *Sep. 7, 2021

(54) HIGH SIGNAL-TO-NOISE RATIO LIGHT SPECTROSCOPY OF TISSUE

(71) Applicant: OMNI MEDSCI, INC., Ann Arbor, MI (US)

(72) Inventor: Mohammed N. Islam, Ann Arbor, MI (US)

(73) Assignee: OMNI MEDSCI, INC., Ann Arbor, MI (US)

( * ) Notice: Subject to any disclaimer, the term of this patent is extended or adjusted under 35 U.S.C. 154(b) by 513 days.

This patent is subject to a terminal disclaimer.

(21) Appl. No.: 16/004,359

(22) Filed: Jun. 9, 2018

(65) Prior Publication Data
US 2018/0289264 A1  Oct. 11, 2018

Related U.S. Application Data

(63) Continuation of application No. 14/109,007, filed on Dec. 17, 2013, now Pat. No. 9,993,159.
(Continued)

(51) Int. Cl.
*A61B 5/00* (2006.01)

(52) U.S. Cl.
CPC .......... *A61B 5/0075* (2013.01); *A61B 5/0091* (2013.01); *A61B 2562/0238* (2013.01)

(58) Field of Classification Search
CPC ................ A61B 5/0075; A61B 5/0091; A61B 2562/0238
See application file for complete search history.

(56) References Cited

U.S. PATENT DOCUMENTS 4,063,106 A  12/1977  Ashkin et al.
4,158,750 A  6/1979  Sakoe et al.
(Continued)

FOREIGN PATENT DOCUMENTS

EP  1148666  10/2001
WO  WO09715240  5/1997
(Continued)

OTHER PUBLICATIONS

Wang, Multiscale photoacoustic microscopy and computer tomography, Sep. 2009, Nature Photonics, vol. 2. (Year: 2009).*
(Continued)

*Primary Examiner* — Christopher Koharski
*Assistant Examiner* — Katherine M McDonald
(74) *Attorney, Agent, or Firm* — Brooks Kushman P.C.

(57) ABSTRACT

A diagnostic system includes a light source having semiconductor sources, optical amplifiers, and fibers configured to deliver a first optical beam to a nonlinear element configured to broaden a spectrum of the first optical beam to at least 10 nanometers through a nonlinear effect in the nonlinear element, wherein a broadened-spectrum output beam comprises a near-infrared wavelength between 600-1000 nanometers. An interface device, having a cap with fiber leads configured to couple to the light source and to a receiver having one or more detectors, delivers the output optical beam to a tissue sample. The receiver is configured to receive a diffuse spectroscopy output beam resulting from light diffusion of the output optical beam into a top two (2) millimeters of the sample and to process the diffuse spectroscopy output beam to generate an output signal that monitors absorption or scattering features of the tissue sample.

20 Claims, 26 Drawing Sheets

Related U.S. Application Data

(60) Provisional application No. 61/747,553, filed on Dec. 31, 2012.

(56) References Cited

U.S. PATENT DOCUMENTS

| | | |
|---|---|---|
| 4,221,997 A | 9/1980 | Flemming |
| 4,275,266 A | 6/1981 | Lasar |
| 4,374,618 A | 2/1983 | Howard |
| 4,403,605 A | 9/1983 | Tanikawa |
| 4,462,080 A | 7/1984 | Johnstone et al. |
| 4,516,207 A | 5/1985 | Moriyama et al. |
| 4,523,884 A | 6/1985 | Clement et al. |
| 4,605,080 A | 8/1986 | Lemelson |
| 4,641,292 A | 2/1987 | Tunnell et al. |
| 4,704,696 A | 11/1987 | Reimer et al. |
| 4,728,974 A | 3/1988 | Nio et al. |
| 4,762,455 A | 8/1988 | Coughlan et al. |
| 4,776,016 A | 10/1988 | Hansen |
| 4,958,910 A | 9/1990 | Taylor et al. |
| 4,989,253 A | 1/1991 | Liang et al. |
| 5,078,140 A | 1/1992 | Kwoh |
| 5,084,880 A | 1/1992 | Esterowitz et al. |
| 5,086,401 A | 2/1992 | Glassman et al. |
| 5,134,620 A | 7/1992 | Huber |
| 5,142,930 A | 9/1992 | Allen et al. |
| 5,180,378 A | 1/1993 | Kung et al. |
| 5,191,628 A | 3/1993 | Byron |
| 5,218,655 A | 6/1993 | Mizrahi |
| 5,230,023 A | 7/1993 | Nakano |
| 5,267,256 A | 11/1993 | Saruwatari et al. |
| 5,267,323 A | 11/1993 | Kimura |
| 5,300,097 A | 4/1994 | Lemer et al. |
| 5,303,148 A | 4/1994 | Mattson et al. |
| 5,305,427 A | 4/1994 | Nagata |
| 5,313,306 A | 5/1994 | Kuban et al. |
| 5,323,404 A | 6/1994 | Grubb |
| 5,345,538 A | 9/1994 | Narayannan et al. |
| 5,400,165 A | 3/1995 | Gnauck et al. |
| 5,408,409 A | 4/1995 | Glassman et al. |
| 5,458,122 A | 10/1995 | Hethuin |
| 5,497,769 A | 3/1996 | Gratton et al. |
| 5,544,654 A | 8/1996 | Murphy et al. |
| 5,572,999 A | 11/1996 | Funda et al. |
| 5,617,871 A | 4/1997 | Burrows |
| 5,631,758 A | 5/1997 | Knox et al. |
| 5,687,734 A | 11/1997 | Dempsey et al. |
| 5,695,493 A | 12/1997 | Nakajima et al. |
| 5,696,778 A | 12/1997 | MacPherson |
| 5,704,351 A | 1/1998 | Mortara et al. |
| 5,718,234 A | 2/1998 | Warden et al. |
| 5,747,806 A | 5/1998 | Khalil |
| 5,748,103 A | 5/1998 | Flach et al. |
| 5,792,204 A | 8/1998 | Snell |
| 5,812,978 A | 9/1998 | Nolan |
| 5,855,550 A | 1/1999 | Lai et al. |
| 5,862,803 A | 1/1999 | Besson et al. |
| 5,867,305 A | 2/1999 | Waarts et al. |
| 5,912,749 A | 6/1999 | Harstead et al. |
| 5,944,659 A | 8/1999 | Flach et al. |
| 5,950,629 A | 9/1999 | Taylor et al. |
| 5,957,854 A | 9/1999 | Besson et al. |
| 5,970,457 A | 10/1999 | Brant et al. |
| 6,014,249 A | 1/2000 | Fermann et al. |
| 6,043,927 A | 3/2000 | Islam |
| 6,078,833 A | 6/2000 | Hueber |
| 6,115,673 A | 9/2000 | Malin |
| 6,185,535 B1 | 2/2001 | Hedin et al. |
| 6,200,309 B1 | 3/2001 | Rice et al. |
| 6,224,542 B1 | 5/2001 | Chang et al. |
| 6,246,707 B1 | 6/2001 | Yin et al. |
| 6,246,896 B1 | 6/2001 | Dumoulin |
| 6,273,858 B1 | 8/2001 | Fox et al. |
| 6,278,975 B1 | 8/2001 | Brant et al. |
| 6,281,471 B1 | 8/2001 | Smart |
| 6,285,897 B1 | 9/2001 | Kilcoyne |
| 6,289,238 B1 | 9/2001 | Besson et al. |
| 6,301,271 B1 | 10/2001 | Sanders et al. |
| 6,301,273 B1 | 10/2001 | Sanders et al. |
| 6,333,803 B1 | 12/2001 | Kurotori et al. |
| 6,337,462 B1 | 1/2002 | Smart |
| 6,340,806 B1 | 1/2002 | Smart et al. |
| 6,350,261 B1 | 2/2002 | Domankevitz et al. |
| 6,364,834 B1 | 4/2002 | Reuss et al. |
| 6,374,006 B1 | 4/2002 | Islam et al. |
| 6,381,391 B1 | 4/2002 | Islam et al. |
| 6,402,691 B1 | 6/2002 | Peddicord et al. |
| 6,407,853 B1 | 6/2002 | Samson et al. |
| 6,436,107 B1 | 8/2002 | Wang et al. |
| 6,441,747 B1 | 8/2002 | Khair et al. |
| 6,442,430 B1 | 8/2002 | Ferek-Petric |
| 6,443,890 B1 | 9/2002 | Schulze et al. |
| 6,450,172 B1 | 9/2002 | Hartlaub et al. |
| 6,453,201 B1 | 9/2002 | Daum et al. |
| 6,454,705 B1 | 9/2002 | Cosentino et al. |
| 6,458,120 B1 | 10/2002 | Shen et al. |
| 6,462,500 B1 | 10/2002 | L'Hegarat et al. |
| 6,463,361 B1 | 10/2002 | Wang et al. |
| 6,480,656 B1 | 11/2002 | Islam et al. |
| 6,512,936 B1 | 1/2003 | Monfre |
| 6,534,012 B1 | 3/2003 | Hazen et al. |
| 6,549,702 B2 | 4/2003 | Islam et al. |
| 6,567,431 B2 | 5/2003 | Tabirian et al. |
| 6,587,702 B1 | 7/2003 | Ruchti |
| 6,603,910 B2 | 8/2003 | Islam et al. |
| 6,605,080 B1 | 8/2003 | Altshuler et al. |
| 6,611,643 B2 | 8/2003 | Birk |
| 6,625,180 B2 | 9/2003 | Bufetov et al. |
| 6,631,025 B2 | 10/2003 | Islam et al. |
| 6,640,117 B2 | 10/2003 | Makarewicz |
| 6,659,947 B1 | 12/2003 | Carter et al. |
| 6,659,999 B1 | 12/2003 | Anderson et al. |
| 6,738,652 B2 | 5/2004 | Mattu |
| 6,760,148 B2 | 7/2004 | Islam |
| 6,773,922 B2 | 8/2004 | Jeng |
| 6,788,965 B2 | 9/2004 | Ruchti |
| 6,802,811 B1 | 10/2004 | Slepian |
| 6,816,241 B2 | 11/2004 | Grubisic |
| 6,847,336 B1 | 1/2005 | Lemelson |
| 6,864,978 B1 | 3/2005 | Hazen |
| 6,885,498 B2 | 4/2005 | Islam |
| 6,885,683 B1 | 4/2005 | Fermann et al. |
| 6,943,936 B2 | 9/2005 | Islam et al. |
| 6,990,364 B2 | 1/2006 | Ruchti |
| 7,010,336 B2 | 3/2006 | Lorenz |
| 7,027,467 B2 | 4/2006 | Baev et al. |
| 7,060,061 B2 | 6/2006 | Altshuler et al. |
| 7,133,710 B2 | 11/2006 | Acosta |
| 7,167,300 B2 | 1/2007 | Fermann et al. |
| 7,209,657 B1 | 4/2007 | Islam |
| 7,233,816 B2 | 6/2007 | Blank |
| 7,259,906 B1 | 8/2007 | Islam |
| 7,263,288 B1 | 8/2007 | Islam |
| 7,294,105 B1 | 11/2007 | Islam |
| 7,299,080 B2 | 11/2007 | Acosta |
| 7,317,938 B2 | 1/2008 | Lorenz |
| 7,395,158 B2 | 7/2008 | Monfre |
| 7,433,116 B2 | 10/2008 | Islam |
| 7,519,253 B2 | 4/2009 | Islam |
| 7,519,406 B2 | 4/2009 | Blank |
| 7,620,674 B2 | 11/2009 | Ruchti |
| 7,697,966 B2 | 4/2010 | Monfre |
| 7,787,503 B2 | 8/2010 | Wadsworth |
| 7,787,924 B2 | 8/2010 | Acosta |
| 7,800,818 B2 | 9/2010 | Mattsson |
| 7,807,718 B2 | 10/2010 | Hashim |
| 8,000,574 B2 | 8/2011 | Buchter |
| 8,108,036 B2 | 1/2012 | Tran |
| 8,145,286 B2 | 3/2012 | Arai |
| 8,472,108 B2 | 6/2013 | Islam |
| 8,649,838 B2 | 2/2014 | Chen et al. |
| 8,725,226 B2 | 5/2014 | Isaacson |
| 10,188,299 B2 | 1/2019 | Islam |
| 10,213,113 B2 | 2/2019 | Islam |
| 10,517,484 B2 | 12/2019 | Islam |

(56) References Cited

U.S. PATENT DOCUMENTS

| | | |
|---|---|---|
| 2002/0013518 A1 | 1/2002 | West et al. |
| 2002/0019584 A1 | 2/2002 | Schulze et al. |
| 2002/0032468 A1 | 3/2002 | Hill et al. |
| 2002/0082612 A1 | 6/2002 | Moll et al. |
| 2002/0109621 A1 | 8/2002 | Khair et al. |
| 2002/0115914 A1 | 8/2002 | Russ |
| 2002/0128846 A1 | 9/2002 | Miller |
| 2002/0178003 A1 | 11/2002 | Gehrke et al. |
| 2003/0022126 A1 | 1/2003 | Buchalla |
| 2004/0174914 A1 | 9/2004 | Fukatsu |
| 2004/0240037 A1 | 12/2004 | Harter |
| 2005/0111500 A1 | 5/2005 | Harter et al. |
| 2006/0223032 A1 | 10/2006 | Fried |
| 2006/0245461 A1 | 11/2006 | Islam |
| 2006/0268393 A1 | 11/2006 | Islam |
| 2007/0078348 A1 | 4/2007 | Holman |
| 2008/0105665 A1 | 5/2008 | Kondo |
| 2009/0028193 A1 | 1/2009 | Islam |
| 2009/0156932 A1 | 6/2009 | Zharov |
| 2009/0204110 A1 | 8/2009 | Islam |
| 2010/0046067 A1 | 2/2010 | Fermann et al. |
| 2010/0322490 A1 | 12/2010 | Pan |
| 2010/0331637 A1 | 12/2010 | Ting |
| 2011/0143364 A1 | 6/2011 | Kim |
| 2012/0013722 A1 | 1/2012 | Wong |
| 2013/0274569 A1 | 10/2013 | Islam |

FOREIGN PATENT DOCUMENTS

| | | |
|---|---|---|
| WO | WO97049340 | 12/1997 |
| WO | WO01150959 | 7/2001 |
| WO | 200189362 | 11/2001 |
| WO | 200227640 | 4/2002 |
| WO | 200228123 | 4/2002 |

OTHER PUBLICATIONS

Inter Partes Review No. IPR2020-00175; Petition for Inter Partes Review of U.S. Pat. No. 10,188,299; *Apple Inc. v. Omni Medsci, Inc.;* pp. 1-91; dated Dec. 11, 2019.

Inter Partes Review No. IPR2020-00209; Petition for Inter Partes Review of U.S. Pat. No. 10,213,113; *Apple Inc. v. Omni Medsci, Inc.;* pp. 1-91; dated Dec. 11, 2019.

File History for U.S. Pat. No. 10,213,113 dated Feb. 26, 2019, 686 pps.

Declaration of Brian W. Anthony, PhD, regarding U.S. Pat. No. 10,213,113 in IPR2020-00209, Dec. 11, 2019, 101 pps.

United States District Court Eastern District of Texas Marshall Division; *Omni Medsci, Inc.* vs. *Apple Inc.;* Civil Action No. 2:18-cv-00429; Second Amended Complaint; Feb. 26, 2019; 274 pps.

United States District Court Northern District of California Oakland Division;*Omni Medsci, Inc.* vs. *Apple Inc.;* Civil Action No. 19-cv-05673-YGR; Order staying the case; Nov. 20, 2019, 5 pps.

File History for U.S. Pat. No. 10,188,299 dated Jan. 29, 2019, 787 pps.

Declaration of Brian W. Anthony, PhD, regarding U.S. Pat. No. 10,188,299 in IPR2020-00175, Dec. 11, 2019, 119 pps.

United States District Court Eastern District of Texas Marshall Division; *Omni Medsci, Inc.* vs. *Apple Inc.;* Civil Action No. 2:18-cv-429; Amended Complaint; Jan. 28, 2019; 169 pps.

Roggan, A., M. Friebel, K. Doschel, A. Hahn, G. Muller, "Optical properties of circulating human blood in the wavelength range 400-2500nm," Journal of Biomedical Optics, vol. 4, No. 1, pp. 36-46, (Jan. 1999).

Taroni, P., "Diffuse optical imaging and spectroscopy of the breast: a brief outline of history and perspectives," Photochemical Photobiological Science, vol. 11, pp. 241-250 (2012).

Herranz, M., A. Ruibal, "Optical imaging in breast cancer diagnosis: the next evolution," Journal of Oncology, vol. 2012, article ID 863747, 10 pages, (2012).

Walsh, M.J., R.K. Reddy, R. Bhargava, "Label-free biomedical imaging with mid-IR spectroscopy," IEEE Journal of Selected Topics in Quantum Electronics, article identifier 10.1109/JSTQE.2011.2182635, 12 pages, (2011).

Evers, D.J., B.H.W. Hendriks, G.W. Lucassen, T.J.M. Ruers, "Optical spectroscopy: current advances and future applications in cancer diagnosis and therapy," Future Oncology, vol. 8, No. 3, pp. 307-320 (2012).

Evers, D.J., R. Nachabe, H.M. Klomp, J.W. van Sandick, M.W. Wouters, G.W. Lucassen, B.H.W. Hendriks, J. Wesseling, T.J.M. Ruers, "Diffuse reflectance spectroscopy: a new guidance tool for improvement of biopsy procedures in lung malignancies," Clinical Lung Cancer, article identifier 10.1016/j.clc.2012.02.001, 8 pages, (2012).

Bellisola, G. C. Sorio, "Infrared spectroscopy and microscopy in cancer research and diagnosis," American Journal of Cancer Research, vol. 2, No. 1, pp. 1-21 (2012).

Noreen, R., C.C. Chien, M. Delugin, S. Yao, R. Pineau, Y. Hwu, M. Moenner, C. Petibois, "Detection of collagens in brain tumors based on FTIR imaging and chemometrics," Annals of Bioanalytic Chemistry, vol. 401, pp. 845-852 (2011).

Nachabe, R., D.J. Evers, B.H.W. Hendriks, G.W. Lucassen, M.van der Voort, E.J. Rutgers, M.J.V. Peeters, J.A. Van der Rage, H.S. Oldenburg, J. Wesseling, T.J.M. Ruers, "Diagnosis of breast cancer using diffuse optical spectroscopy from 500 to 1600nm: comparison of classification methods," Journal of Biomedical Optics, vol. 16, No. 8, article 087010, 12 pages (Aug. 2011).

Fantini, S. A. Sassaroli, "Near-infrared optical mammography for breast cancer detection with intrinsic contrast," Annals of Biomedical Engineering, vol. 40, No. 2, pp. 398-407 (Feb. 2012).

Akbari, H. K. Uto, Y. Kosugi, K. Kojima, N. Tanaka, "Cancer detection using infrared hyperspectral imaging," Cancer Science, vol. 102, No. 4, pp. 852-857 (Apr. 2011).

Parawira, S. "Classification of hyperspectral breast images for cancer detection," Dec. 4, 2009, downloaded from WWW, 5 pages.

Leff, D.R., O.J. Warren, L.C. Enfield, A. Gibson, T. Athanasion, D.K. Patten, J. Hebden, G.Z. Yang, A. Darzi, "Diffuse optical imaging of the healthy and diseased breast: a systematic review," Breast Cancer Research Treatment, vol. 108, pp. 9-22 (2008).

Konderpati, V.R., H.M. Heise, J. Backhaus, "Recent applications of near-infrared spectroscopy in cancer diagnosis and therapy," Annals of Bioanalytic Chemistry, vol. 390, pp. 125-139 (2008).

Taroni, P. D. Cornelli, A. Giusto, A. Pifferi, N. Shah, L. Spinelli, A. Torricelli, R. Cubeddu, "Assessment of collagen absorption and related potential diagnostic applications," Diffuse Optical Imaging of Tissue, adited by B.W. Pogue, R. Cubeddu, Proceedings of SPIE-OSA Biomedical Optics, SPIE vol. 6629, paper 66290D, 5 pages, (2007).

Mehrotra, R. A. Gupta, A. Kaushik, N. Prakash, H. Kandpal, "Infrared spectroscopic analysis of tumor pathology," Indian Journal of Experimental Biology, vol. 45, pp. 71-76 (Jan. 2007).

Urbas, A., M.W. Manning, A. Daugherty, L.A. Cassis, R.A. Lodder, "Near-infrared spectrometry of abdominal aortic aneurysm in the ApoE Mouse," Analytical Chemistry, vol. 75, No. 15, pp. 3650-3655 (Jul. 15, 2003).

Hirosawa, N. Y. Sakamoto, H. Katayama, S. Tonooka, K. Yano, "In vivo investigation of progressive alternations in rat mammary gland tumors by near-infrared spectroscopy," Analytical Biochemistry, vol. 305, pp. 156-165 (2002).

Istepanian, Robert H., "The Comparative Performance of Mobile Telemedical Systems based on the IS-54 and GSM Cellular Telephone Standards"; Journal of Telemedicine and Telecare 1999; pp. 97-104.

Aris, Ishak Bin, "An Internet-Based Blood Pressure Monitoring System for Patients"; Journal of Telemedicine and Telecare 2001; pp. 51-53.

Wang, Lohong V., Multiscale photoacoustic microscopy and computed tomography, Sep. 2009, Nature Photonics, vol. 3, pp. 503-509.

Islam, M. N., et al., "Broad bandwidths from frequency-shifting solitons in fibers", Optics Letters, vol. 14, No. 7, Apr. 1, 1989, pp. 370-372.

(56) References Cited

OTHER PUBLICATIONS

Islam, M. N., et al., "Femtosecond distributed soliton spectrum in fibers", J. Opt. Soc. Am. B, vol. 6, No. 6, Jun. 1989, pp. 1149-1158.
Busse, Lynda E., et al., "Design Parameters for Fluoride Multimode Fibers", Journal of Lightwave Technology, vol. 9, No. 7, Jul. 1991, pp. 828-831.
Wuthrich, Stefan, et al., "Optical damage thresholds at 2.94 um in fluoride glass fibers", Applied Optics, vol. 31, No. 27, Sep. 20, 1992, pp. 5833-5837.
Inoue, H., et al., "Computer simulation of the vibrational spectra and properties of fluoride glasses based on $ZrF_4$", Journal of Non-Crystalline Solids, vol. 161, 1993, pp. 118-122.
Mizunami, Toni, et al., "Gain saturation characteristics of Raman amplification in silica and fluoride glass optical fibers", Optics Communications 97, 1993, pp. 74-78.
Desthieux, B., et al., "111 kW (0. 5 mJ) pulse amplification at 1.5 um using a gated cascade of three erbium-doped fiber amplifiers," Appl. Phys. Lett. vol. 63, Aug. 2, 1993, pp. 586-588.
Edwards, Glenn, et al., Tissue ablation by a free-electron laser tuned to the amide II band, Nature, vol. 371, Sep. 29, 1994, pp. 416-419.
Borrelli, N. F., et al., "Resonant and non-resonant effects in photonic glasses", Journal of Non-Crystalline Solids 185, 1995, pp. 109-122.
Asobe, Masaki, et al., "Third-order nonlinear spectroscopy in $As_2S_3$ chalcogenide glass fibers", J. Appl. Phys. 77 (11), Jun. 1, 1995, pp. 5518-5523.
Jarman, Richard H., "Novel optical fiber lasers", Current Opinion in Solid State and Materials Science, 1996, pp. 199-203.
Iatridis, James C., et al., "Is the Nucleus Pulposus a Solid or a Fluid? Mechanical Behaviors of the Nucleus Pulposus of the Human Intervertebral Disc", Spine, vol. 21(10), May 15, 1996, pp. 1174-1184.
Asobe, Masaki, "Nonlinear Optical Properties of Chalcogenide Glass Fibers and Their Application to All-Optical Switching", Optical Fiber Technology, vol. 3, Article No OF970214, 1997, pp. 142-148.
Smektala, F., et al., "Chalcogenide glasses with large non-linear refractive indices", Journal of Non-Crystalline Solids 239, 1998, pp. 139-142.
Hamilton, James D., et al., "High Frequency Ultrasound Imaging with Optical Arrays", IEEE Transactions on Ultrasonics, Ferroelectrics, and Frequency Control, vol. 45, No. 1, Jan. 1998, pp. 216-235.
Hamilton, James D., et al., "High Frequency Ultrasound Imaging Using an Active Optical Detector", IEEE Transactions on Ultrasonics, Ferroelectrics, and Frequency Control, vol. 45, No. 3, May 1998, pp. 719-727.
Nowak, G. A., et al., "Low-power high-efficiency wavelength conversion based on modulational instability in high-nonlinearity fiber," Optics Letters, vol. 23, No. 12, Jun. 15, 1998, pp. 936-938.
Cardinal, T., et al., "Non-linear optical properties of chalcogenide glasses in the system As—S—Se", Journal of Non-Crystalline Solids 256 & 257, 1999, pp. 353-360.
Lucas, Jacques, "Infrared glasses", Current Opinion in Solid State & Materials Science 4, 1999. pp. 181-187.
Sanghera, J. S., et al., Active and passive chalcogenide glass optical fibers for IR applications: a review, Journal of Non-Crystalline Solids 256 & 257, 1999, pp. 6-16.
Nishida, Yoshiki, et al., "Reliability of Fluoride Fiber Module for Optical Amplifier Use", IEEE Photonics Technology Letters, vol. 11, No. 12, Dec. 1999, pp. 1596-1598.
Nowak, George A., et al., "Stable supercontinuum generation in short lengths of conventional dispersion-shifted fiber", Applied Optics, vol. 38, No. 36, Dec. 20, 1999, pp. 7364-7369.
Urban, J. P. G., et al., "The Nucleus of the Intervertebral Disc from Development to Degeneration" Amer. Zool., vol. 40, 2000, pp. 53-61.
Hamilton, James D., et al., "High Frequency Optoacoustic Arrays Using Etalon Detection", IEEE Transactions on Ultrasonics, Ferroelectrics, and Frequency Control, vol. 47, No. 1, Jan. 2000, pp. 160-169.

Ranka, Jinendra K., et al., "Visible continuum generation in air-silica microstructure optical fibers with anomalous dispersion at 800 nm", Optics Letters, vol. 25, No. 1, Jan. 1, 2000, pp. 25-27.
Boult, Maggi, et al., "Systematic Review of Percutaneous Endoscopic Laser Discectomy: Update and Re-appraisal", Australian Safety and Efficacy Register of New Interventional Procedures—Surgical Report No. 5, Feb. 2000, 49 pages.
Boult, Maggi, et al, "Percutaneous Endoscopic Laser Discectomy", Systematic Review, Aust. N.Z.J. Surg., vol. 70, Apr. 7, 2000, pp. 475-479.
Camacho, Nancy P., et al., "FTIR Microscopic Imaging of Collagen and Proteoglycan in Bovine Cartilage," Biopolymers (Biospectroscopy), vol. 62, 2001, pp. 1-8.
Choi, Joon Y., et al, "Thermal, Mechanical, Optical, and Morphologic Changes in Bovine Nucleus Pulposus Induced by Nd:YAG ($\lambda$= 1.32 um) Laser Irradiation", Lasers in Surgery and Medicine, vol. 28, 2001, pp. 248-254.
Hafez, M. I., et al., "The Effect of Irrigation on Peak Temperatures in Nerve Root, Dura, and Intervertebral Disk During Laser-Assisted Foraminoplasty", Lasers in Surgery and Medicine, vol. 29, 2001, pp. 33-37.
Jackson, Stuart D., et al., "Theory and numerical simulation of nth-order cascaded Raman fiber lasers", J. Opt. Soc. Am. B, vol. 18, No. 9, Sep. 2001, pp. 1297-1306.
Werle, Peter, et al., "Near- and mid-infrared laser-optical sensors for gas analysis", Optics and Lasers in Engineering 37, 2002, pp. 101-114.
Beck, Mattias, et al., "Continuous Wave Operation of a Mid-Infrared Semiconductor Laser at Room Temperature," Science vol. 295, www.sciencemag.org, Jan. 11, 2002, pp. 301-305.
Harbold, J. M., et al., "Highly nonlinear As—S—Se glasses for all-optical switching", Optics Letters, vol. 27, No. 2, Jan. 15, 2002, pp. 119-121.
Coen, Stephane, et al., "Supercontinuum generation by stimulated Raman scattering and parametric four-wave mixing in photonic crystal fibers", J. Opt. Soc. Am. B, vol. 19, No. 4, Apr. 2002, pp. 753-764.
Dudley, John M., et al., "Supercontinuum generation in air-silica microstructured fibers with nanosecond and femtosecond pulse pumping", J. Opt. Soc. Am. B, vol. 19, No. 4, Apr. 2002, pp. 765-771.
Harbold, Jeffrey M., et al., "Highly Nonlinear Ge—As—Se and Ge—As—S—Se Glasses for All-Optical Switching", IEEE Photonics Technology Letters, vol. 14, No. 6, Jun. 2002, pp. 822-824.
Husakou, Anton V., et al, "Supercontinuum generation, four-wave mixing, and fission of higher-order solitons in photonic-crystal fibers", J. Opt. Soc. Am. B, vol. 19, No. 9, Sep. 2002, pp. 2171-2182.
Wadsworth, William J., et al., "Supercontinuum generation in photonic crystal fibers and optical fiber tapers: a novel light source", J. Opt. Soc. Am. B, vol. 19, No. 9, Sep. 2002, pp. 2148-2155.
Kumar, V.V. Ravi Kanth, et al, "Extruded soft glass photonic crystal fiber for ultrabroad supercontiuum generation", Optics Express, vol. 10, No. 25, Dec. 16, 2002, pp. 1520-1525.
Edwards, Glenn S., et al., "Advantage of the Mark-III FEL for biophysical research and biomedical applications", J. Synchroton Rad. vol. 10, 2003, pp. 354-357.
Nicholson, J. W., et al., "Pulsed and continuous-wave supercontinuum generation in highly nonlinear, dispersion-shifted fibers", Applied Physics B 77, 2003, pp. 211-218.
Sobol, Emil, et al., "Time-resolved, light scattering measurements of cartilage and cornea denaturation due to free electron laser radiation", Journal of Biomedical Optics, vol. 8, No. 2, Apr. 2003, pp. 216-222.
Nicholson, J. W., et al., "All-fiber, octave-spanning supercontinuum", Optics Letters, vol. 28, No. 8, Apr. 15, 2003, pp. 643-645.
Faralli, S., et al., "Impact of Double Rayleigh Scattering Noise in Distributed Higher Order Raman Pumping Schemes", IEEE Photonics Technology Letters, vol. 15, No. 6, Jun. 2003, pp. 804-806.
"New and Emerging Techniques—Surgical, Rapid Review, Laser Discectomy", Australian Safety and Efficacy Register of New Interventional Procedures—Surgical, Jun. 2003, 12 pages.

(56) References Cited

OTHER PUBLICATIONS

Avdokhin, A. V., et al, "Continuous-wave, high-power, Raman continuum generation in noley fibers", Optics Letters, vol. 28, No. 15, Aug. 1, 2003, pp. 1353-1355.
Mussot, Arnaud, et al., "Generation of a broadband single-mode supercontinuum in a conventional dispersion-shifted fiber by use of a subnanosecond microchip laser", Optics Letters, vol. 28, No. 19, Oct. 1, 2003, pp. 1820-1822.
Slusher, Richard, et al., "Highly nonlinear composite chalcogenide/ polymer fibers", OSA 2004, 1 page.
Thongtrangan, Issada, et al., "Minimally invasive spinal surgery: a historical perspective", Neurosurg. Focus, vol. 16, Article 13, Jan. 2004, pp. 1-10.
Sun, Y., C.F. Booker, S. Kumari, R.N. Day, M. Davidson, A. Periasamy, "Characterization of an orange acceptor fluorescent protein for sensitized spectral fluorescence resonant energy transfer microscopy using a white-light laser," Journal of Biomedical Optics, vol. 14, No. 5, paper 054009 (2009).
Borlinghaus, R., "Colours Count: how the challenge of fluorescence was solved in confocal microscopy," in Modern Research and Educational Topics in Microscopy, A. Mendez-Vilas and J. Diaz, eds, pp. 890-899, Formatex (2007).
Borlinghaus, R., "The White Confocal: Continuous Spectral Tuning in Excitation and Emission," in Optical Fluorescence Microscopy, A. Diaspro (Ed), Chapter 2, pp. 37-54, ISBN 978-3-642-15174-3, Springer-Verlag, Berlin (2011).
Borlinghaus, R.T., L. Kuschel, "White Light Laser: The Ultimate Source for Confocal Microscopy," http://www.leica-microsystems. com/science-lab/white-light-laser (Jun. 27, 2012).
Ziegler, U., A.G. Bittermann, M. Hoechli, "Introduction to Confocal Laser Scanning Microscopy (LEICA)," www.zmb.unizh.ch, May 29, 2013.
Hori, Takashi, et al., "Flatly broadened, wideband and low noise supercontinuum generation in highly nonlinear hybrid fiber", Optics Express, vol. 12, No. 2, Jan. 26, 2004, pp. 317-324.
Wadsworth, W. J., et al., "Supercontinuum and four-wave mixing with Q-switched pulses in endlessly single-mode photonic crystal fibres", Optics Express, vol. 12, No. 2, Jan. 26, 2004, pp. 299-309.
Hilligsoe, Karen Marie, et al., "Supercontinuum generation in a photonic crystal fiber with two zero dispersion wavelengths", Optics Express, vol. 12, No. 6, Mar. 22, 2004, pp. 1045-1054.
Venugopalan, V., "Optical Society of America BIOMED Topical Meeting Tutorial on Tissue Optics", Apr. 27, 2004, pp. 1-32.
Slusher, Richart E., et al., "Large Raman gain and nonlinear phase shifts in high-purity As2So3 chalcogenide fibers", J. Opt. Soc. Am. B, vol. 21, No. 6, Jun. 2004, pp. 1146-1155.
Leon-Saval, S. G., et al., "Supercontinuum generation in submicron fibre waveguides", Optics Express, vol. 12, No. 13, Jun. 28, 2004, pp. 2864-2869.
Nicholson, J. W., et al., "High power, single mode, all-fiber source of femtosecond pulses at 1550 nm and its use in supercontinuum generation", Optics Express, vol. 12, No. 13, Jun. 28, 2004, pp. 3025-3034.
Genty, G., et al., "Enhanced bandwidth of supercontinuum generated m microstructured fibers", Optics Express, vol. 12, No. 15, Jul. 26, 2004, pp. 3471-3480.
Champert, Pierre-Alain, et al., "White-light supercontinuum generation in normally dispersive optical fiber using original multi-wavelength pumping system", Optics Express, vol. 12, No. 19, Sep. 20, 2004, pp. 4366-4371.
Nicholson, J. W., "Supercontinuum generation in ultraviolet-irradiated fibers", Optics Letters, vol. 29, No. 20, Oct. 15, 2004, pp. 2363-2365.
Hori, Takashi, et al., "Experimental and numerical analysis of widely broadened supercontinuum generation in highly nonlinear dispersion-shifted fiber with a femtosecond pulse", J. Opt. Soc. Am. B, vol. 21, No. 11, Nov. 2004, pp. 1969-1980.
Demircan, Ayhan, et al., "Supercontinuum generation by the modulation instability", Optics Communications 244, 2005, pp. 181-185.
Papemyi, S. B., et al., "Sixth-Order Cascaded Raman Amplification", OFC/NFOEC, 2005, 3 pages.
Tanaka, Keiji, "Optical nonlinearity in photonic glasses", Journal of Materials Science: Materials in Electronics 16, 2005, pp. 633-643.
Nestbrook, Paul S., "Improved Supercontinuum Generation Through UV Processing of Highly Nonlinear Fibers", Journal of Lightwave Technology, vol. 23, No. 1, Jan. 2005, pp. 13-18.
Abeeluck, Akheelesh K., et al., "Continuous-wave pumping in the anomalous- and normal dispersion regimes of nonlinear fibers for supercontinuum generatfon", Optics Letters, vol. 30, No. 1, Jan. 1, 2005, pp. 61-63.
Kutz, J. Nathan, et al., "Enhanced Supercontinuum Generation through Dispersion-Management", Optics Express, vol. 13, No. 11, May 30, 2005, pp. 3989-3998.
Lee, Ju Han, et al., "Experimental performance comparison for various continuous-wave supercontinuum schemes: ring cavity and single pass structures", Optics Express, vol. 13, No. 13, Jun. 27, 2005, pp. 4848-4853.
Saliminia, A., et al., "Ultra-broad and coherent white light generation in silica glass by focused femtosecond pulses at 1.5pm", Optics Express, vol. 13, No. 15, Jul. 25, 2005, pp. 5731-5738.
Takushima, Yuichi, High average power, depolarized super-continuum generation using a 1.55-um ASE noise source, Optics Express, vol. 13, No. 15, Jul. 25, 2005, pp. 5871.-5877.
Travers, J. C., et al., "Extended continuous-wave supercontinuum generation in a low-water-loss holey fiber", Optics Letters, vol. 30, No. 15, Aug. 1, 2005, pp. 1938-1940.
Kobtsev, Serguei M., et al., "Modelling of high-power supercontinuum generation in highly nonlinear, dispersion shifted fibers at CW pump", Optics Express, vol. 13, No. 18, Sep. 5, 2005, pp. 6912-6918.
Falk, Peter, et al., "Supercontinuum generation in a photonic crystal fiber with two zero-dispersion wavelengths tapered to normal dispersion at all wavelengths", Optics Express, vol. 13, No. 19, Sep. 19, 2005, pp. 7535-7540.
Tombelaine, Vincent, et al., "Ultra wide band supercontinuum generation in air-silica holey fibers by SHG-induced modulation instabilities", Optics Express, vol. 13, No. 19, Sep. 19, 2005, pp. 7399-7404.
Lee, Ju Han, et al., "Continuous-wave supercontinuum laser based on an erbium-doped fiber ring cavity incorporating a highly non-linear optical fiber", Optics Letters, vol. 30, No. 19, Oct. 1, 2005, pp. 2599-2601.
Genty, G., et al., "Supercontinuum generation in large mode-area microstructured fibers", Optics Express, vol. 13, No. 21, Oct. 17, 2005, pp. 8625-8633.
Schreiber, T., et al., "Supercontinuum generation by femtosecond single and dual wavelength pumping in photonic crystal fibers with two zero dispersion wavelengths", Optics Express, vol. 13, No. 23, Nov. 14, 2005, pp. 9556-9569.
Travers, J. C., et al., "Extended blue supercontinuum generation in cascaded holey fibers", Optics Letters, vol. 30, No. 23, Dec. 1, 2005, pp. 3132-3134.
Hagen, C. L., et al., "Generation of a Continuum Extending to the Midinfrared by Pumping ZBLAN Fiber With an Ultrafast 1550-nm Source", IEEE Photonics Technology Letters, vol. 18, No. 1, Jan. 1, 2006, pp. 91-93.
Moon, Sucbei, et al., "Generation of octave-spanning supercontinuum with 1550-nm amplified diode-laser pulses and a dispersion-shifted fiber", Optics Letters, vol. 14, No. 1, Jan. 9, 2006, pp. 270-278.
Fedotova, O., et al., "Supercontinuum generation in planar rib waveguides enabled by anomalous dispersion", Optics Express, vol. 14, No. 4, Feb. 20, 2006, pp. 1512-1517.
Harrington, James A., "Infrared Fiber Optics", OSA Handbook, vol. III, white paper, to be published by McGraw Hill, Undated, 13 pages.
Aaviksoo, J., et al., "Observation of optical precursors at pulse propagation in GaAs", Physical Review A, vol. 44, No. 9, Nov. 1, 1991, pp. R5353-R5356.
Boppart, Stephen A., et al., "Imaging developing neural morphology using optical coherence tomography", Journal of Neuroscience Methods 70, 1996, pp. 65-72.

(56) References Cited

OTHER PUBLICATIONS

Boppart, Stephen A., et al., "Noninvasive assessment of the developing Xenopus cardiovascular system using optical coherence tomography", Prec. Natl. Acad. Sci. USA, vol. 94, Apr. 1997, pp. 4256-4261.

Tearney, Guillermo J., et al., "In vivo Endoscopic Optical Biopsy with Optical Coherence Tomography", Science, New Series, vol. 276, Jun. 27, 1997, pp. 2037-2039.

de Boer, Johannes F., et al., "Imaging thermally damaged tissue by polarization sensitive optical coherence tomography", Optics Express 212, vol. 3, No. 6, Sep. 14,1998, pp. 212-218.

Roggen, Andre, et al., "Optical Properties of Circulating Human Blood in the Wavelength Range 400-2500 NM", Journal of Biomedical Optics, vol. 4, No. 1, Jan. 1999, pp. 36-46.

de Boer, Johannes F., et al., "Determination of the depth-resolved Stokes parameters of light backscattered from turbid media by use of polarization-sensitive optical coherence tomography", Optics Letters, vol. 24, No. 5; Mar. 1, 199, pp. 300-302.

Rollins, Andrew M., et al., "Real-time in vivo imaging of human gastrointestinal ultrastructure by use of endoscopic optical coherence tomography with a novel efficient interferometer design", Optics Letters, vol. 24, No. 19, Oct. 1, 1999, pp. 1358-1360.

D'Amico, Anthony V., et al., "Optical Coherence Tomography As a Method for Identifying Benign and Malignant Microscopic Structures in the Prostate Gland", Basic Science, Urology 55 (5), 2000, pp. 783-787.

Li, Xingde, et al., "Imaging needle for optical coherence tomography", Optics Letters, vol. 25, No. 20, Oct. 15, 2000, pp. 1520-1522.

Oughstun, Kurt E., "Influence of precursor fields on ultrashort pulse autocorrelation measurements and pulse width evolution", Optics Express, vol. 8, No. 8, Apr. 9, 2001, pp. 481-491.

Kowalevicz, Andrew M., et al., "Ultrahigh resolution optical coherence tomography using a superluminescent light source" Optics Express 349, vol. 10, No. 7, Apr. 8, 2002, pp. 349-353.

Povazay, B., et al., "Submicrometer axial resolution optical coherence tomography", Optics Letters, vol. 27, No. 20, Oct. 15, 2002, pp. 1800-1802.

Xie, T.-Q., et al., "Detection of tumorigenesis in urinary bladder with optical coherence tomography: optical characterization of morphological changes", Optics Express, vol. 10, No. 24, Dec. 2, 2002, 2003, pp. 1431-1443.

Seefeldt, Michael, et al., "Compact white-light source with an average output power of 2.4 Wand 900 nm spectral bandwidth", Optics Communications 216, pp. 199-202.

Wang, Yimin, et al., "Ultrahigh-resolution optical coherence tomography by broadband continuum generation from a photonic crystal fiber", Optics Letters, vol. 28, No. 3, Feb. 1, 2003, pp. 182-184.

Bizheva, K, et al., "Compact, broad-bandwidth fiberlaserforsub-2-pm axial resolution optical coherence tomography in the 1300-nm wavelength region," Optics Letters, vol. 28, No. 9, May 1, 2003, pp. 707-709.

Pan, Yingtian, et al., "Hand-held arthroscopic optical coherence tomography for in vivo sigh-resolution imaging of articular cartilage", Journal of Biomedical Optics 8(4), Oct. 2003, pp. 648-654.

Xie, Tuqiang, et al., "Endoscopic optical coherence tomography with a modified microelectromechanical systems mirror for detection of bladder cancers", Applied Optics, vol. 42, No. 31, Nov. 1, 2003, pp. 6422-6426.

Dubois, A., et al., "Three-dimensional cellular-level imaging using full-field optical coherence tomography", Physics in Medicine and Biology, Phys. Med. Biol. 49, 2004, pp. 1227-1234.

Park, Jesung, et al., "Analysis of birefringent image in the retinal nerve fiber layer by polarization sensitive optical coherence tomography", Ophthalmic Technologies XIV, Proceedings of SPIE, vol. 5314, 2004, pp. 188-194.

Unterhuber, A., et al., "Advances in broad bandwidth light sources for ultrahigh resolution optical coherence tomography", Physics in Medicine and Biology, Phys. Med. Biol. 49, 2004, pp. 1235-1246.

Drexler, Wolfgang, "Ultrahigh-resolution optical coherence tomography", Journal of Biomedical Optics, vol. 9, No. 1, Jan./Feb. 2004, pp. 47-74.

Schmitt, Joseph, et al., "Intravascular Optical Coherence Tomography Opens a Window Onto Coronary Artery Disease", Optics & Photonics News, Feb. 2004, pp. 20-25.

Nassif, N. A., et al., "In vivo high-resolution video-rate spectral-domain optical coherence tomography of the human retina and optic nerve", Optics Express, vol. 12, No. 3, Feb. 9, 2004, pp. 367-376.

Choi, Seung-Ho, et al., "Observation of Optical Precursors in Water", Physical Review Letters, vol. 92, No. 19, May 14, 2004, pp. 193903-1-193903-3.

Pierce, Mark C., et al., "Advances in Optical Coherence Tomography imaging for Dermatology", Optical Coherence Tomography Advances, The Journal of Investigate Dermatology, Sep. 3, 2004, pp. 458-463.

"State-Specitic Trends in Chronic Kidney Failure—United States, 1990-2001", Morbidity and Mortality Weekly Report, Department of Health and Human Services Centers for Disease Control and Prevention, vol. 53, No. 39, copied from internet: file:// C:\Documents and Settings\eturlo\Desktop\State-Specific Trends in Chronic Kidney . . . Feb. 12, 2010, Oct. 8, 2004, pp. 918-920.

I.B. Ads, A.A.E. Wagie, N.B. Mariun, A.B.E. Jammal, "An Internet-based blood pressure monitoring system for patients," Journal of Telemedicine and Telecare, 2001, pp. 51-53.

R.H. Istepanian, B. Woodward, P.A. Bales, S. Chen, B. Luk, "The comparative performance of mobile telemediCal systems based on the IS-S4 and GSM cellular telephone standards," Journal of Telemedicine and Telecare, 1999, pp. 97-104.

Shaw, et al, IR Supercontinuum Generation in As—Se Photonic Crystal Fiber, Optical Society of America, Copyright 2005, 3 pages.

PCT/US06/44451, Notification of Transmittal of the International Search Report and the Written Opinion of the International Searching Authority, or the Declaration, Nov. 29, 2007, 12 pages.

G.S. Edwards et al., "Free-electron-laser-based biophysical and biomedical instrumentation," American Institute of Physics, vol. 74, No. 7, Jul. 2003, pp. 3207-3245.

Computer Motion, Inc., "501(k) Summary -ZEUS® MicroWrist™ Surgical System and Accessroies," Sep. 24, 2002, 6 pages.

Computer Motion, Inc. "HERMES™ O.R. Control Center—510(k) Summary of Safety and Effectiveness," Oct. 11, 2002, 5 pages.

K.M. Joos, et al. "Optic Nerve Sheath Fenestration with a Novel Wavelength Produced by the Free Electron Laser (FEL)," Lasers in Surgery and Medicine, 27: 2000,191-205.

J. Sanghera, I. Aggarwal, "IR Fiber Optics at NRL," undated, 10 pages.

J. Sanghera, L.B. Shaw, I.D. Aggarwal, "Applications of chalcogenide glass optical fibers," Academic of Science, 2003, pp. 1-11.

B. Rigas, P.T.T. Wong, "Human Colon Adenocarcinoma Cell Lines Display Infrared Spectroscopic Features," Cancer Research, Jan. 1, 1992, pp. 84-88.

G. Edwards, et al., "Comparison of OPA and Mark-III FEL for Tissue Ablation at 6.45 Microns," Department of Physics and Free Electron Laser Laboratory, Duke University, 2002, 7 pages.

Glenn Edwards, "Biomedical and potential clinical applications for pulsed lasers operating near 6.45 um," Society of Photo-Optical Instrumentation Engineers, 1995, 2 pages.

Passat, "Solid-State Lasers and Optical Components," Jul. 14, 2003, 5 pages.

P.A. Thielen and L.B. Shaw, et al., "Small-core As—Se fiber for Raman amplification," Optics Leti-Ers, vol. 28, No. 16, Aug. 15, 2003, 3 pages.

R.Rox Anderson, et al., "Selective Photothermolysis: Precise Microsurgery by Selective Absorption of Pulsed Radiation," Department of Dermatology, Harvard Medical School, Science, vol. 220, Apr. 29, 1983, 4 pages.

U.S. Appl. No. 10/652,276, "System and Method for Voice Control of Medical devices," by Mohammed N. Islam, abandoned (074036.0129) Date filed: Aug. 29, 2003.

U.S. Appl. No. 10/757,341, "System and Method for Voice Control of Medical devices," by Mohammed N. Islam, dated (074036.0132) Date filed: Jan. 13, 2004.

(56) References Cited

OTHER PUBLICATIONS

U.S. Appl. No. 12/206,432, "System and Method for Voice Control of Medical Devices," by Mohammed N. Islam, pending (074036.0154) Date filed: Sep. 8, 2008.
U.S. Patent and Trademark Office, Office Action for U.S. Appl. No. 12/206,432, filed Sep. 8, 2008, Mohammed N, Islam, Date filed: Mar. 12, 2009.
U.S. Patent and Trademark Office, Notice of Allowance and Fee(s) Due for U.S. Appl. No. 12/206,432, filed Sep. 8, 2008, Mohammed N. Islam, Date filed: Aug. 28, 2009.
Hazen, K.H., M.A. Arnold, G.W. Small, "Measurement of glucose and other analytes in undiluted human serum with near-infrared transmission spectroscopy," Analytica Chimica Acta, vol. 371, pp. 255-267 (1998).
Malin, S.F., T.L Ruchti, T.B. Blank, S.N. Thennadil, S.L. Monfre, "Noninvasive prediction of glucose by near-infrared diffuse reflectance spectroscopy," Clinical Chemistry, vol. 45, No. 9, pp. 1651-1658 (1999).
Thennadil, S.N., J.L. Rennert, B.J. Wenzel, K.H. Hazen, T.L. Ruchti, M.B. Block, "Comparison of glucose concentration in interstitial fluid, and capillary and venous blood during rapid changes in blood glucose levels," Diabetes Technology & Therapeutics, vol. 3, No. 3, pp. 357-365 (2001).
Troy, T.L, S.N. Thennadil, "Optical properties of human skin in the near infrared wavelength range of 1000 to 2200nm," Journal of Biomedical Optics, vol. 6, No. 2, pp. 167-176, (2001).
Blank, T.B., T.L. Ruchti, A.D. Lorenz, S.L. Monfre, M.R. Makarewicz, M. Mattu, K.H. Hazen, "Clinical results from a non-invasive blood glucose monitor," Optical Diagnostics and Sensing of Biological Fluids and Glucose and Cholesterol Monitoring II, A.V. Priezzhev and G.L. Cote, Editors, Proceedings of SPIE, vol. 4624, pp. 1019 (2002).
Yeh, S-J, C.F. Hanna, O.S. Khalil, "Monitoring blood glucose changes in cutaneous tissue by temperature-modulated localized reflectance measurements," Clinical Chemistry, vol. 49, No. 6, pp. 924-934 (2003).
Marbach, R., T. Koschinsky, F.A. Gries, H.M. Heise, "Noninvasive blood glucose assay by near-infrared diffuse reflectance spectroscopy of the human inner lip," Applied Spectroscopy, vol. 47, No. 7, pp. 875-881 (1993).
Enejder, A.M.K., T.G. Scecina, J. Oh, M. Hunter, W.C. Shih, S. Sasic, G.L. Horowitz, M.S. Feld, "Raman spectroscopy for noninvasive glucose measurements," Journal of Biomedical Optics, vol. 10, No. 3, 031114 (2005).
Olesberg, J.T., L. Liu, V.V. Zee, M.A. Arnold, "In vivo near-infrared spectroscopy of rat skin tissue with varying blood glucose levels," Analytic Chemistry, vol. 78, No. 1, pp. 215-223 (2006).
Olesberg, J.T., M.A. Arnold, C. Mermelstein, J. Schmitz, J. Wagner, "Tunable laser diode system for noninvasive blood glucose measurements," Applied Spectroscopy, vol. 59, No. 12, pp. 1480-1484 (2005).
Harman-Boehm, I. A. Gal, A.M. Raykhman, J.D. Zahn, E. Naidis, Y. Mayzel, "Noninvasive glucose monitoring: a novel approach," Journal of Diabetes Science and Technology, vol. 3, No. 2 pp. 253-260 (2009).
Kim-K.D., G.S. Son, S.S. Lim, S.S. Lee, "Measurement of glucose level exploiting a relative optical absorption at discrete probe wavelengths," Japanese Journal of Applied Physics, vol. 48, 077001 (2009).
Smith, J.L., "The Pursuit of Noninvasive Glucose: Hunting the Deceitful Turkey," 2nd Edition, pp. 1-141 (2011).
Pezzaniti, J.L., T.W. Jeng, L. McDowell, G.M. Oosta, "Preliminary investigation of near-infrared spectroscopic measurements of urea, creatinine, glucose, protein and ketone in urine," Clinical Biochemistry, vol. 34, pp. 239-246 (2001).
Lussi, A., R. Hibst, R. Paulus, "Diagnodent: An optical method for caries detection," Journal of Dental Research, vol. 83, special issue C, pp. C80-C83 (2004).

Reese, E.L, E.E. Fisher, D.A. Horowitz, "Photoelectric densitometry of the circulation of the human dental pulp," The Journal of the Baltimore College of Dental Surgery, vol. 26, No. 1, pp. 6-18 (1971).
Zakian, C., I. Pretty, R. Ellwood, "Near-infrared hyperspectral imaging of teeth for dental canes detection," Journal of Biomedical Optics, vol. 16, No. 6, 064047 (2009).
Belikov, A.V., A.V. Skripnik, K.V. Shatilova, "Study of the dynamics of the absorption spectra of human tooth enamel and dentine under heating and ablation by submillisecond pulse radiation of an erbium laser with a generation wavelength of 2.79 um," Optics and Spectroscopy, vol. 109, No. 2, pp. 211-216 (2010).
Karlsson, L. "Caries detection methods based on changes in optical properties between healthy and carious tissue," International Journal of Dentistry, vol. 2010, Article ID 270729, 9 pages (2010).
Fried, D. M. Staninec, C.L. Darling, "Near-infrared imaging of dental decay at 1310nm," Journal of Laser Dentistry, vol. 18, No. 1, pp. 8-16 (2010).
Burmen, M. P. Usenik, A. Fidler, F. Pernus, B. Likar, "A construction of standardized near infrared hyper-spectral teeth database—a first step in the development of reliable diagnostic tool for quantification and early detection of caries," Lasers in Dentistry XVII, edited by P. Rechmann, D. Fried, Proceedings of SPIE, vol. 7884, Paper 78840E (2011).
Maia, A., L. Karlsson, W. Margulis, A. Gomes, "Evaluation of two imaging techniques: near-infrared transillumination and dental radiographs for the detection of early approximal enamel canes," Dentomaxillofacial Radiology, vol. 40, pp. 429-433 (2011).
Chung, S., D. Fried, M. Staninec, C.L. Darling, "Multispectral near-IR reflectance and transillumination imaging of teeth," Biomedical Optics Express, vol. 2, No. 10, pp. 2804-2814 (2011).
Chung, S., D. Fried, M. Staninec, C.L. Darling, "Near infrared imaging of teeth at wavelengths between 1200 and 1600nm," Proceedings of the Society of Photo Optical Instrument Engineering, paper 7884 (2011).
Staninec, M., S.M. Douglas, C.L. Darling, K. Chan, H. Kang, R. C. Lee, D. Fried, "Nondestructive clinical assessment of occlusal caries lesions using near-IR imaging methods," Lasers in Surgery and Medicine, vol. 43, No. 10, pp. 951-959 (2011).
Nishizawa, N., "Generation and application of high-quality supercontinuum sources," Optical Fiber Technology, vol. 18, pp. 394-402 (2012).
Inter Partes Review No. IPR2021-00453; Petition for Inter Partes Review of U.S. Pat. No. 10,517,484; *Apple Inc.* v. *Omni Medsci, Inc.;* pp. 1-103; dated Jan. 22, 2021.
File History for U.S. Pat. No. 10,517,484 dated Dec. 24, 2019, 1223 pages.
Declaration of Brian Anthony regarding U.S. Pat. No. 10,517,484 in IPR2021-00453, Jan. 22, 2021, 138 pages.
Affidavit of Process Server, *Omni MedSci, Inc.* v. *Apple Inc.*, No. 3:20-cv-00563-KAW (N.D. Cal.), Jan. 29, 2020, 1 page.
Deposition Transcript of Duncan Leo MacFarlane, Ph.D., P.E., *Apple Inc.* v. *Omni MedSci, Inc.*, IPR2019-00916 (PTAB Apr. 16, 2020), 102 pages.
Order Granting Motion to Stay Pending Interlocutory Appeal Related to Standing Question, *Omni MedSci, Inc.* v. *Apple Inc.*, No. 20-cv-00563-YGR (N.D. Cal. Apr. 28, 2020), 2 pages.
Omni Preliminary Proposed Claim Constructions, Nov. 1, 2018. Case No. 2:18-cv-134-RWS, 1 page.
Inter Partes Review No. IPR2019-00916; Final Written Decision of U.S. Pat. No. 9,651,533 *Apple Inc.* v. *Omni Medsci, Inc.*; pp. 1-67; dated Oct. 14, 2020.
Wolfson, "The lock-in amplifier: A student experiment", American Journal of Physics, vol. 59, No. 6, pp. 569-572, 1991.
Baylor et al., "Lock-in amplifiers go digital", Laser & Optronics, vol. 10, Issue 4, 4 pages, 1991.
Rignot, et al., "Change Detection Techniques for ERS-1 SAR Data", IEEE Transactions on Geoscience and Remote Sensing, vol. 31, No. 4, pp. 896-906, Jul. 1993.
Mandelis, "Signal-to-noise ratio in lock-in amplifier synchronous detection: A generalized communications systems approach with

(56) References Cited

OTHER PUBLICATIONS applications to frequency, time, and hybrid (rate window) photothermal measurements", Review of Scientific Instruments, vol. 65, pp. 3309-3323, 1994.
Lu et al., "Change detection techniques, International Journal of Remote Sensing", vol. 25, No. 12, pp. 2365-2401, 2004.
Coppin et al., "Digital change detection methods in ecosystem monitoring: a review", International Journal of Remote Sensing, vol. 25, No. 9, pp. 1565-1596, 2004.
Burdett, "181: Amplitude Modulated Signals: The Lock-in Amplifier", Handbook of Measuring System Design, John Wiley & Sons, Ltd., pp. 1197-1208, 2005.
Radke, et al., "Image Change Detection Algorithms: A Systematic Survey", IEEE Transaction on Image Processing, vol. 14, No. 3, pp. 294-307, Mar. 2005.

\* cited by examiner

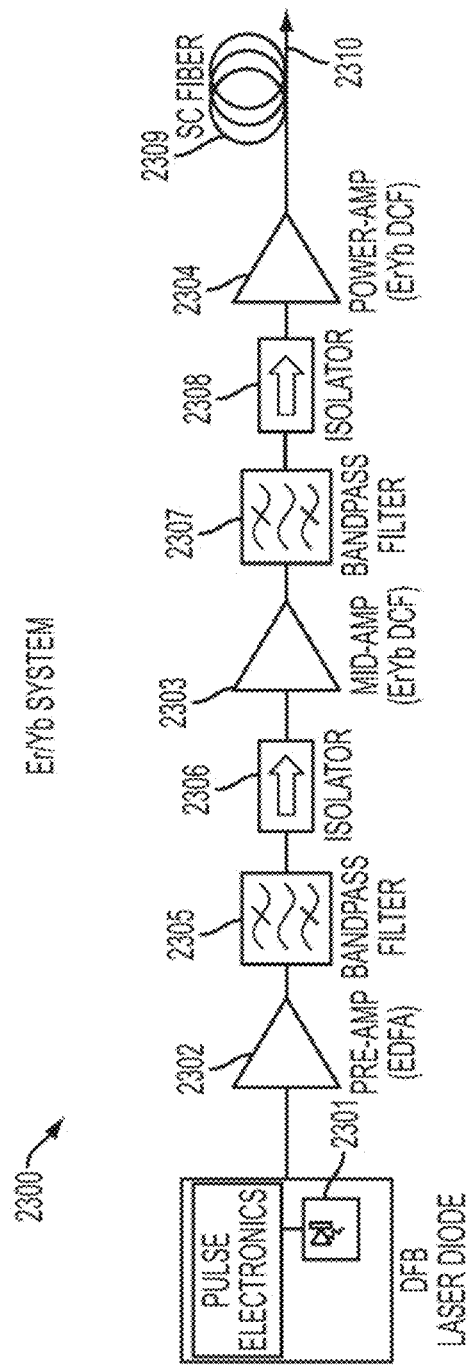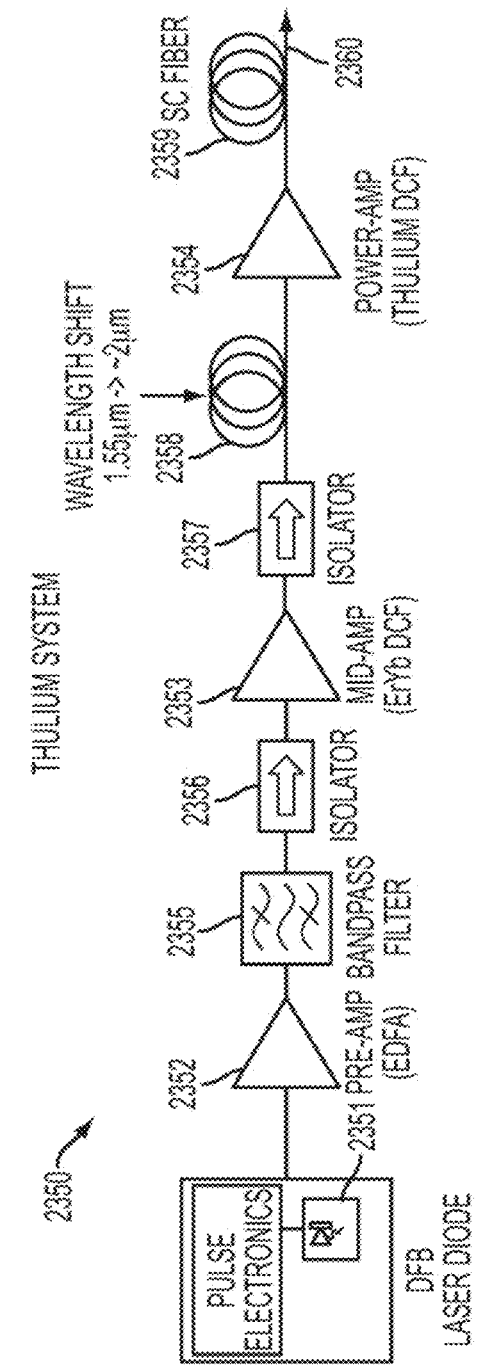
FIG. 23A
FIG. 23B

HIGH SIGNAL-TO-NOISE RATIO LIGHT SPECTROSCOPY OF TISSUE

CROSS-REFERENCE TO RELATED APPLICATIONS

This application is a continuation of U.S. application Ser. No. 14/109,007 filed Dec. 17, 2013, now U.S. Pat. No. 9,993,159, which claims the benefit of U.S. provisional application Ser. No. 61/747,553 filed Dec. 31, 2012, the disclosures of which are hereby incorporated in their entirety by reference herein.

This application is related to U.S. provisional application Ser. Nos. 61/747,477 filed Dec. 31, 2012; Ser. No. 61/747,481 filed Dec. 31, 2012; Ser. No. 61/747,485 filed Dec. 31, 2012; Ser. No. 61/747,487 filed Dec. 31, 2012; Ser. No. 61/747,492 filed Dec. 31, 2012; Ser. No. 61/747,472 filed Dec. 31, 2012; and Ser. No. 61/754,698 filed Jan. 21, 2013, the disclosures of which are hereby incorporated in their entirety by reference herein This application is related to International Application No. PCT/US13/075700 entitled Near-Infrared Lasers For Non-Invasive Monitoring Of Glucose, Ketones, HBA1C, And Other Blood Constituents; International Application No. PCT/US13/075736 entitled Short-Wave Infrared Super-Continuum Lasers For Early Detection Of Dental Caries; U.S. application Ser. No. 14/108,995 entitled Focused Near-Infrared Lasers For Non-Invasive Vasectomy And Other Thermal Coagulation Or Occlusion Procedures; International Application No. PCT/US13/075767 entitled Short-Wave Infrared Super-Continuum Lasers For Natural Gas Leak Detection, Exploration, And Other Active Remote Sensing Applications; U.S. application Ser. No. 14,108,986 entitled Short-Wave Infrared Super-Continuum Lasers For Detecting Counterfeit Or Illicit Drugs And Pharmaceutical Process Control; and U.S. application Ser. No. 14/108,974 entitled Focused Near-Infrared Lasers For Non-Invasive Varicose Veins And Other Thermal Coagulation Or Occlusion Procedures, the disclosures of which are hereby incorporated in their entirety by reference herein.

TECHNICAL FIELD

This disclosure relates to a diagnostic system using lasers and light sources with near-infrared spectroscopy.

BACKGROUND AND SUMMARY

Breast cancer is considered to be the most common cancer among women in industrialized countries. It is believed that early diagnosis and consequent therapy could significantly reduce mortality. Mammography is considered the gold standard among imaging techniques in diagnosing breast pathologies. However, the use of ionizing radiation in mammography may have adverse effects and lead to other complications. Moreover, screening x-ray mammography may be limited by false positives and negatives, leading to unnecessary physical and psychological morbidity. Although breast cancer is one of the focuses of this disclosure, the same techniques may also be applied to other cancer types, including, for example, skin, prostate, brain, pancreatic, and colorectal cancer.

Diagnostic methods for assessment and therapy follow-up of breast cancer include mammography, ultrasound, and magnetic resonance imaging. The most effective screening technique at this time is x-ray mammography, with an overall sensitivity for breast cancer detection around 75%, which is even further reduced in women with dense breasts to around 62%. Moreover, x-ray mammography has a 22% false positive rate in women under 50, and the method cannot accurately distinguish between benign and malignant tumors. Magnetic resonance imaging and ultrasound are sometimes used to augment x-ray mammography, but they have limitations such as high cost, low throughput, limited specificity and low sensitivity. Thus, there is a continued need to detect cancers earlier for treatment, missed by mammography, and to add specificity to the procedures.

Optical breast imaging may be an attractive technique for breast cancer to screen early, augment with mammography, or use in follow-on treatments. Also, optical breast imaging may be performed by intrinsic tissue contrast alone (e.g., hemoglobin, water, collagen, and lipid content), or with the use of exogenous fluorescent probes that target specific molecules. For example, near-infrared (NIR) light may be used to assess optical properties, where the absorption and scattering by the tissue components may change with carcinoma. For most of the studies conducted to date, NIR light in the wavelength range of 600-1000 nm has been used for sufficient tissue penetration; these wavelengths have permitted imaging up to several centimeters deep in soft tissue. Optical breast imaging using fluorescent contrast agents may improve lesion contrast and may potentially permit detection of changes in breast tissue earlier. In one embodiment, the fluorescent probes may either bind specifically to certain targets associated with cancer or may non-specifically accumulate at the tumor site.

Optical methods of imaging and spectroscopy can be non-invasive using non-ionizing electromagnetic radiation, and these techniques could be exploited for screening of wide populations and for therapy monitoring. "Optical mammography" may be a diffuse optical imaging technique that aims at detecting breast cancer, characterizing its physiological and pathological state, and possibly monitoring the efficacy of the therapeutic treatment. The main constituents of breast tissue may be lipid, collagen, water, blood, and other structural proteins. These constituents may exhibit marked and characteristic absorption features in the NIR wavelength range. Thus, diffuse optical imaging and spectroscopy in the NIR may be helpful for diagnosing and monitoring breast cancer. Another advantage of such imaging is that optical instruments tend to be portable and more cost effective as compared to other instrumentation that is conventionally used for medical diagnosis. This can be particularly true, if the mature technologies for telecommunications and fiber optics are exploited.

Spectroscopy using NIR or short-wave infrared (SWIR) light may be beneficial, because most tissue has organic compounds that have overtone or combination absorption bands in this wavelength range (e.g., between approximately 0.8-2.5 microns). In one embodiment, a NIR or SWIR super-continuum (SC) laser that is an all-fiber integrated source may be used as the light source for diagnosing cancerous tissue. Exemplary fiber-based super-continuum sources may emit light in the NIR or SWIR between approximately 1.4-1.8 microns, 2-2.5 microns, 1.4-2.4 microns, 1-1.8 microns, or any number of other bands. In particular embodiments, the detection system may be one or more photo-detectors, a dispersive spectrometer, a Fourier transform infrared spectrometer, or a hyper-spectral imaging detector or camera. In addition, reflection or diffuse reflection light spectroscopy may be implemented using the SWIR light source, where the spectral reflectance can be the ratio of reflected energy to incident energy as a function of wavelength.

For breast cancer, experiments have shown that with growing cancer the collagen content increases while the lipid content decreases. Therefore, early breast cancer detection may involve the monitoring of absorption or scattering features from collagen and lipids. In addition, NIR spectroscopy may be used to determine the concentrations of hemoglobin, water, as well as oxygen saturation of hemoglobin and optical scattering properties in normal and cancerous breast tissue. For optical imaging to be effective, it may also be desirable to select the wavelength range that leads to relatively high penetration depths into the tissue. In one embodiment, it may be advantageous to use optical wavelengths in the range of about 1000-1400 nm. In another embodiment, it may be advantageous to use optical wavelengths in the range of about 1600-1800 nm. Higher optical power densities may be used to increase the signal-to-noise ratio of the detected light through the diffuse scattering tissue, and surface cooling or focused light may be beneficial for preventing pain or damage to the skin and outer layer surrounding the breast tissue. Since optical energy may be non-ionizing, different exposure times may be used without danger or harmful radiation.

In one embodiment, a diagnostic system comprises a light source configured to generate an output optical beam comprising: one or more semiconductor sources configured to generate an input beam; one or more optical amplifiers configured to receive at least a portion of the input beam and to deliver an intermediate beam to an output end of the one or more optical amplifiers; one or more optical fibers configured to receive at least a portion of the intermediate beam and to deliver at least the portion of the intermediate beam to a distal end of the one or more optical fibers to form a first optical beam; a nonlinear element configured to receive at least a portion of the first optical beam and to broaden a spectrum associated with the at least a portion of the first optical beam to at least 10 nanometers through a nonlinear effect in the nonlinear element to form the output optical beam with an output beam broadened spectrum; and an interface device configured to receive a received portion of the output optical beam and configured to deliver a delivered portion of the output optical beam to a tissue sample, wherein the interface device comprises a cap with fiber leads configured to couple to the light source and to a receiver comprising one or more detectors. At least a portion of the output beam broadened spectrum comprises a near-infrared wavelength between 600 nanometers and 1000 nanometers. The receiver is configured to receive at least a portion of a diffuse spectroscopy output beam that results from light diffusion of the delivered portion of the output optical beam into a top two (2) millimeters or more of the tissue sample and configured to process the portion of the spectroscopy output beam to generate an output signal that monitors absorption or scattering features of the tissue sample. The tissue sample may comprise at least in part brain tissue, and the output signal may provide information related to oxy- and deoxy-hemoglobin, or related to metabolism.

Embodiments may include a diagnostic system comprising a light source configured to generate an output optical beam, comprising: one or more semiconductor sources configured to generate an input beam; one or more optical amplifiers configured to receive at least a portion of the input beam and to deliver an intermediate beam to an output end of the one or more optical amplifiers; one or more optical fibers configured to receive at least a portion of the intermediate beam and to deliver at least the portion of the intermediate beam to a distal end of the one or more optical fibers to form a first optical beam; and a nonlinear element configured to receive at least a portion of the first optical beam and to broaden a spectrum associated with the at least a portion of the first optical beam to at least 10 nanometers through a nonlinear effect in the nonlinear element to form the output optical beam with an output beam broadened spectrum. At least a portion of the output beam broadened spectrum comprises a near-infrared wavelength between 600 nanometers and 1000 nanometers, and the output optical beam is modulated at a modulation frequency. The system includes an interface device configured to receive a received portion of the output optical beam and configured to deliver a delivered portion of the output optical beam to a tissue sample, wherein the interface device comprises a monochromator configured to receive at least a portion of the received portion of the output optical beam and to form a filtered optical beam as the delivered portion of the output optical beam, and a receiver configured to receive at least a portion of a diffuse spectroscopy output beam from the tissue sample that results from light diffusion of the delivered portion of the output optical beam into a top two (2) millimeters or more of the tissue sample, wherein the receiver is configured to process the portion of the spectroscopy output beam to generate an output signal that monitors absorption or scattering features of the tissue sample, wherein the receiver is configured to use a lock-in technique that detects the modulation frequency.

In one embodiment, a diagnostic system comprises a light source configured to generate an output optical beam, comprising: one or more semiconductor sources configured to generate an input beam; one or more optical amplifiers configured to receive at least a portion of the input beam and to deliver an intermediate beam to an output end of the one or more optical amplifiers; one or more optical fibers configured to receive at least a portion of the intermediate beam and to deliver at least the portion of the intermediate beam to a distal end of the one or more optical fibers to form a first optical beam; and a nonlinear element configured to receive at least a portion of the first optical beam and to broaden a spectrum associated with the at least a portion of the first optical beam to at least 10 nanometers through a nonlinear effect in the nonlinear element to form the output optical beam with an output beam broadened spectrum. At least a portion of the output beam broadened spectrum comprises a near-infrared wavelength between 600 nanometers and 1000 nanometers, and the output optical beam is modulated at a modulation frequency. The system includes an interface device configured to receive a received portion of the output optical beam and configured to deliver a delivered portion of the output optical beam to a tissue sample, and a receiver configured to receive at least a portion of a diffuse spectroscopy output beam that results from light diffusion of the delivered portion of the output optical beam into a top two (2) millimeters or more of the tissue sample, and configured to process the portion of the spectroscopy output beam to generate an output signal that monitors absorption or scattering by the tissue sample, wherein the receiver is configured to use a lock-in technique that detects the modulation frequency. The receiver is configured to: generate a first signal in response to light received while the light source is off; and generate a second signal in response to light received while the light source is on. The diagnostic system is configured to improve a signal-to-noise ratio of the diffuse spectroscopy output beam by differencing the first signal and the second signal.

In one embodiment, a diagnostic system includes a light source configured to generate an output optical beam comprising one or more semiconductor sources configured to generate an input beam, one or more optical amplifiers configured to receive at least a portion of the input beam and to deliver an intermediate beam to an output end of the one or more optical amplifiers, and one or more optical fibers configured to receive at least a portion of the intermediate beam and to deliver at least the portion of the intermediate beam to a distal end of the one or more optical fibers to form a first optical beam. A nonlinear element is configured to receive at least a portion of the first optical beam and to broaden a spectrum associated with the at least a portion of the first optical beam to at least 10 nanometers through a nonlinear effect in the nonlinear element to form the output optical beam with an output beam broadened spectrum, and wherein at least a portion of the output beam broadened spectrum comprises a short-wave infrared wavelength between approximately 1000 nanometers and approximately 1400 nanometers or between approximately 1600 nanometers and approximately 1800 nanometers, and wherein at least a portion of the one of more fibers is a fused silica fiber with a core diameter less than approximately 400 microns. An interface device is configured to receive a received portion of the output optical beam and to deliver a delivered portion of the output optical beam to a tissue sample, wherein the delivered portion of the output optical beam is configured to generate a spectroscopy output beam from the tissue sample, and wherein at least a part of the delivered portion of the output optical beam penetrates into the tissue sample a depth of two millimeters or more. A receiver is configured to receive at least a portion of the spectroscopy output beam having a bandwidth of at least 10 nanometers and to process the portion of the spectroscopy output beam to generate an output signal representing at least in part a composition of collagen and lipids in the tissue sample.

In another embodiment, a measurement system includes a light source configured to generate an output optical beam comprising a plurality of semiconductor sources configured to generate an input optical beam, a multiplexer configured to receive at least a portion of the input optical beam and to form an intermediate optical beam, and one or more fibers configured to receive at least a portion of the intermediate optical beam and to form the output optical beam, wherein the output optical beam comprises one or more optical wavelengths. An interface device is configured to receive a received portion of the output optical beam and to deliver a delivered portion of the output optical beam to a tissue sample, wherein the delivered portion of the output optical beam is configured to generate a spectroscopy output beam from the sample based on diffuse light spectroscopy, and wherein at least a part of the delivered portion of the output optical beam penetrates into the tissue sample a depth of two millimeters or more. A receiver is configured to receive at least a portion of the spectroscopy output beam and to process the portion of the spectroscopy output beam to generate an output signal, wherein the output signal is based on a chemical composition of the tissue sample.

In yet another embodiment, a method of measuring includes generating an output optical beam comprising generating an input optical beam from a plurality of semiconductor sources, multiplexing at least a portion of the input optical beam and forming an intermediate optical beam, and guiding at least a portion of the intermediate optical beam and forming the output optical beam, wherein the output optical beam comprises one or more optical wavelengths, wherein at least a portion of the optical wavelengths is between approximately 1000 nanometers and 1400 nanometers or between approximately 1600 nanometers and 1800 nanometers. The method may also include receiving a received portion of the output optical beam and delivering a delivered portion of the output optical beam to a tissue sample and generating a spectroscopy output beam having a bandwidth of at least 10 nanometers from the tissue sample. The method may further include receiving at least a portion of the spectroscopy output beam, and processing the portion of the spectroscopy output beam and generating an output signal based on a wavelength dependence of the spectroscopy output beam over the bandwidth of at least 10 nanometers, and wherein the output signal is based on a chemical composition of the tissue sample.

BRIEF DESCRIPTION OF THE DRAWINGS

For a more complete understanding of the present disclosure, and for further features and advantages thereof, reference is now made to the following description taken in conjunction with the accompanying drawings, in which:

FIG. 7A illustrates logarithm of the inverse of reflection spectra; and FIG. 7B illustrates second derivative spectra.

FIG. 16A illustrates renal arteries with no laser exposure. FIG. 16B illustrates renal arteries after focused laser exposure, with the laser light near 1708 nm.

FIG. 23A illustrates high power SWIR-SC lasers that may generate light between approximately 1.4-1.8 microns.

FIG. 23B illustrates high power SWIR-SC lasers that may generate light between approximately 2-2.5 microns.

DETAILED DESCRIPTION

As required, detailed embodiments of the present disclosure are described herein; however, it is to be understood that the disclosed embodiments are merely exemplary of the disclosure and may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Figure 1:
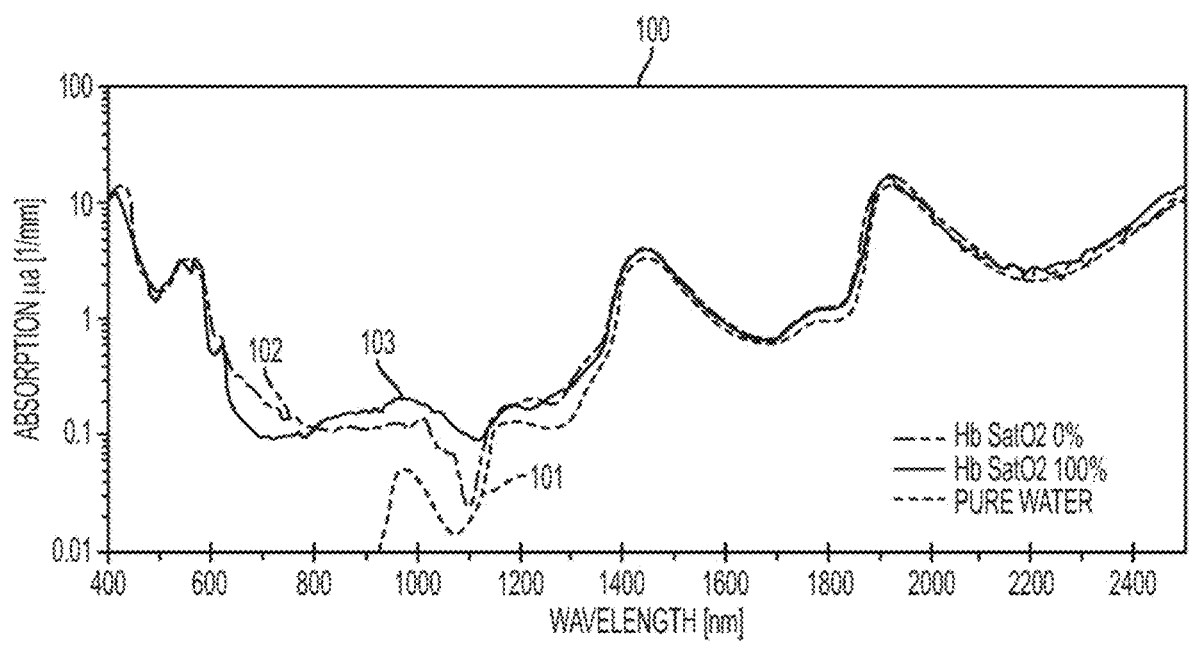
FIG. 1 illustrates the optical absorption of pure water, hemoglobin without oxygen, and hemoglobin saturated with oxygen.

To perform non-invasive optical mammography, one desired attribute is that the light may penetrate as far as possible into the breast tissue. In diffuse reflection spectroscopy, a broadband light spectrum may be emitted into the tissue, and the spectrum of the reflected or transmitted light may depend on the absorption and scattering interactions within the target tissue. Since breast tissue has significant water and hemoglobin content, it is valuable to examine the wavelength range over which deep penetration of light is possible. FIG. 1 illustrates the optical absorption 100 of pure water (dotted line) 101, hemoglobin without oxygen (thinner solid line) 102, and hemoglobin saturated with oxygen (thicker solid line) 103. It can be noted that above about 1100 nm, the absorption of hemoglobin is almost the same as water absorption. The penetration depth may be proportional to the inverse of the optical absorption. Therefore, the highest penetration depth will be at the absorption valley, approximately in the wavelength range between about 900 nm and about 1300 nm. Although not as low in absorption compared to the first window, another absorption valley lies between about 1600 nm and 1800 nm. Thus, non-invasive imaging preferably should use wavelengths that fall in one of these two absorption valleys.

Figure 2:
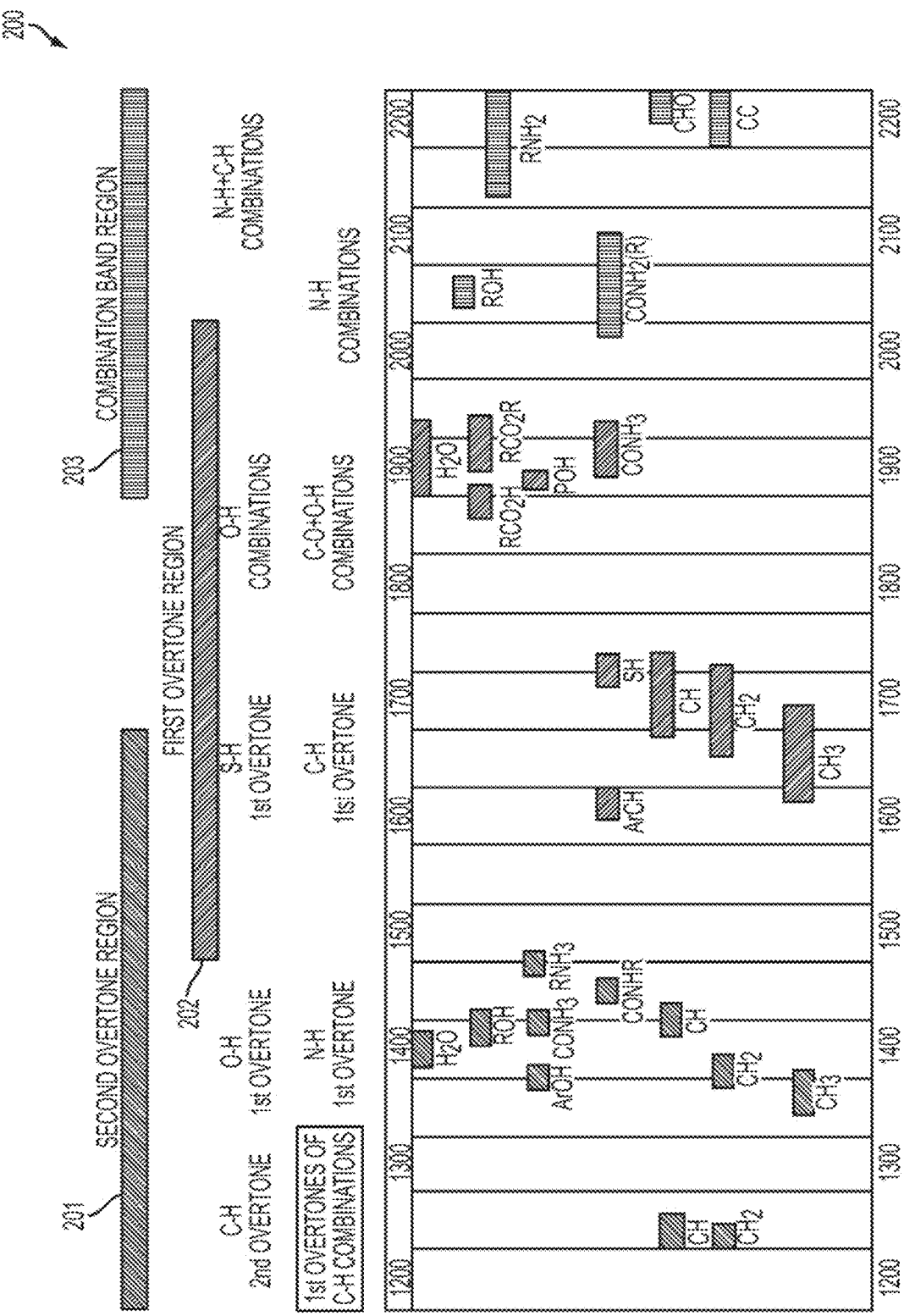
FIG. 2 shows examples of various absorption bands of chemical species in the wavelength range between about 1200-2200 nm.

FIG. 2 shows examples of various absorption bands of chemical species 200 in the wavelength range between about 1200 nm and 2200 nm. Although the fundamental absorptions usually lie in the mid-infrared (e.g., wavelengths longer than about 3 microns), there are many absorption lines in the NIR corresponding to the second overtone region 201 between about 1000 nm and 1700 nm, the first overtone region 202 between about 1500 nm and 2050 nm, and the combination band region 203 between about 1900 nm and 2300 nm. As an example, hydrocarbon bonds common in many biological substances have their fundamental absorption in the mid-IR near 3300-3600 nm, but they also have many combination band lines between 2000-2500 nm, and other lines at shorter wavelengths corresponding to the first and second overtones. Fortunately, there are spectral features of FIG. 2 that overlap with the absorption valleys in FIG. 1. These are likely to be the wavelengths of interest for spectroscopic analysis of cancerous regions.

Figure 3:
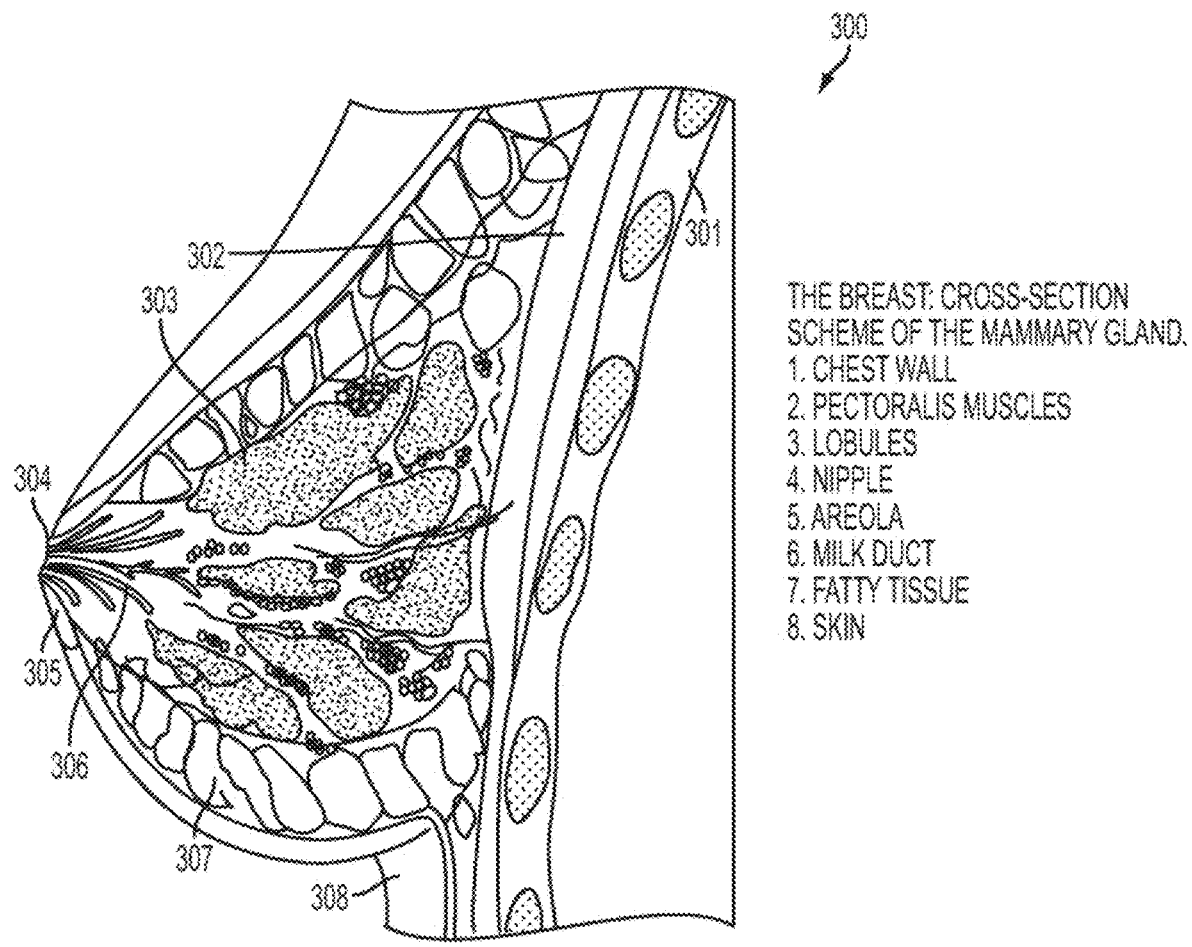
FIG. 3 depicts the structure of a female breast.

In women, the breasts (FIG. 3) 300 overlay the pectoralis major muscles 302 and cover much of the chest area and the chest walls 301. The breast is an apocrine gland that produces milk to feed an infant child; the nipple 304 of the breast is surrounded by an areola 305, which has many sebaceous glands. The basic units of the breast are the terminal duct lobules 303, which produce the fatty breast milk. They give the breast its function as a mammary gland. The lobules 303 feed through the milk ducts 306, and in turn these ducts drain to the nipple 304. The superficial tissue layer (superficial fascia) may be separated from the skin 308 by about 0.5-5 cm of adipose of fatty tissue 307.

Breast cancer is a type of cancer originating from breast tissue, most commonly from the inner lining of milk ducts 306, the lobules 303 that supply the ducts with milk, and/or the connective tissue between the lobules. Cancers originating from ducts 306 are known as ductal carcinomas, while those originating from lobules 303 or their connective tissue are known as lobular carcinomas. While the overwhelming majority of human cases occur in women, male breast cancer may also occur.

Figure 4:
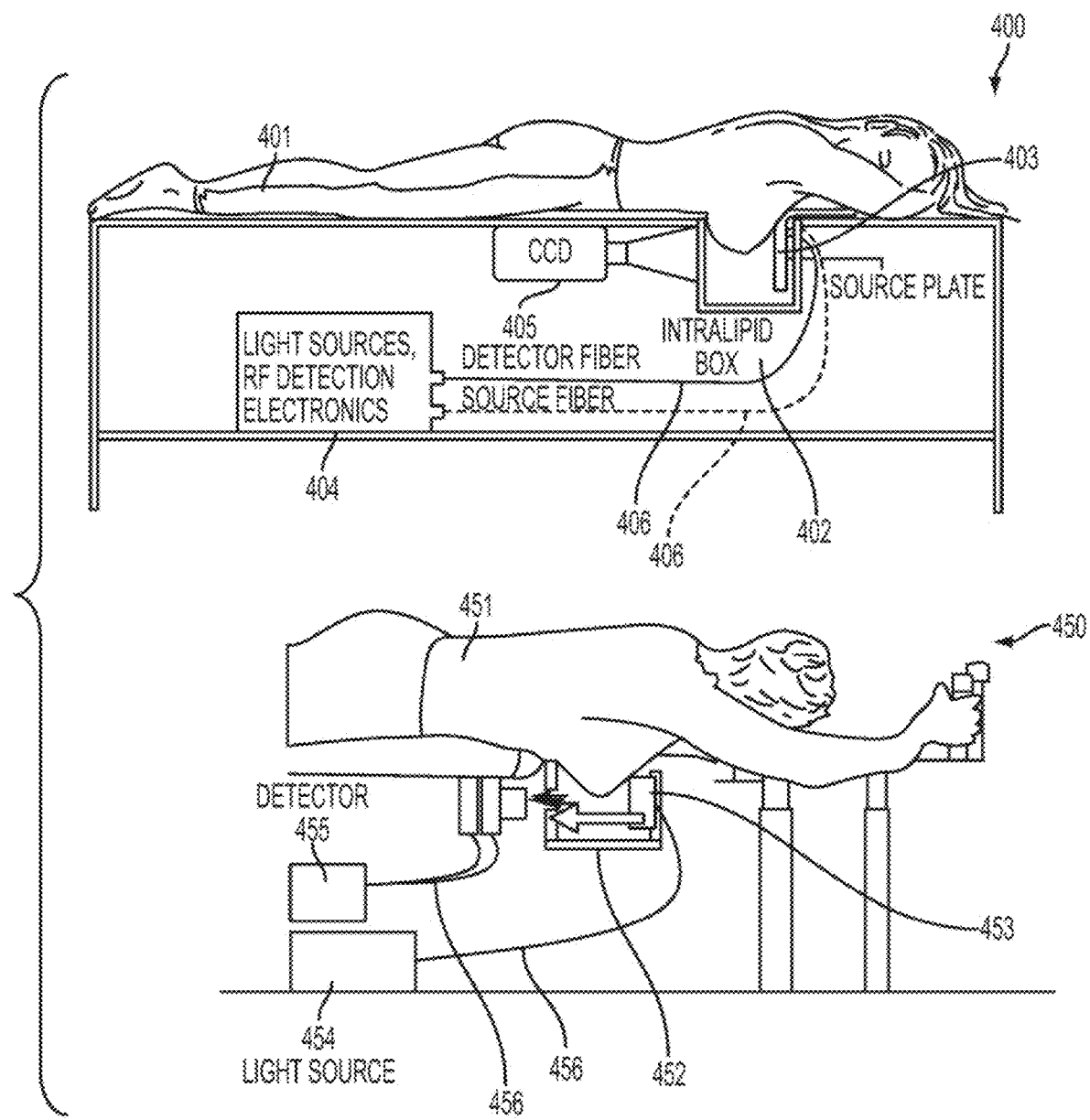
FIG. 4 illustrates particular embodiments of imaging systems for optically scanning a breast.

Several particular embodiments of imaging systems 400, 450 for optically scanning a breast are illustrated in FIG. 4. In these particular embodiments, the patient 401, 451 may lie in a prone position with her breasts inside a box 402, 452 with probably a transparent window on the detector side. A compression plate 403, 453 may hold the breast in place against the viewing window by mildly compressing the breast to a thickness between about 5.5 and 7.5 cm. The box 402, 452 may then be filled with a matching fluid with optical properties similar to human breast. In one instance, the matching fluid may comprise water, india ink for absorption, and a fat emulsion for scattering. The embodiments in FIG. 4 may also have one or more detectors 404, 455, one or more light sources 404, 454, various electronics, and even an imaging system based on charge coupled devices 405. As illustrated in FIG. 4, the light sources 404, 454 and detectors 404, 455 may be coupled to the box 402, 452 through one or more fibers 406, 456. Also, the imaging may be in reflection mode (top of FIG. 4), transmission mode (bottom of FIG. 4), or some combination.

Beyond the geometry and apparatus of FIG. 4, the optical imaging system may use one or more of three different illumination methods: continuous wave, time-domain photon migration, and frequency-domain photon migration. In one embodiment, continuous-wave systems emit light at approximately constant intensity or modulated at low frequencies, such as 0.1-100 kHz. In another embodiment, the time-domain photon migration technique uses relatively short, such as 50-400 psec, light pulses to assess the temporal distribution of photons. Since scattering may increase the times of flight spent by photons migrating in tissues, the photons that arrive earliest at the detector probably encountered the fewest scattering events. In yet another embodiment, the frequency-domain photon migration devices modulate the amplitude of the light that may be continuously transmitted at relatively high frequencies, such as 10 MHz to 1 GHz. For example, by measuring the phase shift and amplitude decay of photons as compared to a reference signal, information may be acquired on the optical properties of tissue, and scattering and absorption may be distinguished. Beyond these three methods, other techniques or combinations of these methods may be used, and these other methods are also intended to fall within the scope of this disclosure.

Although particular embodiments of imaging architectures are illustrated in FIG. 4, other system architectures may also be used and are also intended to be covered by this disclosure. For example, in one embodiment several couples of optical fibers for light delivery and collection may be arranged along one or more rings placed at different distances from the nipple 304. In an alternate embodiment a "cap" with fiber leads for light sources and detectors may be used that fits over the breast. In yet another embodiment, imaging optics and light sources and detectors may surround the nipple 304 and areola 305 regions of the breast. As yet another alternative, a minimally invasive procedure may involve inserting needles with fiber enclosure (to light sources and detectors or receivers) into the breast, so as to probe regions such as the lobules 303 and connective tissue. Both non-invasive and minimally invasive optical imaging methods are intended to be covered by this disclosure.

Optical Wavelength Ranges for Cancer Detection

Figure 5:
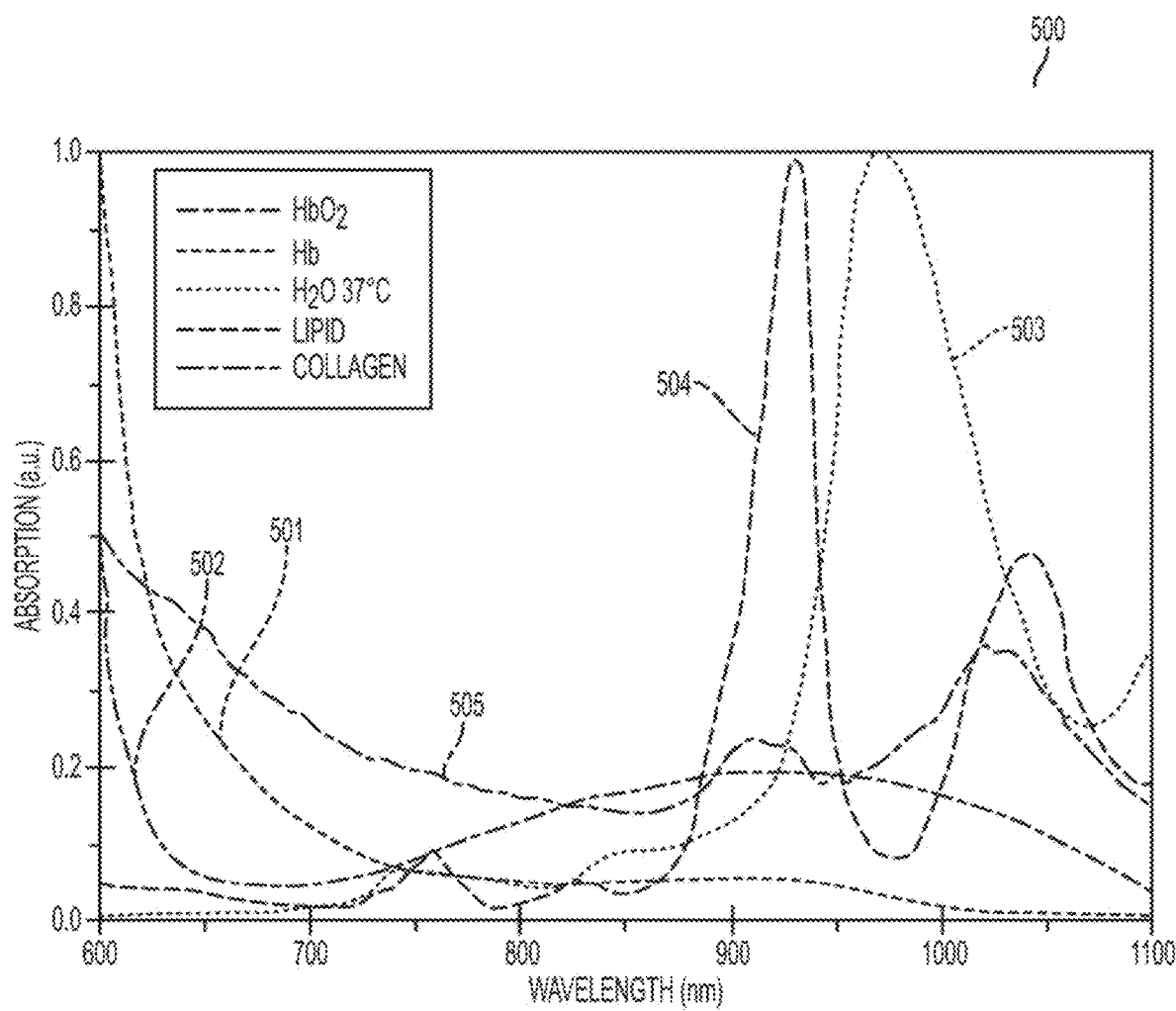
FIG. 5 shows the normalized absorption spectra of main tissue absorbers in the NIR for breast cancer, between about 600-1100 nm.

Many of the diffuse optical tomography studies previously conducted have relied on using NIR in the wavelength range of about 600-1000 nm, where light absorption at these wavelengths may be minimal, allowing for sufficient tissue penetration (up to 15 cm). In these wavelength ranges, it has been claimed that concentrations of oxy- and deoxy-hemoglobin, water, and lipids can be determined. For example, FIG. 5 shows the normalized absorption spectra 500 of main tissue absorbers in the NIR between about 600 nm and 1100 nm: deoxy-hemoglobin, Hb, 501, oxy-hemoglobin, $HbO_2$, 502, water 503, lipids 504 and collagen 505. It is speculated that in a malignant tumor, hemoglobin concentration may be directly related to angiogenesis, one of the main factors required for tumor growth and metastases. Moreover, the proportions of oxy- and deoxy-hemoglobin in a tumor may change due to its metabolism. Thus, by measuring concentrations of the breast components, discrimination of benign and malignant tumors may be possible with diffuse optical imaging. Experiment evidence suggests that cancerous tissue is associated with higher hemoglobin and water concentrations, and a lower lipid concentration with respect to normal breast tissue.

Based on FIG. 1 and the dynamics of carcinoma, it may be advantageous to perform spectroscopy in longer wavelengths, such as windows between 1000-1400 nm or 1600-1800 nm. For example, looking at the absorption curves 100 in FIG. 1, the absorption between approximately 1000-1300 nm may be comparable to the 600-1000 nm window described in FIG. 5. However, the loss through the soft tissue medium (penetration depth may be inversely related to the loss) will be due to absorption and scattering. In fact, the scattering properties of tissue may also contain valuable information for lesion diagnosis. Since the scattering is inversely proportional to some power of wavelength (for example, in some tissue scattering is inversely proportional to the wavelength cubed), the scattering contribution to the loss may decrease at longer wavelengths. Moreover, these longer wavelength windows may contain diagnostic information on content of collagen and adipose, both of which may be significant indicators for breast cancer.

Figure 6:
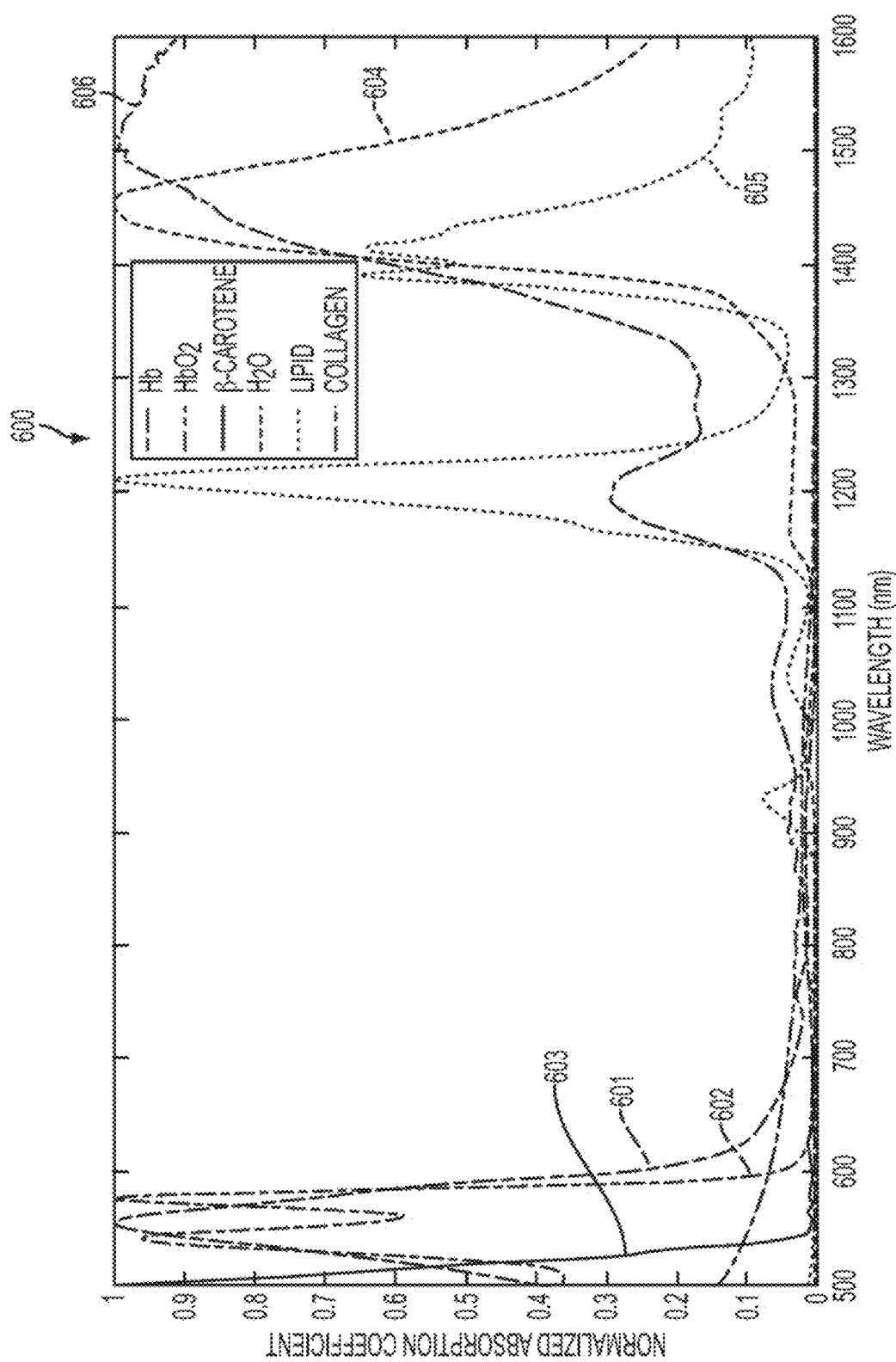
FIG. 6 illustrates the normalized absorption coefficient in the wavelength range between about 500-1600 nm for many of the components of breast tissue.

Breast cancer spectroscopy may benefit from the use of wavelengths longer than about 1000 nm for a number of reasons. As one example, the main absorbers in soft tissues of the visible spectrum of light may be oxy- and deoxygenated hemoglobin and beta-carotene. On the other hand, primary absorbers in the near-infrared spectrum of light may be water, adipose tissue and collagen. Particularly adipose and collagen content may be valuable for early detection of cancers. In one embodiment, increased levels of collagen in breast malignancies are thought to be due to increased vascularity of the tumors. Collagen type I may be an important component of artery walls. FIG. 6 illustrates the normalized absorption coefficient 600 in the wavelength range between about 500 nm and 1600 nm for Hb 601, $HbO_2$ 602, beta-carotene 603, water 604, lipid 605 and collagen 606.

Collagen and Adipose Signatures in Near-Ir

Examining the collagen content may be a valuable indicator for breast cancer detection. Collagen is one of the important extracellular matrix proteins, and fibrillar collagens help to determine stromal architecture. In turn, changes in the stromal architecture and composition are one of the aspects of both benign and malignant pathologies, and, therefore, may play an initial role in breast carcinogenesis. For example, collagen seems to be related to cancer development, because high mammographic density may be recognized as a risk factor for breast cancer. Moreover, collagen type in high-risk dense breasts may appear to be different from collagen in low-density breasts.

Experimental data also shows that malignant mammary gland tissues of animals and humans show a decrease in lipids when compared to normal tissues. The reduced amounts of lipids in the cancerous sites may be caused by a high metabolic demand of lipids in the malignant tumors. For example, due to the rapid proliferation of cancerous cells, there may be reduced lipid content in cancerous tissues. Thus, in addition to collagen, another valuable marker for breast cancer may be the lipid spectral features. It may also be possible to combine the markers from oxy- and deoxygenated hemoglobin and water with lipid and collagen lines to improve the diagnostics and/or therapeutics of optical imaging and/or treatment for breast and other types of cancer. Although specific examples of tissue constituents are discussed, other tissue constituents and related markers may also be associated with breast cancer and other cancers, and these other constituents are also intended to be covered by this disclosure.

Figure 7A:
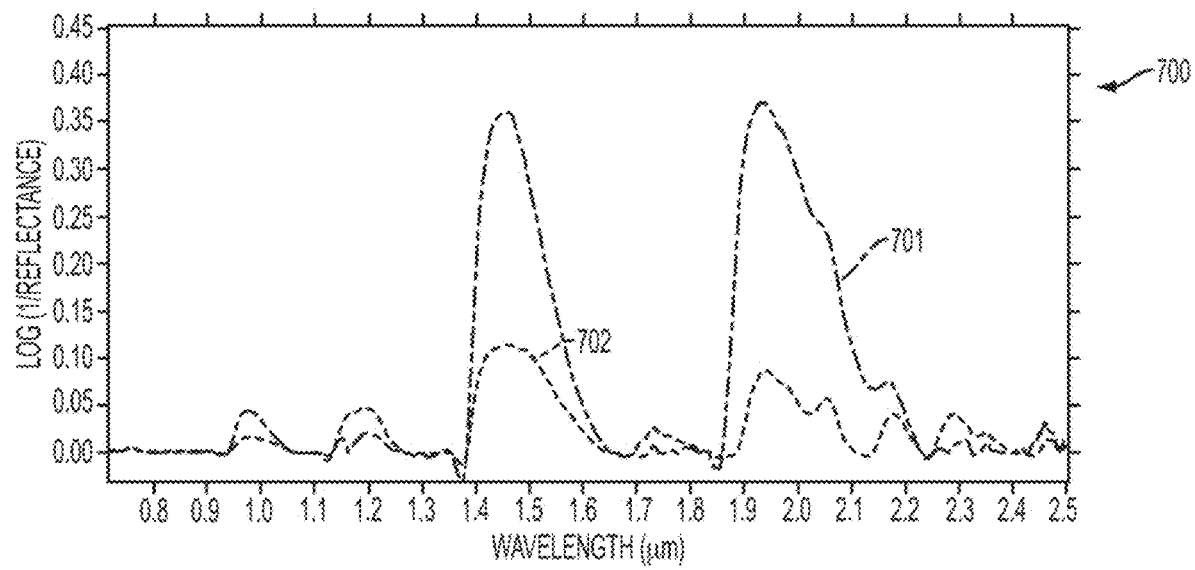
FIGS. 7A and 7B show the typical spectra of the cancerous site of a treated rat and the corresponding site of a normal rat.
Figure 7B:
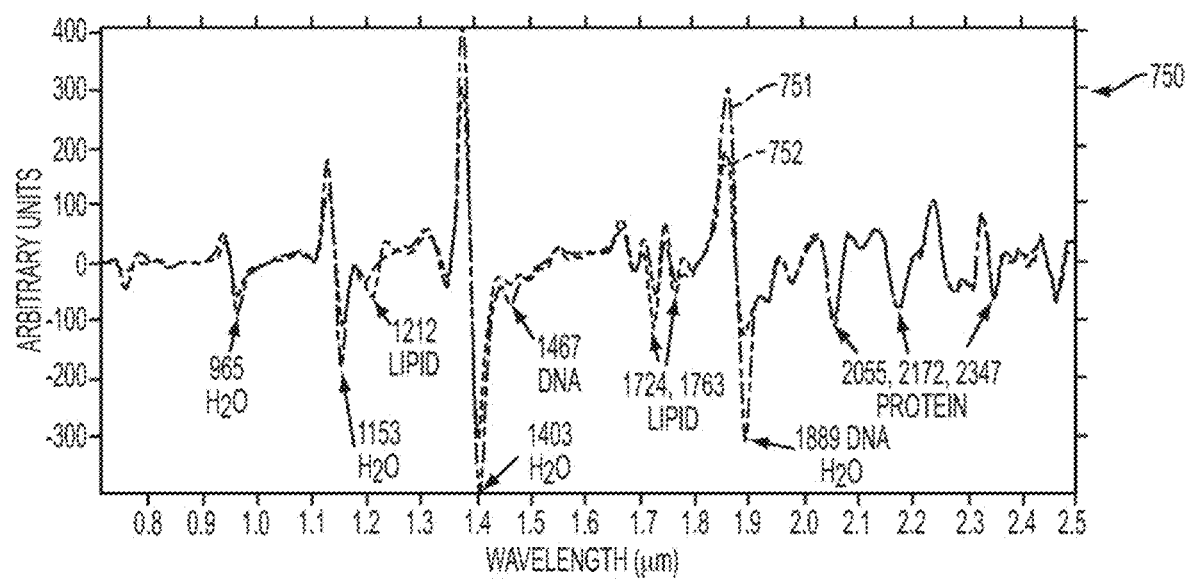

As an example of the types of spectral signatures that may exist, in vivo investigations of progressive changes in rat mammary gland tumors were conducted using near-infrared spectroscopy with a Fourier-transform infrared spectrometer. In one embodiment, FIG. 7 shows the typical spectra of the cancerous site of the treated rat and the corresponding site of the normal rat. FIG. 7A shows the logarithm of the inverse of reflection spectra 700, while FIG. 7B shows their second derivative spectra 750. The curves 701, 751 correspond to the spectra of the cancerous sites, while 702, 752 correspond to the spectra of the normal sites. Since the second derivative techniques may be useful in the analyses of NIR spectra to minimize baseline offsets and to resolve overlapping absorption without compromising signal-to-noise, FIG. 7B may be used for interpretation of the spectral changes.

In FIG. 7B identification may be made of several of the spectral features. In particular, there are DNA bands near 1471 nm and 1911 nm, while there are water bands near 967 nm, 1154 nm, 1402 nm, and 1888 nm. Moreover, there are lipid bands near 1209 nm, 1721 nm and 1764 nm, and there are protein bands near 2055 nm, 2172 nm and 2347 nm. The NIR spectra of FIG. 7 show that the DNA and water contents in the cancerous tissue may be higher than those in normal tissues. On the other hand, the lipid content in the cancerous tissue may be less than the lipid content in normal tissues. With protein contents, however, little difference may be found between the normal and cancerous tissue.

Figure 8:
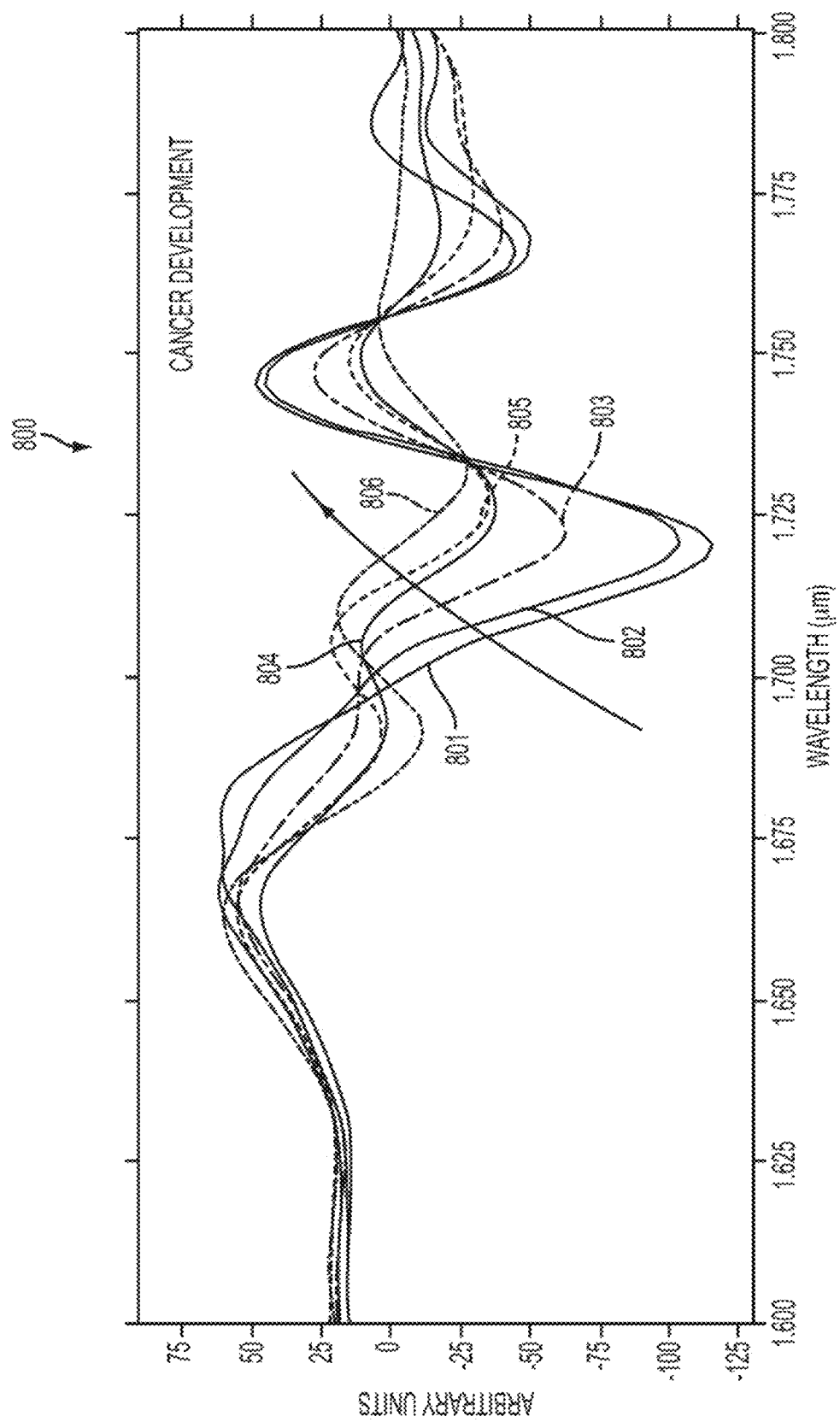
FIG. 8 shows the second derivative of spectral changes over several weeks between about 1600-1800 nm in rats with breast cancer.

These experiments on rats with breast cancer were also used to observe the temporal progression of the cancer. In this embodiment, as the cancer grew, the lipid band intensity decreased, and this band also shifted to higher wavelengths, and collagen peaks appeared in the tissues. In FIG. 8, the second derivative spectral changes 800 were investigated in the 1600 nm to 1800 nm wavelength range over several weeks. An early cancer was detected in the $5^{th}$ week, and then it grew rapidly from the $6^{th}$ 801 to the $7^{th}$ 802 week. The cancer's temporal progression through the $8^{th}$ 803, $9^{th}$ 804, $10^{th}$ 805 and $11^{th}$ 806 week are shown in the various curves in FIG. 8. With the cancer growth, the intensity of the lipid band in the vicinity of 1721 nm decreased, and this band shifted to higher wavelengths by 7 nm at the $11^{th}$ week 806 compared to the wavelength band at the $5^{th}$ week. The higher wavelength shift may indicate that an order parameter of the lipids increases with progressive cancer growth.

Figure 11:
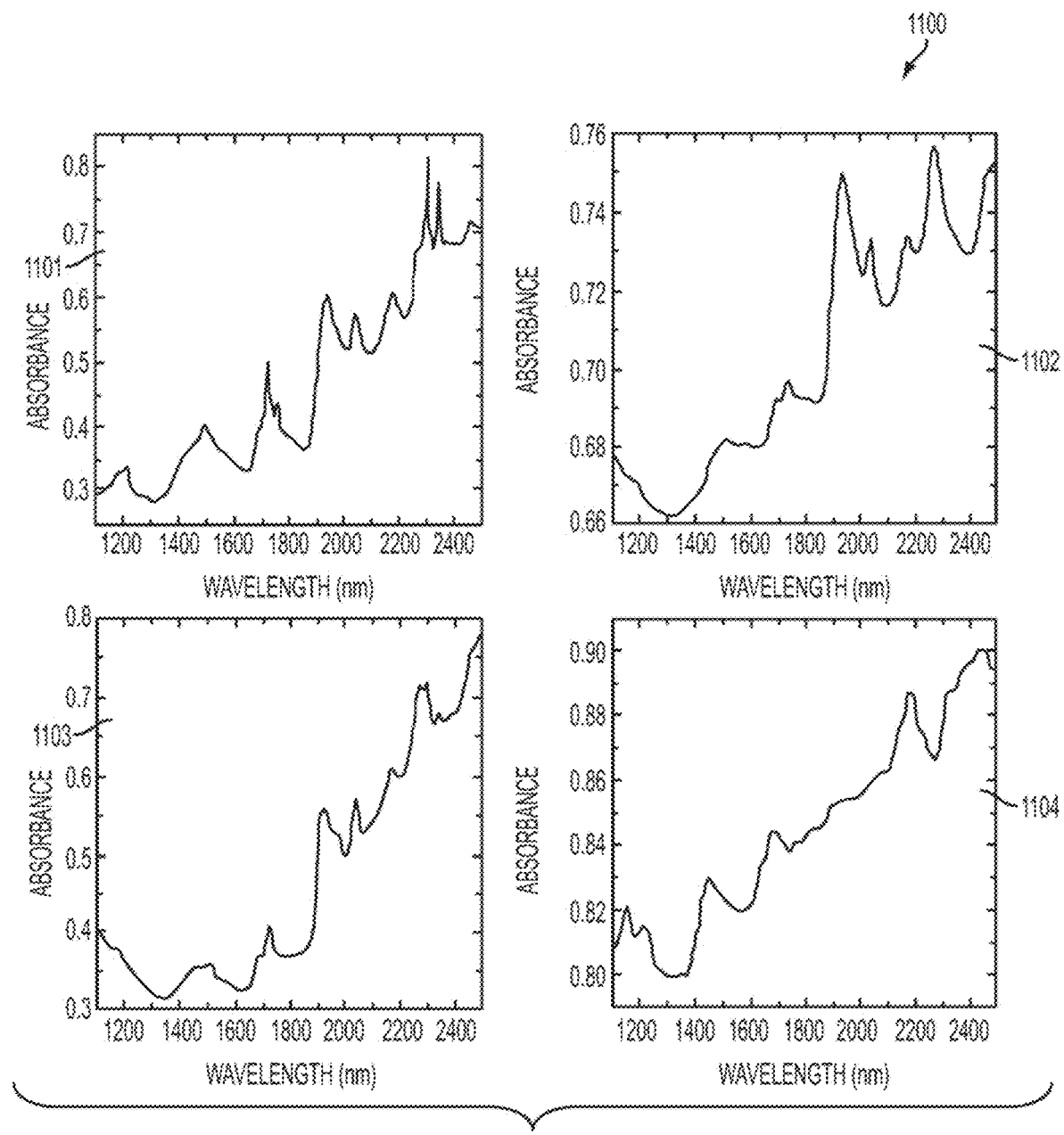
FIG. 11 illustrates the absorbance for four types of collagen: collagen I, collagen II, collagen III, and collagen IV.

Moreover, in the data of FIG. 8 is seen that a new peak appeared as the cancer grew around 1690 nm, which may be assigned to be a collagen absorption by comparison with the absorptions of standard collagen (c.f., FIG. 11). The higher wavelength shift may be attributable to the formation of elastic fibers in the lipid layer with collagen induced in the cancer tissues, thus leading to an increased order parameter of the lipids. Thus, it can be seen that significant information about breast cancer tissue compared with normal tissue may be obtained by spectroscopy at the longer wavelengths in the near-infrared.

Figure 9:
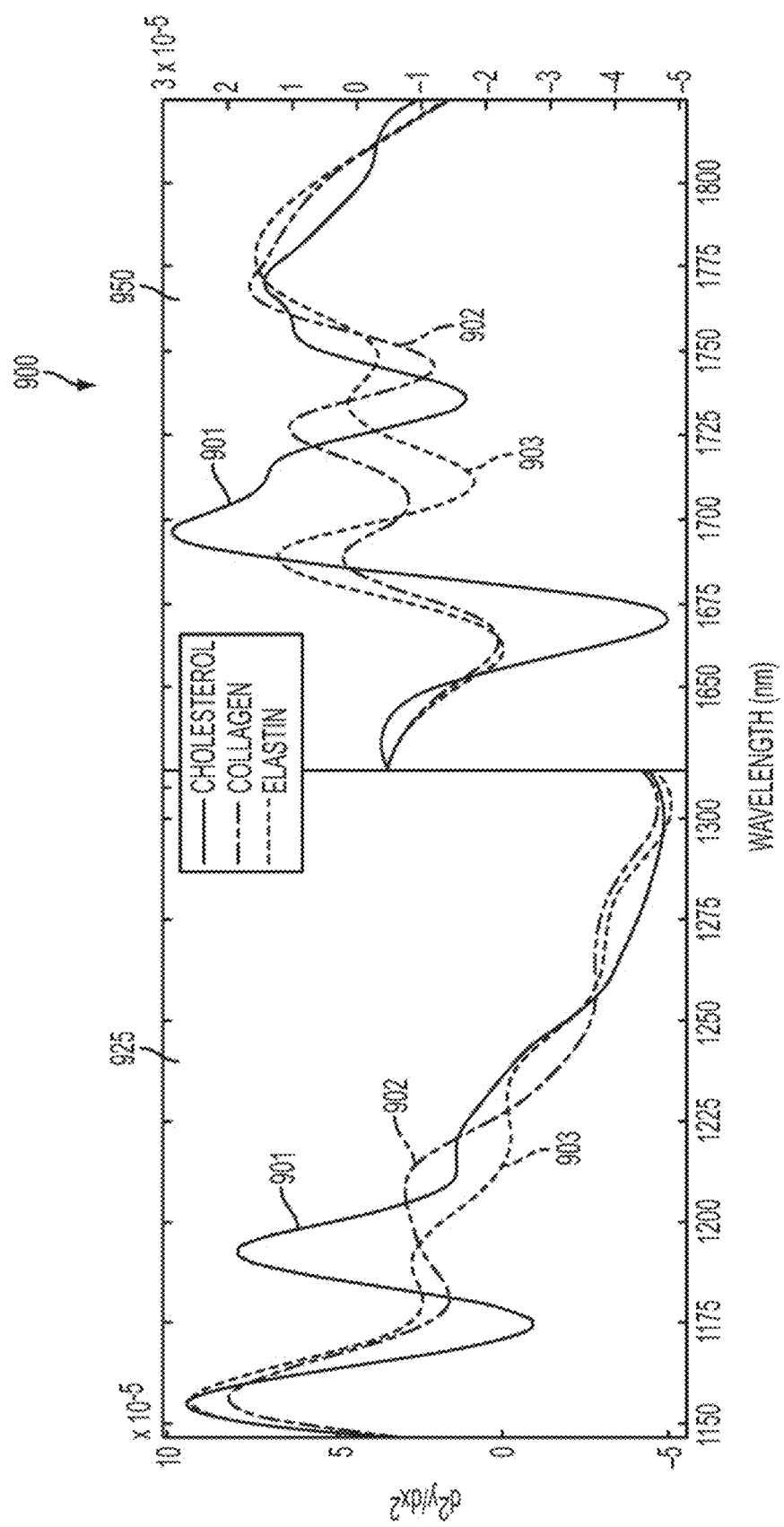
FIG. 9 illustrates the second derivative spectra for cholesterol, collagen and elastin.

The second derivative spectra may also be insightful for observing and monitoring changes in tissue as well as characterizing tissue in the near-infrared wavelength range. As an example, FIG. 9 illustrates the second derivative spectra 900 for cholesterol (similar to one embodiment of lipids) 901, collagen 902, and elastin 903. The left curve 925 shows the second derivative data over the wavelength range of about 1150 nm to 1300 nm, while the right curve 950 shows the second derivative data over the wavelength range of about 1600 nm to 1850 nm. These wavelengths show numerous features for cholesterol/lipid 901, collagen 902, and elastin 903, which again emphasizes the added value of using wavelengths longer than about 1000 nm for cancer diagnostics.

Figure 10:
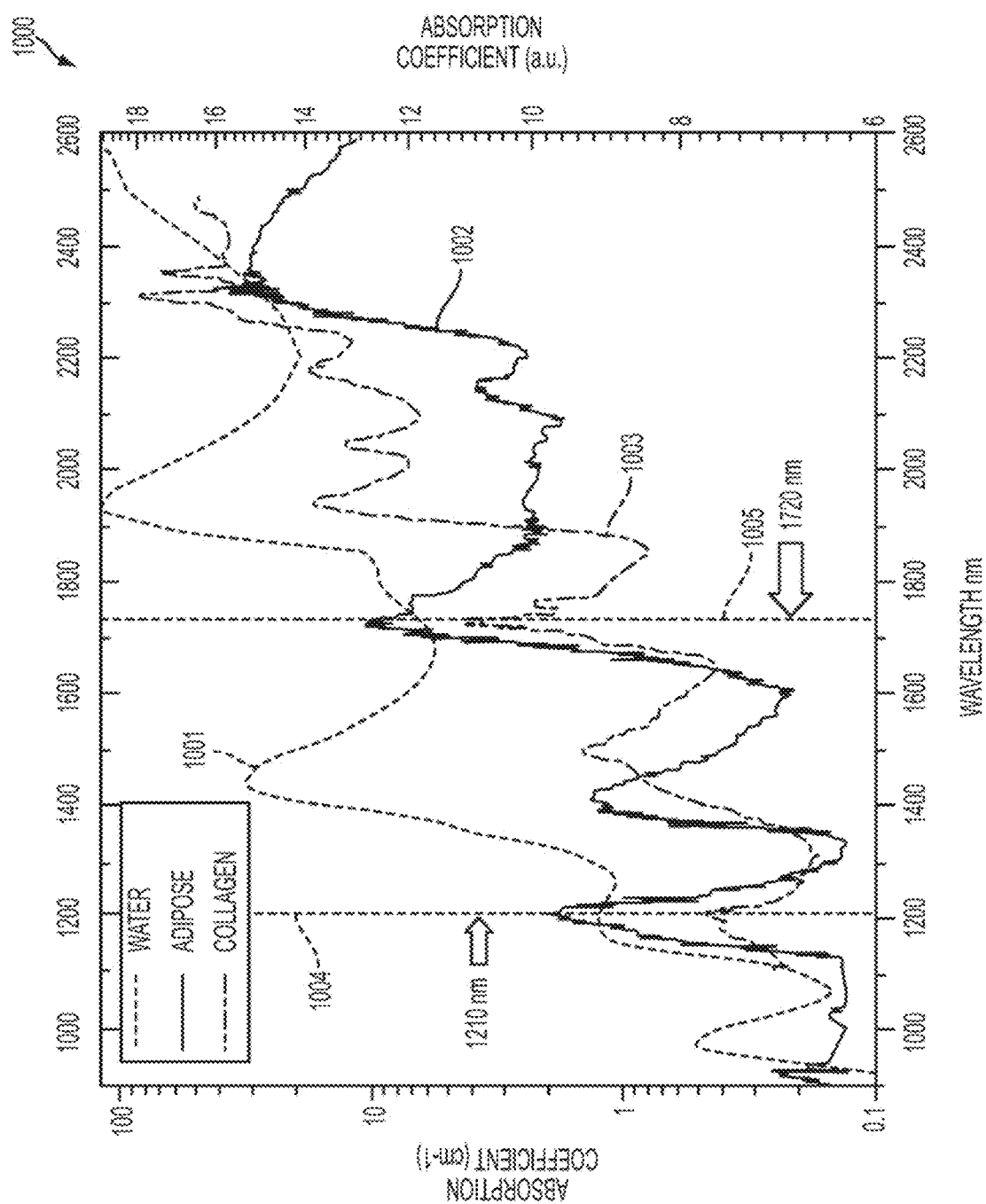
FIG. 10 shows the absorption coefficient as a function of wavelength between about 1000 nm and 2600 nm for water, adipose and collagen.

To further illustrate the value of using longer wavelengths in the NIR or SWIR for observing changes in breast cancer and other cancer markers, the spectra of in water, lipids/adipose and collagen of different varieties may be studied. As one embodiment, the absorption coefficients 1000 are shown in FIG. 10 as a function of wavelength between about 1000 nm and 2600 nm. FIG. 10 overlaps the absorption coefficient for water 1001, adipose 1002 (forms of adipose include fatty tissue and acids, lipids, and cholesterol), and collagen type I 1003. One may note that particular absorption peaks for adipose 1002 and collagen type I 1003 align at wavelengths near 1210 nm 1004 and 1720 nm 1005, which also correspond to local minima in water absorption.

Moreover, the NIR spectra for collagen also depend on the type of collagen. As an example, FIG. 11 illustrates the absorbance 1100 for four types of collagen: collagen I 1101, collagen II 1102, collagen III 1103, and collagen IV 1104. Collagen I, for instance, may be a major constituent of stroma. Also, collagen I and collagen III may be the principal collagens of the aorta. Since the spectra of the four collagens are distinctive, multicomponent analysis of collagens may possibly be used to distinguish the type of collagen involved.

The experimental results discussed thus far indicate that breast cancer detection may benefit from spectroscopy in the NIR and SWIR, particularly wavelengths between approximately 1000-1400 nm and 1600-1800 nm. These are wavelength windows that may have deep penetration into soft tissue, while still falling within lower absorption valleys of water. Moreover, the longer wavelengths lead to less scattering in tissue and water, again permitting deeper penetration of the light. In the NIR and SWIR wavelength range, the spectra of standard samples of cholesterol, protein, collagen, elastin and DNA were measured to obtain information on their characteristic bands in the spectra of mammary gland tissues. Absorption peaks in the standard samples occur at the following exemplary wavelengths:

Collagen: 1182 nm, 1360 nm, 1426 nm, 1496 nm, 1569 nm, 1690 nm, 1732 nm;
Lipids: 1157 nm, 1209 nm, 1404 nm, 1721 nm, 1764 nm;
Cholesterol: 918 nm, 1195 nm, 1376 nm, 1585 nm, 1711 nm, 1757 nm;
Protein: 910 nm, 1143 nm, 1186 nm, 1279 nm, 1420 nm, 1503 nm, 1579 nm, 1690 nm, 1739 nm, 1799 nm; and
DNA: 1414 nm, 1471 nm, 1626 nm, 1728 nm.

Comparing these absorption features with the data in FIGS. 6-11 shows that there are absorption features or signatures in the second derivatives that can be used to monitor changes in, for example, collagen and lipids. By using broadband light and performing spectroscopy in at least some part of the wavelength windows between about 1000-1400 nm and/or 1600-1800 nm, the collagen and lipid changes, or other constituent changes, may be monitored. In one embodiment, for breast cancer the decrease in lipid content, increase in collagen content, and possible shift in collagen peaks may be observed by performing broadband light spectroscopy and comparing normal regions to cancerous regions as well as the absorption strength as a function of wavelength. The spectroscopy may be in transmission, reflection, diffuse reflection, diffuse optical tomography, or some combination. Also, this spectroscopy may be augmented by fluorescence data, if particular tags or markers are added. Beyond looking at the absorbance, the data processing may involve also observing the first, second, or higher order derivatives.

Broadband spectroscopy is one example of the optical data that can be collected to study breast cancer and other types of cancer. However, other types of spectral analysis may also be performed to compare the collagen and lipid features between different wavelengths and different tissue regions (e.g., comparing normal regions to cancerous regions), and these methods also fall within the scope of this disclosure. For example, in one embodiment just a few discrete wavelengths may be monitored to see changes in lipid and collagen contents. In a particular embodiment, wavelengths near 1200 nm may be monitored in the second derivative data of FIG. 9 to measure the cholesterol/lipid peak below 1200 nm in 901 versus the collagen peak above 1200 nm in 902. In yet another embodiment, the absorption features in FIG. 6 may be relied upon to monitor the lipid content 605 by measuring near 1200 nm and the collagen content 606 by measuring near 1300 nm. Although these embodiments use only two wavelengths, any number of wavelengths may be used and are intended to be covered by this disclosure.

Thus, a breast cancer monitoring system, or a system to monitor different types of cancers, may comprise broadband light sources and detectors to permit spectroscopy in transmission, reflection, diffuse optical tomography, or some combination. In one particular embodiment, high signal-to-noise ratio may be achieved using a fiber-based supercontinuum light source (described further herein). Other light sources may also be used, including a plurality of laser diodes, super-luminescent laser diodes, or fiber lasers.

Wavelength ranges that may be advantageous for cancer detection include the NIR and SWIR windows (or some part of these windows) between about 1000-1400 nm and 1600-1800 nm. These longer wavelengths fall within local minima of water absorption, and the scattering loss decreases with increasing wavelength. Thus, these wavelength windows may permit relatively high penetration depths. Moreover, these wavelength ranges contain information on the overtone and combination bands for various chemical bonds of interest, such as hydrocarbons.

These longer wavelength ranges may also permit monitoring levels and changes in levels of important cancer tissue constituents, such as lipids and collagen. Breast cancer tissue may be characterized by decreases in lipid content and increases in collagen content, possibly with a shift in the collagen peak wavelengths. The changes in collagen and lipids may also be augmented by monitoring the levels of oxy- and deoxy-hemoglobin and water, which are more traditionally monitored between 600-1000 nm. Other optical techniques may also be used, such as fluorescent microscopy.

To permit higher signal-to-noise levels and higher penetration depths, higher intensity or brightness of light sources may be used. With the higher intensities and brightness, there may be a higher risk of pain or skin damage. At least some of these risks may be mitigated by using surface cooling and focused infrared light, as further described herein.

Laser Experiments: Penetration Depth, Focusing, Skin Cooling

Some preliminary experiments show the feasibility of using focused infrared light for non-invasive procedures, or other procedures where relatively shallow vessels below the skin are to be thermally coagulated or occluded with minimum damage to the skin upper layers. In one embodiment, the penetration depth and optically induced thermal damage has been studied in chicken breast samples. Chicken breast may be a reasonable optical model for smooth muscle tissue, comprising water, collagen and proteins. Commercially available chicken breast samples were kept in a warm bath (~32 degree Celsius) for about an hour, and then about half an hour at room temperature in preparation for the measurements.

Figure 12:
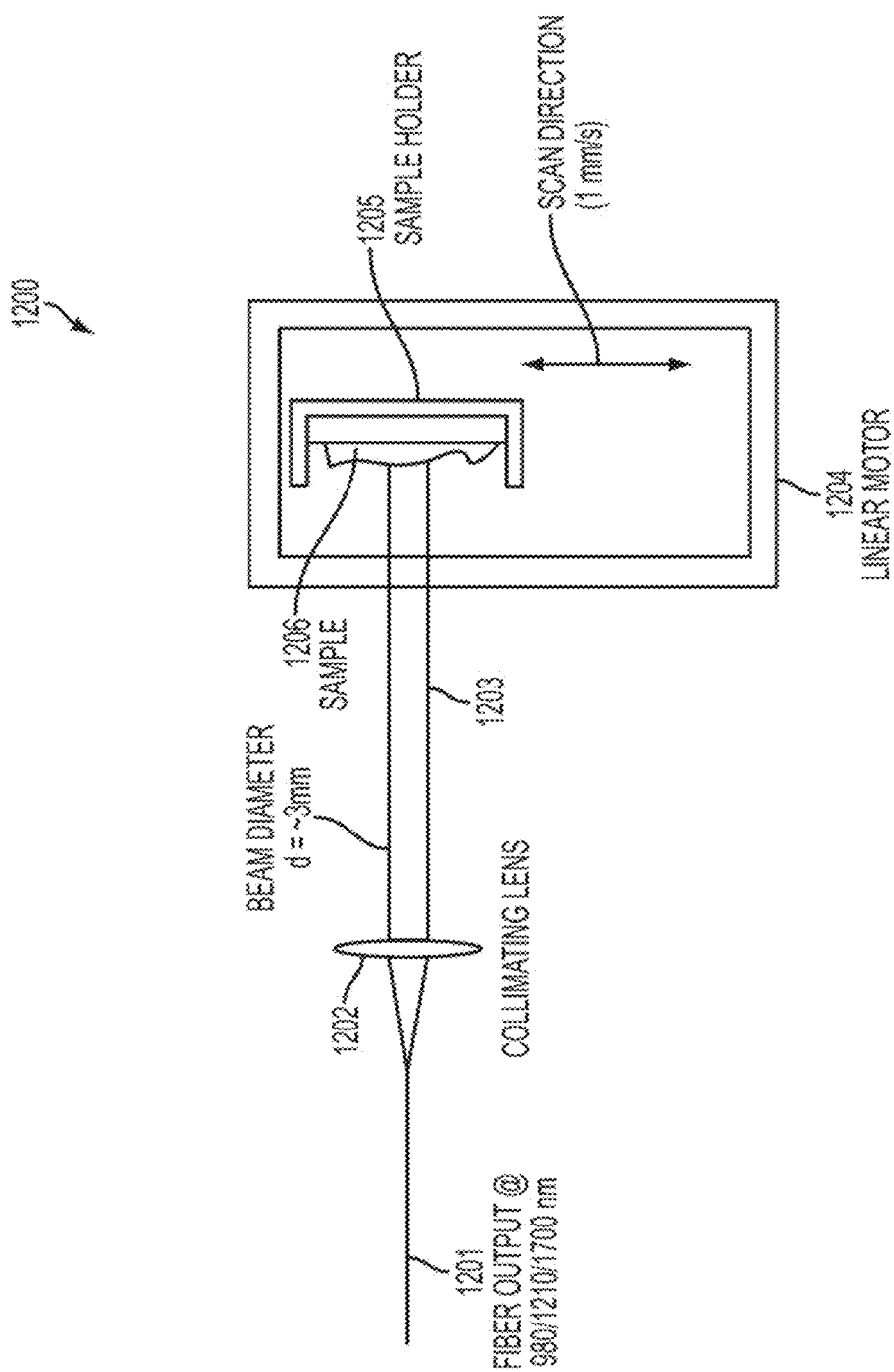
FIG. 12 shows an experimental set-up for testing chicken breast samples using collimated light. In this experiment, the collimated light has a beam diameter of about 3 mm.

An exemplary set-up 1200 for testing chicken breast samples using collimated light is illustrated in FIG. 12. The laser light 1201 near 980 nm, 1210 nm, or 1700 nm may be provided from one or more laser diodes or fiber lasers, as described further below. In this instance, laser diodes were used, which comprise a plurality of laser diode emitters that are combined using one or more multiplexers (particularly spatial multiplexers), and then the combined beam is coupled into a multi-mode fiber (typically 100 microns to 400 microns in diameter). The output from the laser diode fiber was then collimated using one or more lenses 1202. The resulting beam 1203 was approximately round with a beam diameter of about 3 mm. The beam diameter was verified by blade measurements (i.e., translating a blade across the beam). Also, the time-averaged power was measured in the nearly collimated section after the lens using a large power meter. The chicken breast samples 1206 were mounted in a sample holder 1205, and the sampler holder 1205 was mounted in turn on a translation stage 1204 with a linear motor that could move perpendicular to the incoming laser beam. Although particular details of the experiment are described, other elements may be added or eliminated, and these alternate embodiments are also intended to be covered by this disclosure.

Figure 13:
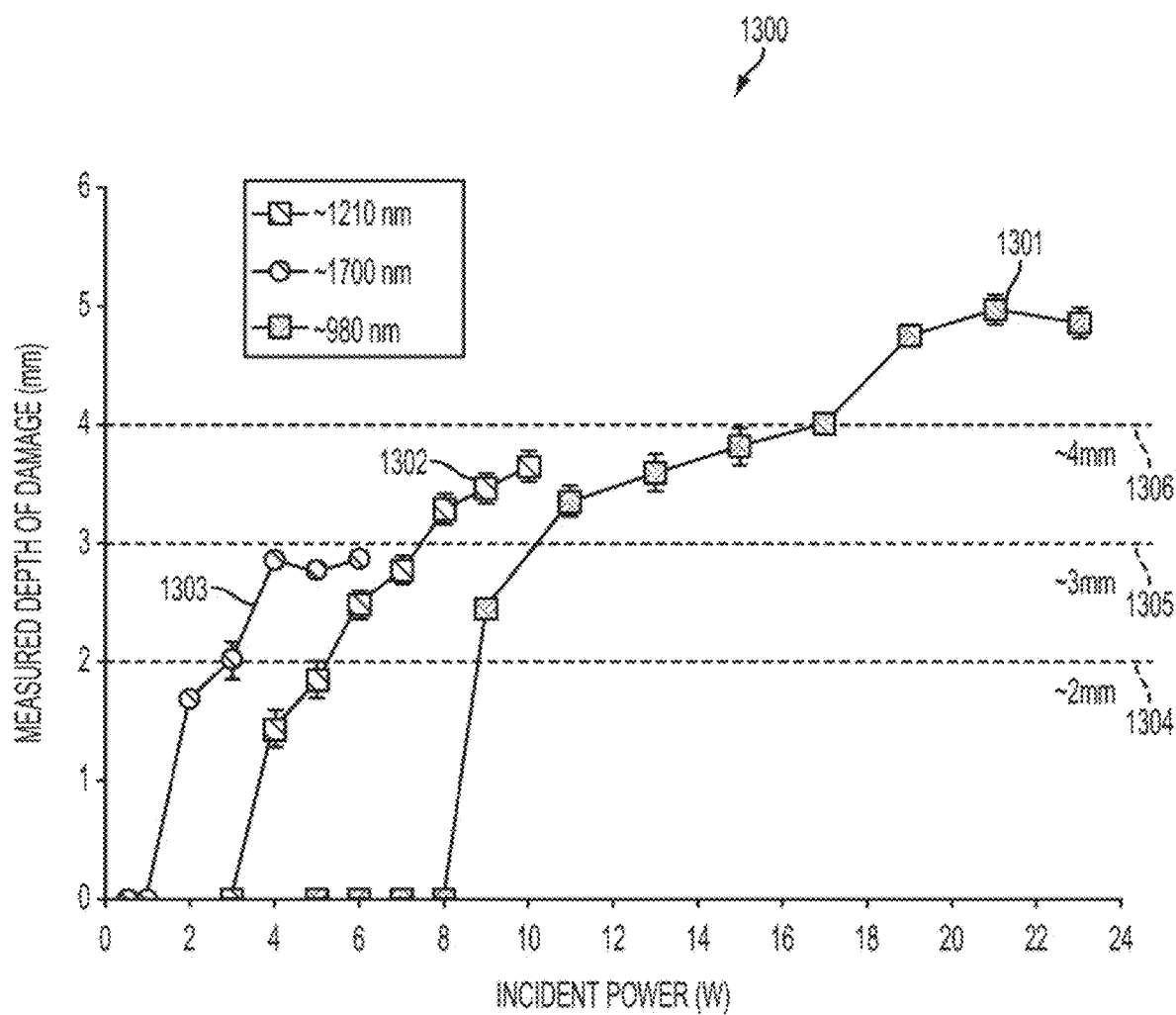
FIG. 13 plots the measured depth of damage (in millimeters) versus the time-averaged incident power (in Watts). Data is presented for laser wavelengths near 980 nm, 1210 nm and 1700 nm, and lines are drawn corresponding to penetration depths of approximately 2 mm, 3 mm, and 4 mm.

For these particular experiments, the measured depth of damage (in millimeters) versus the incident laser power (in Watts) is shown 1300 in FIG. 13. In this embodiment, laser diodes were used at wavelengths near 980 nm, 1210 nm and 1700 nm. The curve 1301 corresponds to about 980 nm, the curve 1302 corresponds to about 1210 nm, and the curve 1303 corresponds to about 1700 nm. It may be noted that there is a threshold power, above which the damage depth increases relatively rapidly. For example, the threshold power for wavelengths around 980 nm may be about 8 W, the threshold power for wavelengths around 1210 nm may be 3 W, and the threshold power for wavelengths around 1700 nm may be about 1 W. The threshold powers may be different at the different wavelengths because of the difference in water absorption (e.g., 1001 in FIG. 10). Part of the difference in threshold powers may also arise from the absorption of proteins such as collagen (e.g., 1003 in FIG. 10). After a certain power level, the damage depth appears to saturate: i.e., the slope flattens out as a function of increasing pump power.

In one embodiment, if the penetration depth is defined as the depth where damage begins to approximately saturate, then for wavelengths of about 980 nm 1301 the penetration depth 1306 may be defined as approximately 4 mm, for wavelengths of about 1210 nm 1302 the penetration depth 1305 may be defined as approximately 3 mm, and for wavelengths of about 1700 nm 1303 the penetration depth 1304 may be defined as approximately 2 mm. These are only approximate values, and other values and criteria may be used to define the penetration depth. It may also be noted that the level of damage at the highest power points differs at the different wavelengths. For example, at the highest power point of 1303 near 1700 nm, much more damage is observed, showing evidence of even boiling and cavitation. This may be due to the higher absorption level near 1700 nm (e.g., 1001 in FIG. 10). On the other hand, at the highest power point 1301 near 980 nm, the damage is not as catastrophic, but the spot size appears larger. The larger spot size may be due to the increased scattering at the shorter wavelengths (e.g., 1001 in FIG. 10). Based on data 1300 such as in FIG. 13, it may be possible to select the particular wavelength for the laser beam to be used in the non-invasive procedure.

Figure 14:
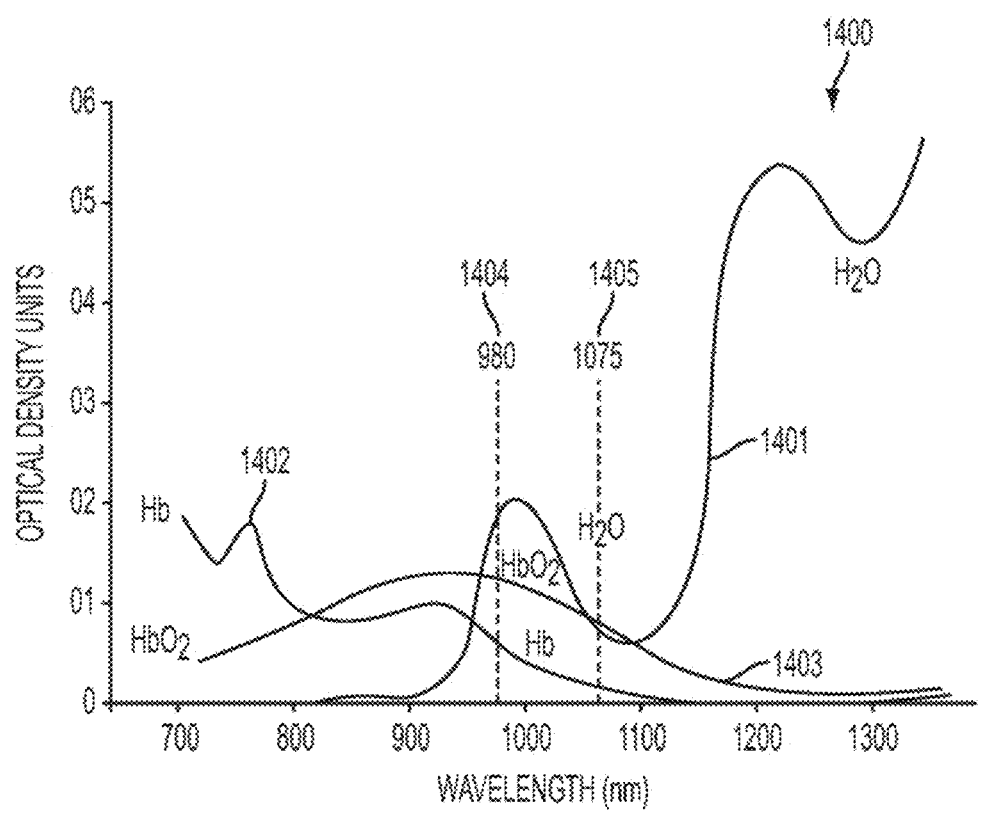
FIG. 14 illustrates the optical absorption or density as a function of wavelength between approximately 700 nm and 1300 nm for water, hemoglobin and oxygenated hemoglobin.

Even near wavelengths such as described in FIG. 13, the particular wavelength selected may be more specifically defined based on the target tissue of interest. In one particular embodiment, the vessel lumen may be modeled as water, and for this example assume that wavelengths in the vicinity of 980 nm are being selected to create thermal coagulation or occlusion. FIG. 14 shows the optical absorption or density as a function of wavelength 1400 between approximately 700 nm and 1300 nm. Curves are shown for the water absorption 1401, hemoglobin Hb absorption 1402, and oxygenated hemoglobin $HbO_2$ 1403. In this example, two particular wavelengths are compared: 980 nm 1404 and 1075 nm 1405. For instance, 980 nm may be generated using one or more laser diodes, while 1075 nm may be generated using an ytterbium-doped fiber laser. If maximizing the penetration depth is the significant problem, then 1075 nm 1405 may be preferred, since it falls near a local minimum in water 1401, hemoglobin 1402, and oxygenated hemoglobin 1403 absorption. On the other hand, if the penetration depth at 980 nm 1404 is adequate and the problem is to generate heat through water absorption, then 980 nm 1404 may be a preferred wavelength for the light source because of the higher water absorption. This wavelength range is only meant to be exemplary, but other wavelength ranges and particular criteria for selecting the wavelength may be used and are intended to be covered by this disclosure.

Figure 15:
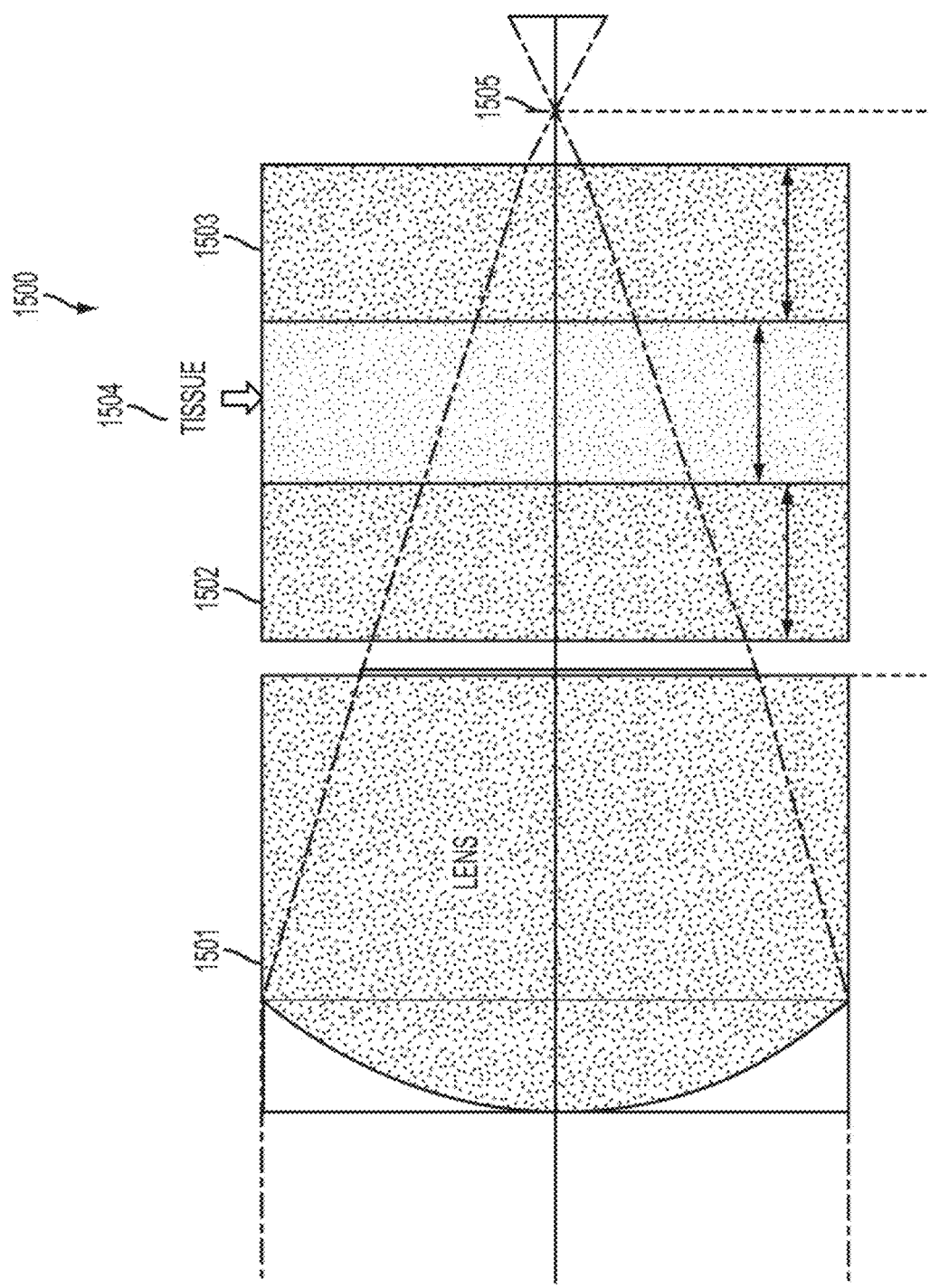
FIG. 15 shows a set-up used for in vitro damage experiments using focused infrared light. After a lens system, the tissue is placed between two microscope slides.

In another embodiment, focused infrared light has been used to preserve the top layer of a tissue while damaging nerves at a deeper level. For instance, FIG. 15 illustrates the set-up 1500 used for the focused infrared experiments. In this embodiment, a lens 1501 is used to focus the light. Although a single lens is shown, either multiple lenses, GRIN (gradient index) lenses, curved mirrors, or a combination of lenses and mirrors may be used. In this particular example, the tissue 1504 is placed between two microscope slides 1502 and 1503 for in vitro experiments. The tissue 1504 is renal artery wall either from porcine or bovine animals (about 1.2 mm thick sample)—i.e., this is the artery leading to the kidneys, and it is the artery where typically renal denervation may be performed to treat hypertension. For this example, the minimum beam waist 1505 falls behind the tissue, and the intensity contrast from the front of the tissue (closest to the lens) to the back of the tissue (furthest from the lens) is about 4:1. These are particular ranges used for this experiment, but other values and locations of minimum beam waist may also be used and intended to be covered by this disclosure.

Figure 16A:
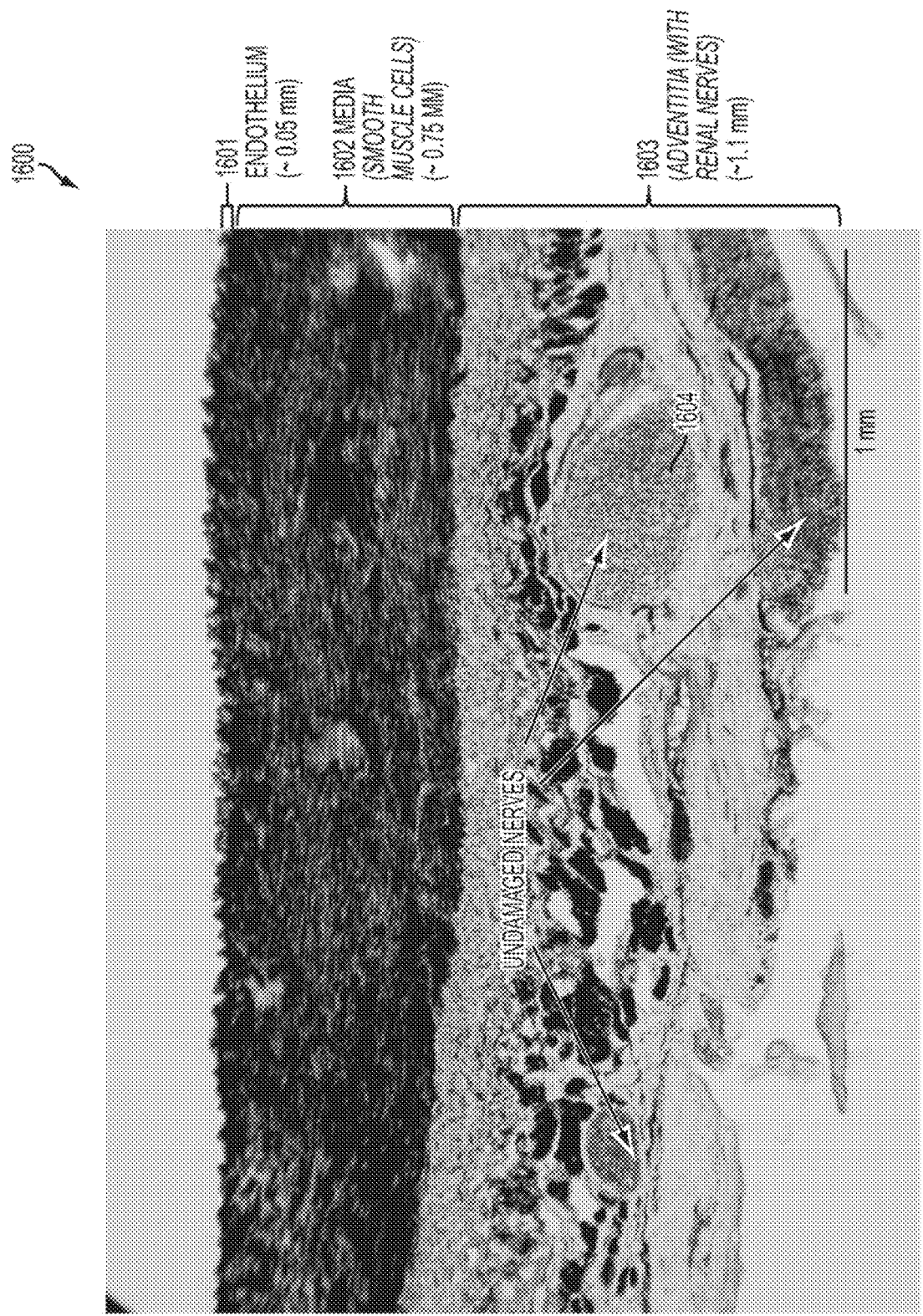
FIGS. 16A and 16B present histology of renal arteries comprising endothelium, media and adventitia layers and some renal nerves in or below the adventitia.
Figure 16B:
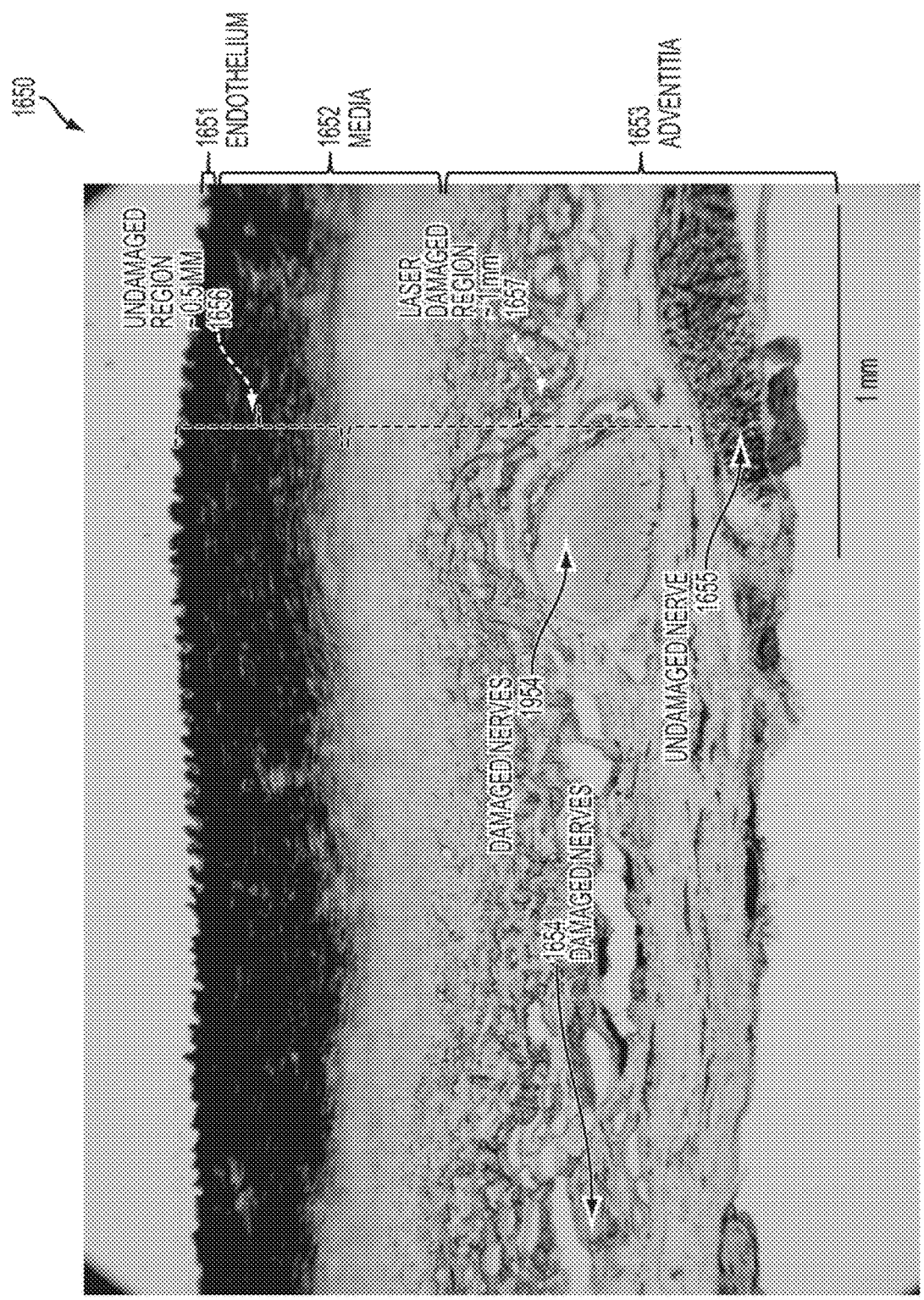

For a particular embodiment, histology of the renal artery is shown in FIG. 16A for no laser exposure 1600 and shown in FIG. 16B with focused infrared laser exposure 1650. In this experiment, the beam diameter incident on the lens was about 4 mm, and the distance from the edge of the flat side of lens to the minimum beam waist was about 3.75 mm. The beam diameter on the front side of the renal artery (i.e., the endothelium side) was about 1.6 mm, and the beam diameter on the back side of the renal artery was about 0.8 mm. In FIG. 16A with no laser exposure, the layers of the artery wall may be identified: top layer of endothelium 1601 that is about 0.05 mm thick, the media comprising smooth muscle cells or tissue 1602 that is about 0.75 mm thick, and the adventitia 1603 comprising some of the renal nerves 1604 that is about 1.1 mm thick. These are particular values for this experiment, and other layers and thicknesses may also be used and are intended to be covered by this disclosure.

The histology with focused infrared light exposure 1650 is illustrated in FIG. 16B. The laser light used is near 1708 nm from a cascaded Raman oscillator (described in greater detail herein), and the power incident on the tissue is about 0.8 W and the beam is scanned across the tissue at a rate of approximately 0.4 mm/sec. The various layers are still observable: the endothelium 1651, the media 1652, and the adventitia 1653. With this type of histology, the non-damaged regions remain darker (similar to FIG. 16A), while the laser induced damaged regions turn lighter in color. In this example, the endothelium 1651 and top layer of the media 1652 remain undamaged—i.e., the top approximately 0.5 mm is the undamaged region 1656. The laser damaged region 1657 extends for about 1 mm, and it includes the bottom layer of the media 1652 and much of the adventitia 1653. The renal nerves 1654 that fall within the damage region 1657 are also damaged (i.e., lighter colored). On the other hand, the renal nerves beyond this depth, such as 1655, may remain undamaged.

Thus, by using focused infrared light near 1708 nm in this example, the top approximately 0.5 mm of the renal artery is spared from laser damage. It should be noted that when the same experiment is conducted with a collimated laser beam, the entire approximately 1.5 mm is damaged (i.e., including regions 1656 and 1657). Therefore, the cone of light with the lower intensity at the top and the higher intensity toward the bottom may, in fact, help preserve the top layer from damage. There should be a Beer's Law attenuation of the light intensity as the light propagates into the tissue. For example, the light intensity should reduce exponentially at a rate determined by the absorption coefficient. In these experiments it appears that the focused light is able to overcome the Beer's law attenuation and still provide contrast in intensity between the front and back surfaces.

Figure 17:
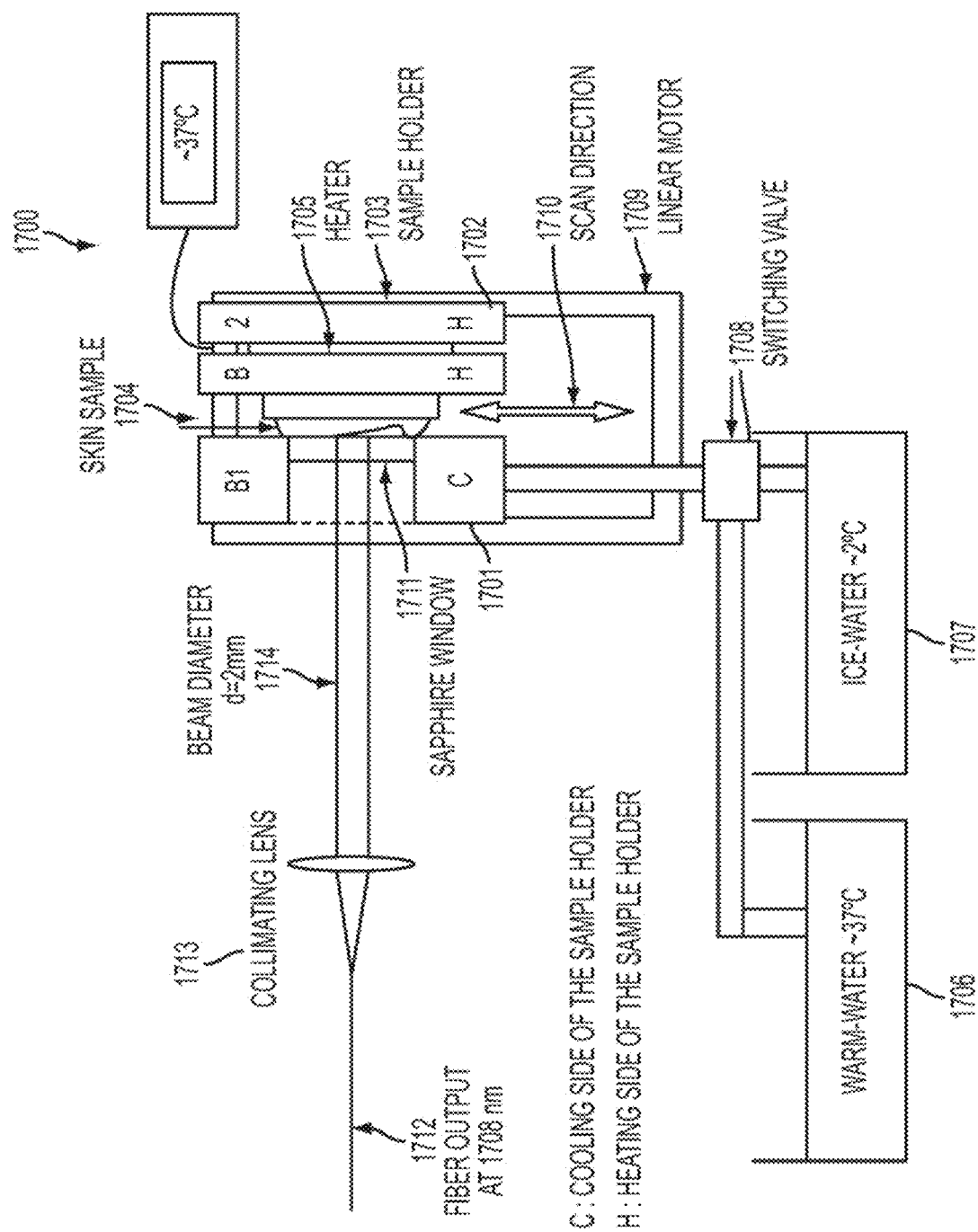
FIG. 17 illustrates the experimental set-up for ex vivo skin laser treatment with surface cooling to protect the epidermis and top layer of the dermis.
Figure 18A:
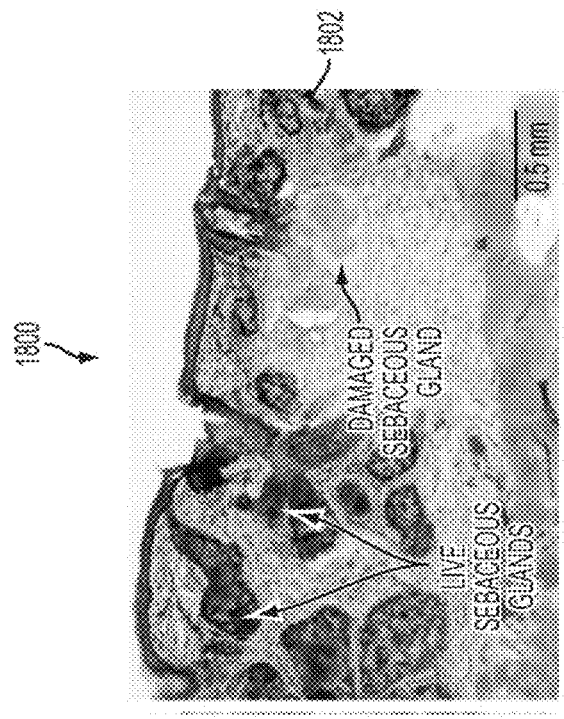
FIGS. 18A-18D show MTT histo-chemistry of ex vivo human skin treated with ~1708 nm laser and cold window (5 seconds precool; 2 mm diameter spot exposure for 3 seconds) at 725 mW (FIGS. 18A and 18B) corresponding to ~70 J/cm$^2$ average fluence and 830 mW (FIGS. 18C and 18D) corresponding to ~80 J/cm$^2$ average fluence.
Figure 18B:
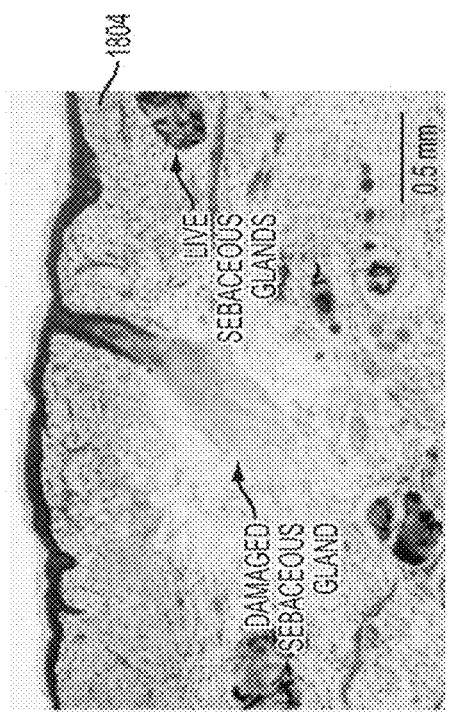
Figure 18C:
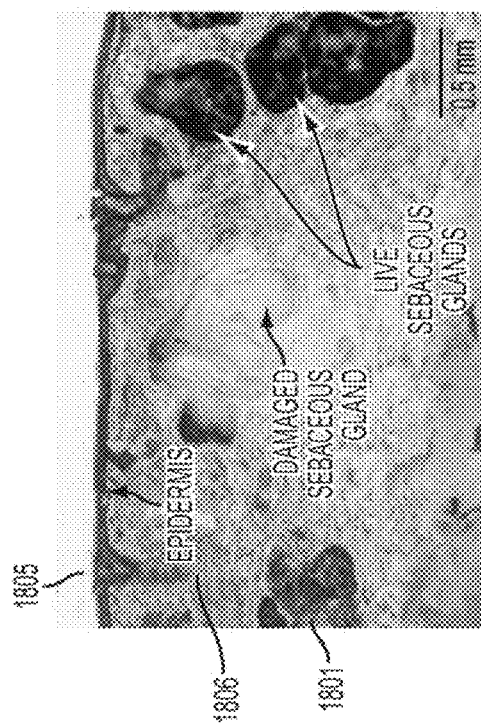
Figure 18D:
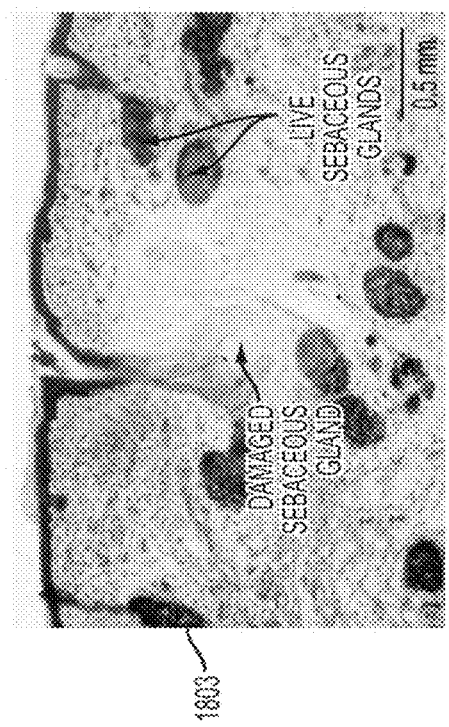

In another embodiment, experiments have also been conducted on dermatology samples with surface cooling, and surface cooling is shown to preserve the top layer of the skin during laser exposure. In this particular example, the experimental set-up 1700 is illustrated in FIG. 17. The skin sample 1704, or more generally sample under test, is placed in a sample holder 1703. The sample holder 1703 has a cooling side 1701 and a heating side 1702. The heating side 1702 comprises a heater 1705, which may be adjusted to operate around 37 degrees Celsius—i.e., close to body temperature. The cooling side 1701 is coupled to an ice-water bath 1707 (around 2 degrees Celsius) and a warm-water bath 1706 (around 37 degrees Celsius) through a switching valve 1708. The entire sample holder 1703 is mounted on a linear motor 1709, so the sample can be moved perpendicular 1710 to the incoming light beam.

In this embodiment, the light is incident on the sample 1704 through a sapphire window 1711. The sapphire material 1711 is selected because it is transparent to the infrared wavelengths, while also being a good thermal conductor. Thus, the top layer of the sample 1704 may be cooled by being approximately in contact with the sapphire window 1711. The laser light 1712 used is near 1708 nm from a cascaded Raman oscillator (described in greater detail herein), and one or more collimating lenses 1713 are used to create a beam with a diameter 1714 of approximately 2 mm. This is one particular embodiment of the sample surface cooling arrangement, but other apparatuses and methods may be used and are intended to be covered by this disclosure.

Experimental results obtained using the set-up of FIG. 17 are included in FIG. 18. In this example, FIG. 18 shows the MTT histochemistry of human skin 1800 treated with ~1708 nm laser (5 seconds pre-cool; 2 mm diameter spot exposure for 3 seconds) at 725 mW (A 1801, B 1802) corresponding to about 70 J/cm2 average fluence, and 830 mW (C 1803, D 1804) corresponding to about 80 J/cm2 average fluence. The images in FIG. 18 show that the application of a cold window was effective in protecting the epidermis 1805 (darker top layer) and the top approximately 0.4 or 0.5 mm of the dermis 1806. As before, the darker regions of the histology correspond to undamaged regions, while the lighter regions correspond to damaged regions. In contrast, when no surface cooling is applied, then thermal damage to the dermis occurs in the epidermis and dermis where the laser exposure occurs, and the thermal damage extends to about 1.3 or 1.4 mm or more from the skin surface. Thus, surface cooling applied to the skin may help to reduce or eliminate damage to the top layer of the skin under laser exposure.

In summary, experiments verify that infrared light, such as near 980 nm, 1210 nm, or 1700 nm, may achieve penetration depths between approximately 2 mm to 4 mm or more. The top layer of skin or tissue may be spared damage under laser exposure by focusing the light beyond the top layer, applying surface cooling, or some combination of the two. These are particular experimental results, but other wavelengths, methods and apparatuses may be used for achieving the penetration and minimizing damage to the top layer and are intended to be covered by this disclosure. In an alternate embodiment, it may be beneficial to use wavelengths near 1310 nm if the absorption from skin constituents (FIG. 10), such as collagen 1003, adipose 1002 and elastin 1004, are to be minimized. The water absorption 1001 near 1310 nm may still permit a penetration depth of approximately 1 cm, or perhaps less. In yet another embodiment, wavelengths near 1210 nm may be beneficial, if penetration depths on the order of 3 mm are adequate and less scattering loss (e.g. 1001 in FIG. 10) is desired. Any of FIG. 1, 6, 9, 10, or 11 may be used to select these or other wavelengths to achieve the desired penetration depth and to also perhaps target particular tissue of interest, and these alternate embodiments are also intended to be covered by this disclosure.

Laser Systems for Therapeutics or Diagnostics

Infrared light sources can be used for diagnostics and therapeutics in a number of medical applications. For example, broadband light sources can advantageously be used for diagnostics, while narrower band light sources can advantageously be used for therapeutics. In one embodiment, selective absorption or damage can be achieved by choosing the laser wavelength to lie approximately at an absorption peak of particular tissue types. Also, by using infrared wavelengths that minimize water absorption peaks and longer wavelengths that have lower tissue scattering, larger penetration depths into the biological tissue can be obtained. In this disclosure, infrared wavelengths include wavelengths in the range of approximately 0.9 microns to 10 microns, with wavelengths between about 0.98 microns and 2.5 microns more suitable for certain applications.

As used throughout this document, the term "couple" and or "coupled" refers to any direct or indirect communication between two or more elements, whether or not those elements are physically connected to one another. In this disclosure, the term "damage" refers to affecting a tissue or sample so as to render the tissue or sample inoperable. For instance, if a particular tissue normally emits certain signaling chemicals, then by "damaging" the tissue is meant that the tissue reduces or no longer emits that certain signaling chemical. The term "damage" and or "damaged" may include ablation, melting, charring, killing, or simply incapacitating the chemical emissions from the particular tissue or sample. In one embodiment, histology or histochemical analysis may be used to determine whether a tissue or sample has been damaged.

As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or lightpipe. In one embodiment, the gain fiber may be doped with rare earth material, such as ytterbium, erbium, and/or thulium. In another embodiment, the infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam may be coupled to a gain medium to excite the gain medium, which in turn may amplify another input optical signal or beam. In one particular example, the gain medium may be a doped fiber, such as a fiber doped with ytterbium, erbium, and/or thulium. In another embodiment, the gain medium may be a fused silica fiber or a fiber with a Raman effect from the glass. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and/or "supercontinuum" and/or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, the Raman effect, modulational instability, and self-phase modulation.

As used throughout this disclosure, the terms "optical light" and/or "optical beam" and or "light beam" refer to photons or light transmitted to a particular location in space. The "optical light" and or "optical beam" and/or "light beam" may be modulated or unmodulated, which also means that they may or may not contain information. In one embodiment, the "optical light" and/or "optical beam" and/or "light beam" may originate from a fiber, a fiber laser, a laser, a light emitting diode, a lamp, a pump laser, or a light source.

As used throughout this document, the terms "near" or "about" or the symbol "~" refer to one or more wavelengths of light with wavelengths around the stated wavelength to accomplish the function described. For example, "near 1720 nm" may include wavelengths of between about 1680 nm and 1760 nm. In one embodiment, the term "near 1720 nm" refers to one or more wavelengths of light with a wavelength value anywhere between approximately 1700 nm and 1740 nm. Similarly, as used throughout this document, the term "near 1210 nm" refers to one or wavelengths of light with a wavelength value anywhere between approximately 1170 nm and 1250 nm. In one embodiment, the term "near 1210 nm" refers to one or more wavelengths of light with a wavelength value anywhere between approximately 1190 nm and 1230 nm.

Different light sources may be selected for the infrared based on the needs of the application. Some of the features for selecting a particular light source include power or intensity, wavelength range or bandwidth, spatial or temporal coherence, spatial beam quality for focusing or transmission over long distance, and pulse width or pulse repetition rate. Depending on the application, lamps, light emitting diodes (LEDs), laser diodes (LD's), tunable LD's, super-luminescent laser diodes (SLDs), fiber lasers or super-continuum (SC) sources may be advantageously used. Also, different fibers may be used for transporting the light, such as fused silica fibers, plastic fibers, mid-infrared fibers (e.g., tellurite, chalcogenides, fluorides, ZBLAN, etc.), photonic crystal fibers, or a hybrid of these fibers.

In one embodiment, LED's can be used that have a higher power level in the infrared wavelength range. LED's produce an incoherent beam, but the power level can be higher than a lamp and with higher energy efficiency. Also, the LED output may more easily be modulated, and the LED provides the option of continuous wave or pulsed mode of operation. LED's are solid state components that emit a wavelength band that is of moderate width, typically between about 20 nm to 40 nm. There are also so-called super-luminescent LEDs that may even emit over a much wider wavelength range. In another embodiment, a wide band light source may be constructed by combining different LEDs that emit in different wavelength bands, some of which could preferably overlap in spectrum. One advantage of LEDs as well as other solid state components is the compact size that they may be packaged into.

In yet another embodiment, various types of laser diodes may be used in the infrared wavelength range. Just as LEDs may be higher in power but narrower in wavelength emission than lamps and thermal sources, the LDs may be yet higher in power but yet narrower in wavelength emission than LEDs. Different kinds of LDs may be used, including Fabry-Perot LDs, distributed feedback (DFB) LDs, distributed Bragg reflector (DBR) LDs. A plurality of LDs may be spatially multiplexed, polarization multiplexed, wavelength multiplexed, or a combination of these multiplexing methods. Also, the LDs may be fiber pig-tailed or have one or more lenses on the output to collimate or focus the light. Another advantage of LDs is that they may be packaged compactly and may have a spatially coherent beam output. Moreover, tunable LDs that can tune over a range of wavelengths are also available. The tuning may be done by varying the temperature, or electrical current may be used in particular structures such as distributed Bragg reflector (DBR) LDs. In another embodiment, external cavity LDs may be used that have a tuning element, such as a fiber grating or a bulk grating, in the external cavity.

In another embodiment, super-luminescent laser diodes may provide higher power as well as broad bandwidth. An SLD is typically an edge emitting semiconductor light source based on super-luminescence (e.g., this could be amplified spontaneous emission). SLDs combine the higher power and brightness of LDs with the low coherence of conventional LEDs, and the emission band for SLD's may be 5 nm to 100 nm wide, preferably in the 60 nm to 100 nm range for some applications. Although currently SLDs are commercially available in the wavelength range of approximately 400 nm to 1700 nm, SLDs could and may in the future be made the cover a broader region of the infrared.

Figure 19:
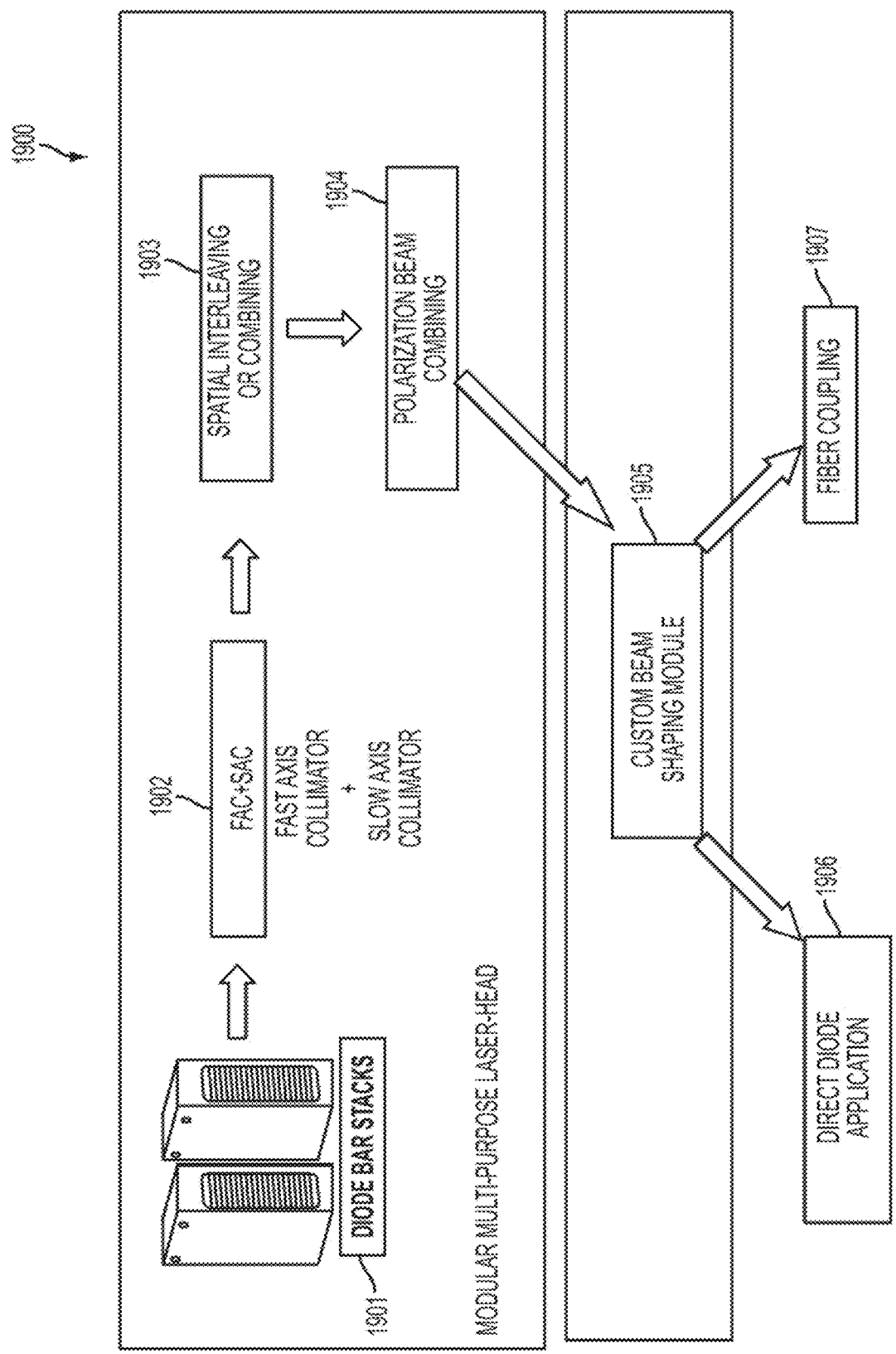
FIG. 19 illustrates a block diagram or building blocks for constructing high power laser diode assemblies.

In yet another embodiment, high power LDs for either direct excitation or to pump fiber lasers and SC light sources may be constructed using one or more laser diode bar stacks. As an example, FIG. 19 shows an example of the block diagram 1900 or building blocks for constructing the high power LDs. In this embodiment, one or more diode bar stacks 1901 may be used, where the diode bar stack may be an array of several single emitter LDs. Since the fast axis (e.g., vertical direction) may be nearly diffraction limited while the slow-axis (e.g., horizontal axis) may be far from diffraction limited, different collimators 1902 may be used for the two axes.

Then, the brightness may be increased by spatially combining the beams from multiple stacks 1903. The combiner may include spatial interleaving, it may include wavelength multiplexing, or it may involve a combination of the two. Different spatial interleaving schemes may be used, such as using an array of prisms or mirrors with spacers to bend one array of beams into the beam path of the other. In another embodiment, segmented mirrors with alternate high-reflection and anti-reflection coatings may be used. Moreover, the brightness may be increased by polarization beam combining 1904 the two orthogonal polarizations, such as by using a polarization beam splitter. In a particular embodiment, the output may then be focused or coupled into a large diameter core fiber. As an example, typical dimensions for the large diameter core fiber range from diameters of approximately 100 microns to 400 microns or more. Alternatively or in addition, a custom beam shaping module 1905 may be used, depending on the particular application. For example, the output of the high power LD may be used directly 1906, or it may be fiber coupled 1907 to combine, integrate, or transport the high power LD energy. These high power LDs may grow in importance because the LD powers can rapidly scale up. For example, instead of the power being limited by the power available from a single emitter, the power may increase in multiples depending on the number of diodes multiplexed and the size of the large diameter fiber. Although FIG. 19 is shown as one embodiment, some or all of the elements may be used in a high power LD, or additional elements may also be used.

Infrared Super-Continuum Lasers

Each of the light sources described above have particular strengths, but they also may have limitations. For example, there is typically a trade-off between wavelength range and power output. Also, sources such as lamps, thermal sources, and LEDs produce incoherent beams that may be difficult to focus to a small area and may have difficulty propagating for long distances. An alternative source that may overcome some of these limitations is an SC light source. Some of the advantages of the SC source may include high power and intensity, wide bandwidth, spatially coherent beam that can propagate nearly transform limited over long distances, and easy compatibility with fiber delivery.

Supercontinuum lasers may combine the broadband attributes of lamps with the spatial coherence and high brightness of lasers. By exploiting a modulational instability initiated supercontinuum (SC) mechanism, an all-fiber-integrated SC laser with no moving parts may be built using commercial-off-the-shelf (COTS) components. Moreover, the fiber laser architecture may be a platform where SC in the visible, near-infrared/SWIR, or mid-IR can be generated by appropriate selection of the amplifier technology and the SC generation fiber. But until now, SC lasers were used primarily in laboratory settings since typically large, table-top, mode-locked lasers were used to pump nonlinear media such as optical fibers to generate SC light. However, those large pump lasers may now be replaced with diode lasers and fiber amplifiers that gained maturity in the telecommunications industry.

Figure 20:
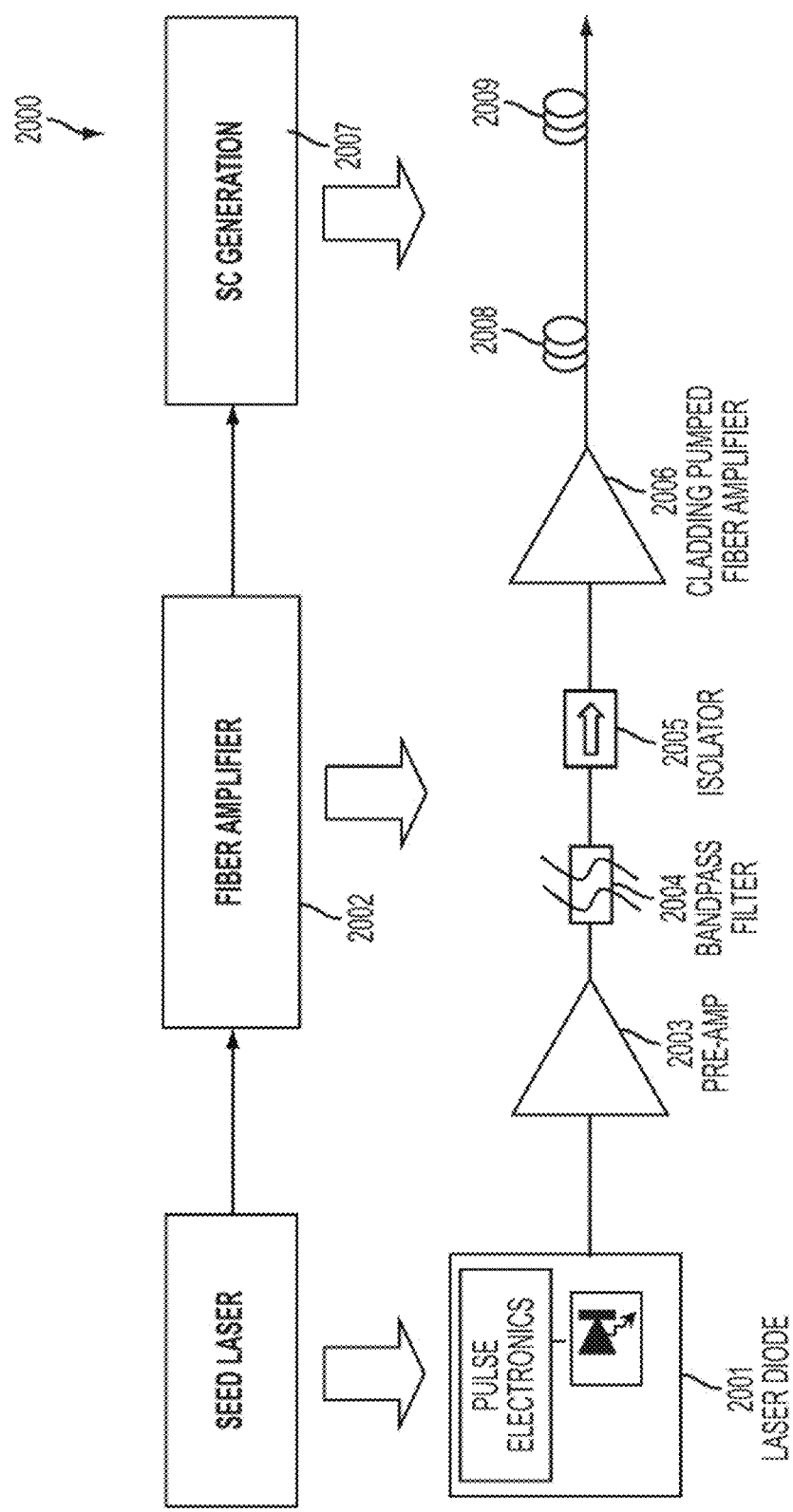
FIG. 20 shows a platform architecture for different wavelength ranges for an all-fiber-integrated, high powered, super-continuum light source.

In one embodiment, an all-fiber-integrated, high-powered SC light source 2000 may be elegant for its simplicity (FIG. 20). The light may be first generated from a seed laser diode 2001. For example, the seed LD 2001 may be a distributed feedback (DFB) laser diode with a wavelength near 1542 nm or 1550 nm, with approximately 0.5-2.0 ns pulsed output, and with a pulse repetition rate between one kilohertz and about 100 MHz or more. The output from the seed laser diode may then be amplified in a multiple-stage fiber amplifier 2002 comprising one or more gain fiber segments. In a particular embodiment, the first stage pre-amplifier 2003 may be designed for optimal noise performance. For example, the pre-amplifier 2003 may be a standard erbium-doped fiber amplifier or an erbium/ytterbium doped cladding pumped fiber amplifier. Between amplifier stages 2003 and 2006, it may be advantageous to use band-pass filters 2004 to block amplified spontaneous emission and isolators 2005 to prevent spurious reflections. Then, the power amplifier stage 2006 may use a cladding-pumped fiber amplifier that may be optimized to minimize nonlinear distortion. The power amplifier fiber 2006 may also be an erbium-doped fiber amplifier, if only low or moderate power levels are to be generated.

The SC generation 2007 may occur in the relatively short lengths of fiber that follow the pump laser. Exemplary SC fiber lengths may range from a few millimeters to 100 m or more. In one embodiment, the SC generation may occur in a first fiber 2008 where the modulational-instability initiated pulse break-up occurs primarily, followed by a second fiber 2009 where the SC generation and spectral broadening occurs primarily.

In one embodiment, one or two meters of standard single-mode fiber (SMF) after the power amplifier stage may be followed by several meters of SC generation fiber. For this example, in the SMF the peak power may be several kilowatts and the pump light may fall in the anomalous group-velocity dispersion regime—often called the soliton regime. For high peak powers in the dispersion regime, the nanosecond pulses may be unstable due to a phenomenon known as modulational instability, which is basically parametric amplification in which the fiber nonlinearity helps to phase match the pulses. As a consequence, the nanosecond pump pulses may be broken into many shorter pulses as the modulational instability tries to form soliton pulses from the quasi-continuous-wave background. Although the laser diode and amplification process starts with approximately nanosecond-long pulses, modulational instability in the short length of SMF fiber may form approximately 0.5 ps to several-picosecond-long pulses with high intensity. Thus, the few meters of SMF fiber may result in an output similar to that produced by mode-locked lasers, except in a much simpler and cost-effective manner.

The short pulses created through modulational instability may then be coupled into a nonlinear fiber for SC generation. The nonlinear mechanisms leading to broadband SC may include four-wave mixing or self-phase modulation along with the optical Raman effect. Since the Raman effect is self-phase-matched and shifts light to longer wavelengths by emission of optical photons, the SC may spread to longer wavelengths very efficiently. The short-wavelength edge may arise from four-wave mixing, and often times the short wavelength edge may be limited by increasing group-velocity dispersion in the fiber. In many instances, if the particular fiber used has sufficient peak power and SC fiber length, the SC generation process may fill the long-wavelength edge up to the transmission window.

Mature fiber amplifiers for the power amplifier stage 2006 include ytterbium-doped fibers (near 1060 nm), erbium-doped fibers (near 1550 nm), erbium/ytterbium-doped fibers (near 1550 nm), or thulium-doped fibers (near 2000 nm). In various embodiments, candidates for SC fiber 2009 include fused silica fibers (for generating SC between 0.8-2.7 µm), mid-IR fibers such as fluorides, chalcogenides, or tellurites (for generating SC out to 4.5 µm or longer), photonic crystal fibers (for generating SC between 0.4 and 1.7 µm), or combinations of these fibers. Therefore, by selecting the appropriate fiber-amplifier doping for 2006 and nonlinear fiber 2009, SC may be generated in the visible, near-IR/SWIR, or mid-IR wavelength region.

The configuration 2000 of FIG. 20 is just one particular example, and other configurations can be used and are intended to be covered by this disclosure. For example, further gain stages may be used, and different types of lossy elements or fiber taps may be used between the amplifier stages. In another embodiment, the SC generation may occur partially in the amplifier fiber and in the pig-tails from the pump combiner or other elements. In yet another embodiment, polarization maintaining fibers may be used, and a polarizer may also be used to enhance the polarization contrast between amplifier stages. Also, not discussed in detail are many accessories that may accompany this set-up, such as driver electronics, pump laser diodes, safety shut-offs, and thermal management and packaging.

Figure 21:
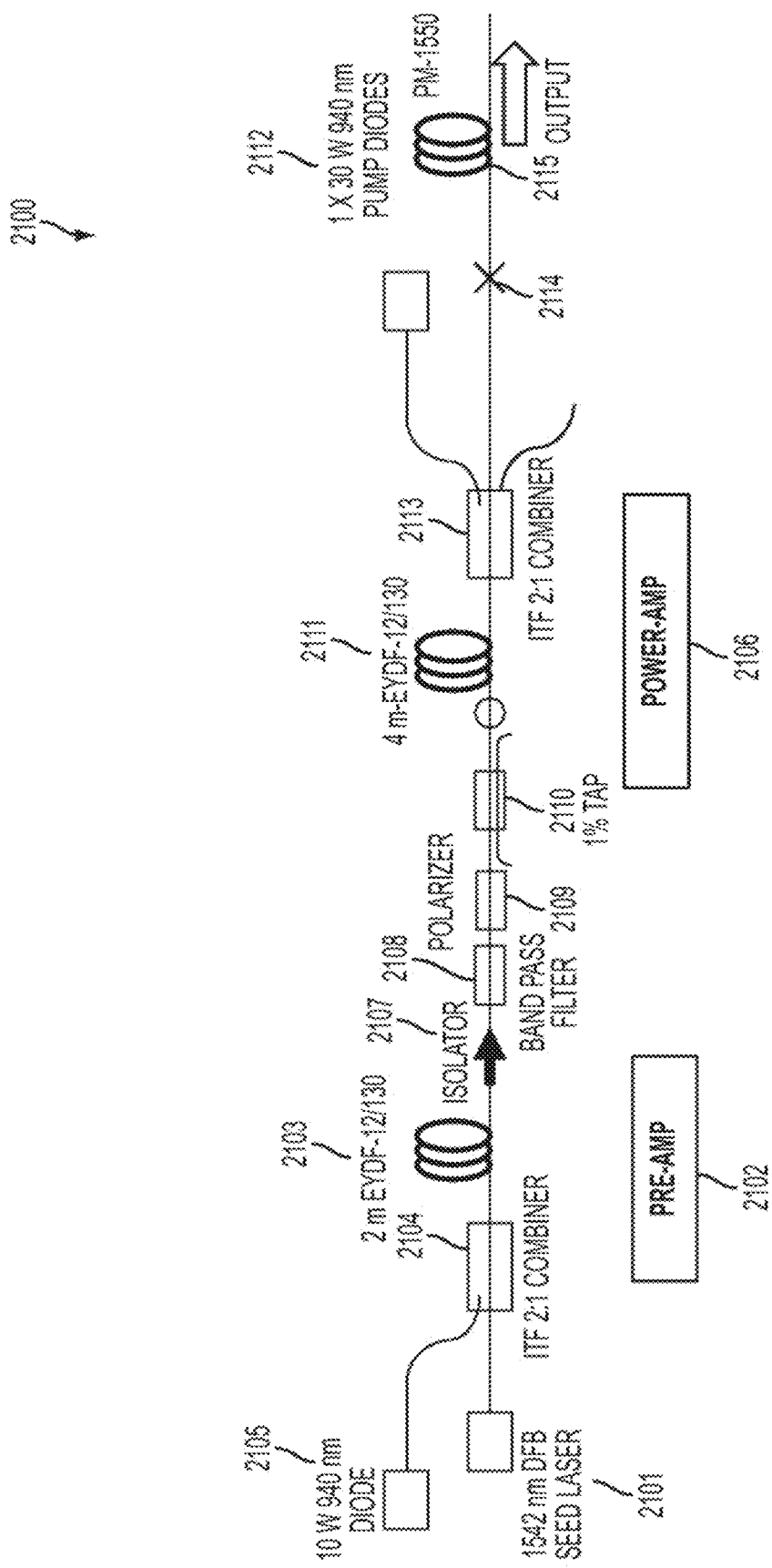
FIG. 21 illustrates one embodiment for a short-wave infrared super-continuum light source.

In one embodiment, one example of the SC laser that operates in the short wave infrared (SWIR) is illustrated in FIG. 21. This SWIR SC source 2100 produces an output of up to approximately 5 W over a spectral range of about 1.5 microns to 2.4 microns, and this particular laser is made out of polarization maintaining components. The seed laser 2101 is a distributed feedback (DFB) laser operating near 1542 nm producing approximately 0.5 nsec pulses at an about 8 MHz repetition rate. The pre-amplifier 2102 is forward pumped and uses about 2 m length of erbium/ytterbium cladding pumped fiber 2103 (often also called dual-core fiber) with an inner core diameter of 12 microns and outer core diameter of 130 microns. The pre-amplifier gain fiber 2103 is pumped using a 10 W 940 nm laser diode 2105 that is coupled in using a fiber combiner 2104.

In this particular 5 W unit, the mid-stage between amplifier stages 2102 and 2106 comprises an isolator 2107, a band-pass filter 2108, a polarizer 2109 and a fiber tap 2110. The power amplifier 2106 uses a 4 m length of the 12/130 micron erbium/ytterbium doped fiber 2111 that is counter-propagating pumped using one or more 30 W 940 nm laser diodes 2112 coupled in through a combiner 2113. An approximately 1-2 meter length of the combiner pig-tail helps to initiate the SC process, and then a length of PM-1550 fiber 2115 (polarization maintaining, single-mode, fused silica fiber optimized for 1550 nm) is spliced 2114 to the combiner output.

Figure 22:
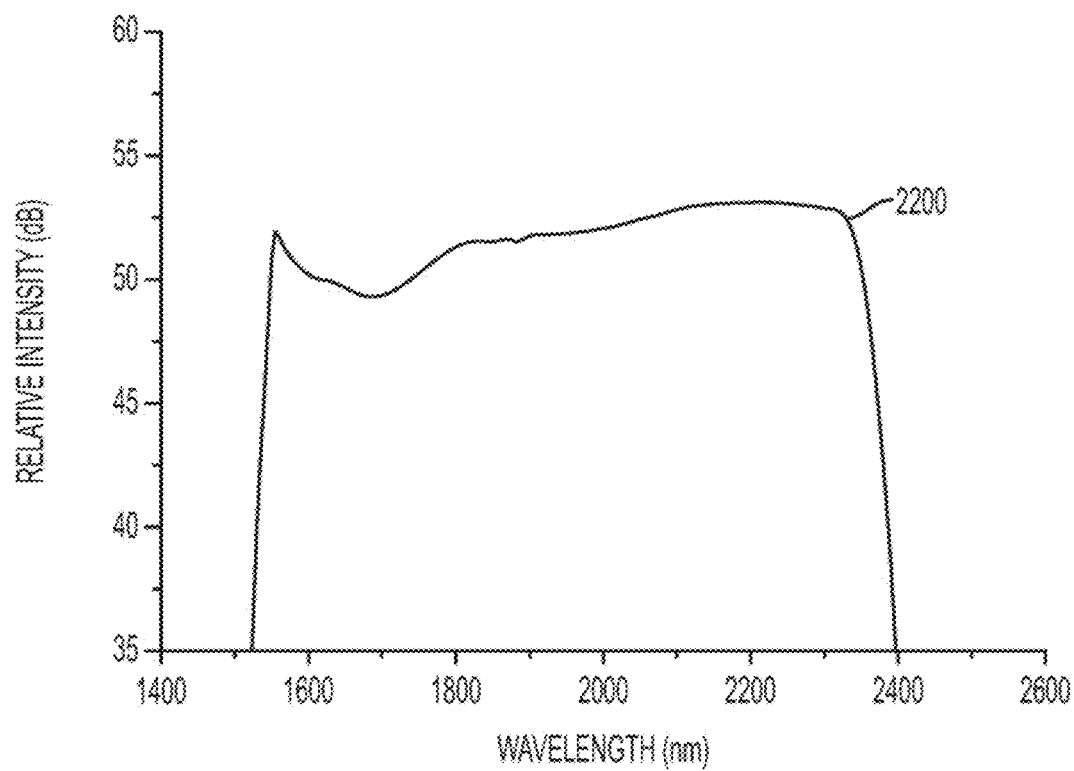
FIG. 22 shows the output spectrum from the SWIR SC laser of FIG. 21 when about 10 m length of fiber for SC generation is used. This fiber is a single-mode, non-dispersion shifted fiber that is optimized for operation near 1550 nm.

If an approximately 10 m length of output fiber is used, then the resulting output spectrum 2200 is shown in FIG. 22. The details of the output spectrum 2200 depend on the peak power into the fiber, the fiber length, and properties of the fiber such as length and core size, as well as the zero dispersion wavelength and the dispersion properties. For example, if a shorter length of fiber is used, then the spectrum actually reaches to longer wavelengths (e.g., a 2 m length of SC fiber broadens the spectrum to about 2500 nm). Also, if extra-dry fibers are used with less O—H content, then the wavelength edge may also reach to a longer wavelength. To generate more spectrum toward the shorter wavelengths, the pump wavelength (in this case ~1542 nm) should be close to the zero dispersion wavelength in the fiber. For example, by using a dispersion shifted fiber or so-called non-zero dispersion shifted fiber, the short wavelength edge may shift to shorter wavelengths.

Although one particular example of a 5 W SWIR-SC implementation has been described, different components, different fibers, and different configurations may also be used consistent with this disclosure. For instance, another embodiment of the similar configuration 2100 in FIG. 21 may be used to generate high powered SC between approximately 1060 nm and 1800 nm. For this embodiment, the seed laser 2101 may be a 1064 nm distributed feedback (DFB) laser diode, the pre-amplifier gain fiber 2103 may be a ytterbium-doped fiber amplifier with 10/125 microns dimensions, and the pump laser 2105 may be a 10 W 915 nm laser diode. A mode field adapter may be included in the mid-stage, in addition to the isolator 2107, band pass filter 2108, polarizer 2109 and tap 2110. The gain fiber 2111 in the power amplifier may be a 20 m length of ytterbium-doped fiber with 25/400 microns dimension. The pump 2112 for the power amplifier may be up to six pump diodes providing 30 W each near 915 nm. For this much pump power, the output power in the SC may be as high as 50 W or more.

In one embodiment, it may be desirous to generate high power SWIR SC over 1.4-1.8 microns and separately 2-2.5 microns (the window between 1.8 and 2 microns may be less important due to the strong water and atmospheric absorption). For example, the SC source of FIG. 23A can lead to bandwidths ranging from about 1400 nm to 1800 nm or broader, while the SC source of FIG. 23B can lead to bandwidths ranging from about 1900 nm to 2500 nm or broader. Since these wavelength ranges are shorter than about 2500 nm, the SC fiber can be based on fused silica fiber. Exemplary SC fibers include standard single-mode fiber (SMF), high-nonlinearity fiber, high-NA fiber, dispersion shifted fiber, dispersion compensating fiber, and photonic crystal fibers. Non-fused-silica fibers can also be used for SC generation, including chalcogenides, fluorides, ZBLAN, tellurites, and germanium oxide fibers.

In one embodiment, FIG. 23A illustrates a block diagram for an SC source 2300 capable of generating light between approximately 1400 nm and 1800 nm or broader. As an example, a pump fiber laser similar to FIG. 21 can be used as the input to a SC fiber 2309. The seed laser diode 2301 can comprise a DFB laser that generates, for example, several milliwatts of power around 1542 nm or 1553 nm. The fiber pre-amplifier 2302 can comprise an erbium-doped fiber amplifier or an erbium/ytterbium doped double clad fiber. In this example a mid-stage amplifier 2303 can be used, which can comprise an erbium/ytterbium doped double-clad fiber. A bandpass filter 2305 and isolator 2306 may be used between the pre-amplifier 2302 and mid-stage amplifier 2303. The power amplifier stage 2304 can comprise a larger core size erbium/ytterbium doped double-clad fiber, and another bandpass filter 2307 and isolator 2308 can be used before the power amplifier 2304. The output of the power amplifier can be coupled to the SC fiber 2309 to generate the SC output 2310. This is just one exemplary configuration for an SC source, and other configurations or elements may be used consistent with this disclosure.

In yet another embodiment, FIG. 23B illustrates a block diagram for an SC source 2350 capable of generating light exemplary between approximately 1900 nm and 2500 nm or broader. As an example, the seed laser diode 2351 can comprise a DFB or DBR laser that generates, for example, several milliwatts of power around 1542 nm or 1553 nm. The fiber pre-amplifier 2352 can comprise an erbium-doped fiber amplifier or an erbium/ytterbium doped double-clad fiber. In this example a mid-stage amplifier 2353 can be used, which can comprise an erbium/ytterbium doped double-clad fiber. A bandpass filter 2355 and isolator 2356 may be used between the pre-amplifier 2352 and mid-stage amplifier 2353. The power amplifier stage 2354 can comprise a thulium doped double-clad fiber, and another isolator 2357 can be used before the power amplifier 2354. Note that the output of the mid-stage amplifier 2353 can be approximately near 1550 nm, while the thulium-doped fiber amplifier 2354 can amplify wavelengths longer than approximately 1900 nm and out to about 2100 nm. Therefore, for this configuration wavelength shifting may be required between 2353 and 2354. In one embodiment, the wavelength shifting can be accomplished using a length of standard single-mode fiber 2358, which can have exemplary lengths between approximately 5 meters and 50 meters. The output of the power amplifier 2354 can be coupled to the SC fiber 2359 to generate the SC output 2360. This is just one exemplary configuration for an SC source, and other configurations or elements can be used consistent with this disclosure. For example, the various amplifier stages can comprise different amplifier types, such as erbium doped fibers, ytterbium doped fibers, erbium/ytterbium co-doped fibers and thulium doped fibers. One advantage of the SC lasers illustrated in FIGS. 20-23 are that they may use all-fiber components, so that the SC laser can be all-fiber, monolithically integrated with no moving parts. The all-integrated configuration can consequently be robust and reliable.

FIGS. 20-23 are examples of SC light sources that may advantageously used for SWIR light generation in various medical diagnostic and therapeutic applications. However, many other versions of the SC light sources may also be made that are intended to also be covered by this disclosure. For example, the SC generation fiber could be pumped by a mode-locked laser, a gain-switched semiconductor laser, an optically pumped semiconductor laser, a solid state laser, other fiber lasers, or a combination of these types of lasers.

Also, rather than using a fiber for SC generation, either a liquid or a gas cell might be used as the nonlinear medium in which the spectrum is to be broadened.

Even within the all-fiber versions illustrated such as in FIG. 21, different configurations could be used consistent with the disclosure. In an alternate embodiment, it may be desirous to have a lower cost version of the SWIR SC laser of FIG. 21. One way to lower the cost could be to use a single stage of optical amplification, rather than two stages, which may be feasible if lower output power is required or the gain fiber is optimized. For example, the pre-amplifier stage 2102 might be removed, along with at least some of the mid-stage elements. In yet another embodiment, the gain fiber could be double passed to emulate a two stage amplifier. In this example, the pre-amplifier stage 2102 might be removed, and perhaps also some of the mid-stage elements. A mirror or fiber grating reflector could be placed after the power amplifier stage 2106 that may preferentially reflect light near the wavelength of the seed laser 2101. If the mirror or fiber grating reflector can transmit the pump light near 940 nm, then this could also be used instead of the pump combiner 2113 to bring in the pump light 2112. The SC fiber 2115 could be placed between the seed laser 2101 and the power amplifier stage 2106 (SC is only generated after the second pass through the amplifier, since the power level may be sufficiently high at that time). In addition, an output coupler may be placed between the seed laser diode 2101 and the SC fiber, which now may be in front of the power amplifier 2106. In a particular embodiment, the output coupler could be a power coupler or divider, a dichroic coupler (e.g., passing seed laser wavelength but outputting the SC wavelengths), or a wavelength division multiplexer coupler. This is just one further example, but a myriad of other combinations of components and architectures could also be used for SC light sources to generate SWIR light that are intended to be covered by this disclosure.

Detection Systems

As discussed earlier, the active remote sensing system or hyper-spectral imaging system may be on an airborne platform, mounted on a vehicle, a stationary transmission or reflection set-up, or even held by a human for a compact system. For such a system, there are fundamentally two hardware parts: the transmitter or light source and the detection system. Between the two, perhaps in a transmission or reflection setting, may be the sample being tested or measured. Moreover, the output from the detection system may go to a computational system, comprising computers or other processing equipment. The output from the computational system may be displayed graphically as well as with numerical tables and perhaps an identification of the material composition. These are just some of the parts of the systems, but other elements may be added or be eliminated, and these modified configurations are also intended to be covered by this disclosure.

By use of an active illuminator, a number of advantages may be achieved. First, the variations due to sunlight and time-of-day may be factored out. The effects of the weather, such as clouds and rain, might also be reduced. Also, higher signal-to-noise ratios may be achieved. For example, one way to improve the signal-to-noise ratio would be to use modulation and lock-in techniques. In one embodiment, the light source may be modulated, and then the detection system would be synchronized with the light source. In a particular embodiment, the techniques from lock-in detection may be used, where narrow band filtering around the modulation frequency may be used to reject noise outside the modulation frequency. In an alternate embodiment, change detection schemes may be used, where the detection system captures the signal with the light source on and with the light source off. Again, for this system the light source may be modulated. Then, the signal with and without the light source is differenced. This may enable the sun light changes to be subtracted out. In addition, change detection may help to identify objects that change in the field of view. Using a lock-in type technique (e.g., detecting at the same frequency as the pulsed light source and also possibly phase locked to the same signal), the detection system may be able to reject background or spurious signals and increase the signal-to-noise ratio of the measurement. In the following some exemplary detection systems are described.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

Figure 24:
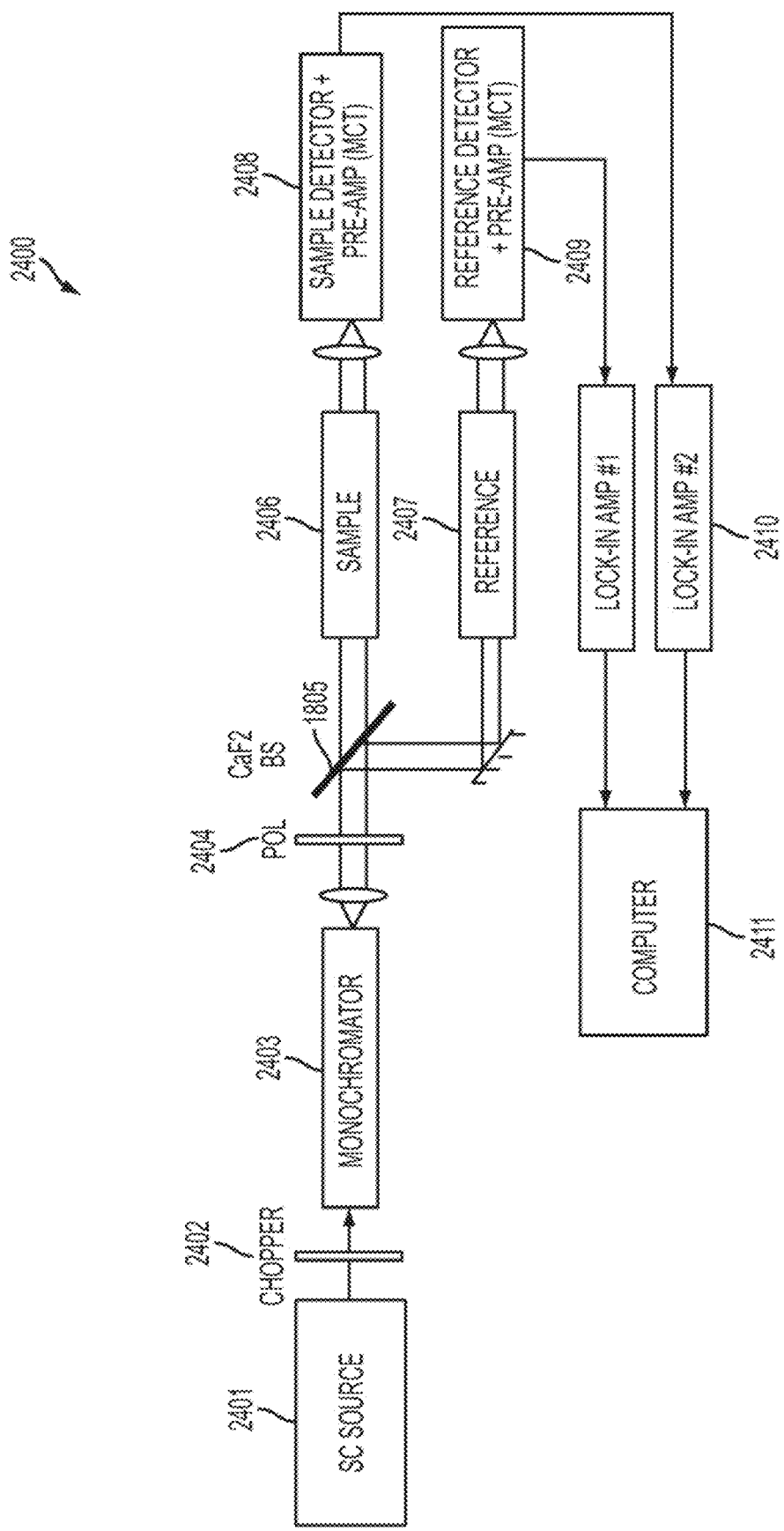
FIG. 24 exemplifies a dual-beam experimental set-up that may be used to subtract out (or at least minimize the adverse effects of) light source fluctuations.
Figure 25:
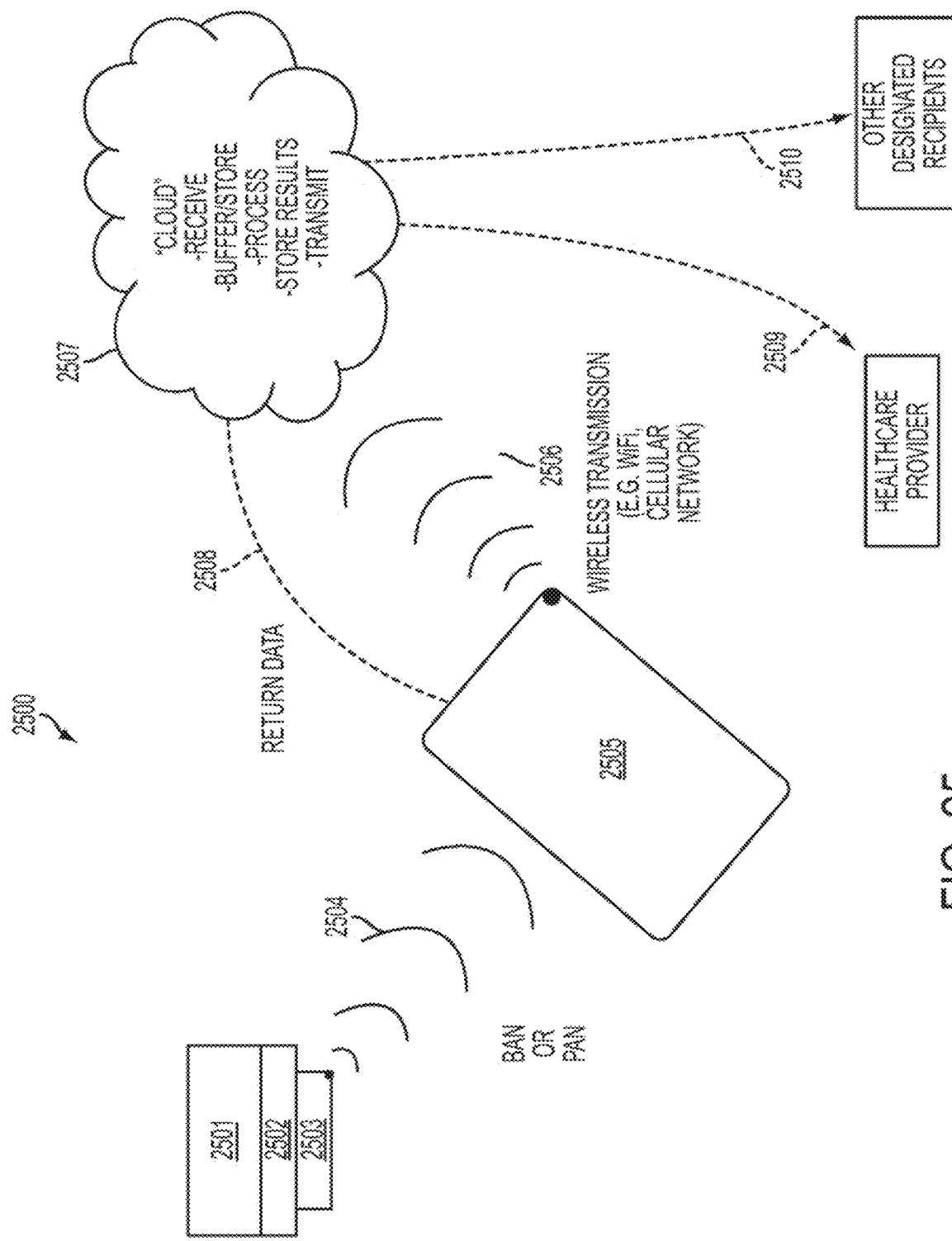
FIG. 25 schematically shows that a device can be part of a personal or body area network that communicates with another device (e.g., smart phone or tablet) that communicates with the cloud. The cloud may in turn communicate information with the user, healthcare providers, or other designated recipients.

In one example of multi-beam detection systems, a dual-beam set-up 2400 such as in FIG. 24 may be used to subtract out (or at least minimize the adverse effects of) light source fluctuations. In one embodiment, the output from an SC source 2401 may be collimated using a calcium fluoride ($CaF_2$) lens 2402 and then focused into the entrance slit of the monochromator 2403. At the exit slit, light at the selected wavelength is collimated again and may be passed through a polarizer 2404 before being incident on a calcium fluoride beam splitter 2405. After passing through the beam splitter 2405, the light is split into a sample 2406 and reference 2407 arm to enable ratiometric detection that may cancel out effects of intensity fluctuations in the SC source 2401. The light in the sample arm 2406 passes through the sample of interest and is then focused onto a HgCdTe detector 2408 connected to a pre-amp. A chopper 2402 and lock-in amplifier 2410 setup enable low noise detection of the sample arm signal. The light in the reference arm 2407 passes through an empty container (cuvette, gas cell etc.) of the same kind as used in the sample arm. A substantially identical detector 2409, pre-amp and lock-in amplifier 2410 is used for detection of the reference arm signal. The signal may then be analyzed using a computer system 2411. This is one particular example of a method to remove fluctuations from the light source, but other components may be added and other configurations may be used, and these are also intended to be covered by this disclosure.

Although particular examples of detection systems have been described, combinations of these systems or other systems may also be used, and these are also within the scope of this disclosure. As one example, environmental fluctuations (such as turbulence or winds) may lead to fluctuations in the beam for active remote sensing or hyper-spectral imaging. A configuration such as illustrated in the representative embodiment of FIG. 24 may be able to remove the effect of environmental fluctuations. Yet another technique may be to "wobble" the light beam after the light source using a vibrating mirror. The motion may lead to the beam moving enough to wash out spatial fluctuations within the beam waist at the sample or detection system. If the vibrating mirror is scanned faster than the integration time of the detectors, then the spatial fluctuations in the beam may be integrated out. Alternately, some sort of synchronous detection system may be used, where the detection is synchronized to the vibrating frequency.

Described herein are just some examples of the beneficial use of near-infrared or SWIR lasers for active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the active remote sensing or hyper-spectral imagery would also have a location tag on the data. Moreover, the active remote sensing or hyper-spectral imaging information could also be combined with two-dimensional or three-dimensional images to provide a physical picture as well as a chemical composition identification of the materials. These are just some modifications of the active remote sensing or hyper-spectral imaging system described in this disclosure, but other techniques may also be added or combinations of these techniques may be added, and these are also intended to be covered by this disclosure.

Wireless Link To The Cloud

The device may also benefit from communicating the data output to the "cloud" (e.g., data servers and processors in the web remotely connected) via wired and/or wireless communication strategies. The devices may be part of a series of biosensors applied to a patient, and collectively these devices form what might be called a body area network or a personal area network. The biosensors and non-invasive devices may communicate to a smart phone, tablet, personal data assistant, computer, and/or other microprocessor-based device, which may in turn wirelessly or over wire and/or fiber optically transmit some or all of the signal or processed data to the internet or cloud. The cloud or internet may in turn send the data to doctors or health care providers as well as the patients themselves. Thus, it may be possible to have a panoramic, high-definition, relatively comprehensive view of a patient that doctors can use to assess and manage disease, and that patients can use to help maintain their health and direct their own care.

In a particular embodiment 2500, device 2501 may be a non-invasive blood constituent measurement device comprising a transmitter 2503 to communicate over a first communication link 2504 in the body area network or personal area network to a receiver in a smart phone, tablet cell phone, PDA, or computer 2505. For 2501, it may also be advantageous to have a processor 2502 to process some of the physiological data, since with processing the amount of data to transmit may be less (hence, more energy efficient). The first communication link 2504 may operate through the use of one of many wireless technologies such as Bluetooth, Zigbee, WiFi, IrDA (infrared data association), wireless USB, or Z-wave, to name a few. Alternatively, the communication link 2504 may occur in the wireless medical band between 2360 and 2390 MHz, which the FCC allocated for medical body area network devices, or in other designated medical device or WMTS bands. These are examples of devices that can be used in the body area network and surroundings, but other devices could also be used and are included in the scope of this disclosure.

Personal device 2505 may store, process, display, and transmit some of the data from device 2501. The device 2505 may comprise a receiver, transmitter, display, voice control and speakers, and one or more control buttons or knobs and a touch screen. Examples of the device 2505 include smart phones such as the Apple iPhones® or phones operating on the Android or Microsoft systems. In one embodiment, the device 2505 may have an application, software program, or firmware to receive and process the data from the measurement device 2501. The device 2505 may then transmit some or all of the data or the processed data over a second communication link 2506 to the internet or "cloud" 2507. The second communication link 2506 may advantageously comprise at least one segment of a wireless transmission link, which may operate using WiFi or the cellular network. The second communication link 2506 may additionally comprise lengths of fiber optic and/or communication over copper wires or cables.

The internet or cloud 2507 may add value to device 2501 by providing services that augment the physiological data collected. In a particular embodiment, some of the functions performed by the cloud include: (a) receive at least a fraction of the data from the device 2505; (b) buffer or store the data received; (c) process the data using software stored on the cloud; (d) store the resulting processed data; and (e) transmit some or all of the data either upon request or based on an alarm. As an example, the data or processed data may be transmitted 2508 back to the originator (e.g., patient or user), it may be transmitted 2509 to a health care provider or doctor, or it may be transmitted 2510 to other designated recipients.

The cloud 2507 may provide a number of value-add services. For example, the cloud application may store and process the physiological data for future reference or during a visit with the healthcare provider. If a patient has some sort of medical mishap or emergency, the physician can obtain the history of the physiological parameters over a specified period of time. In another embodiment, if physiological parameters fall out of an acceptable range, alarms may be delivered to the user 2508, the healthcare provider 2509, or other designated recipients 2510. These are just some of the features that may be offered, but many others may be possible and are intended to be covered by this disclosure. As an example, the device 2505 may also have a GPS sensor, so the cloud 2507 may be able to provide time, data and position along with the physiological parameters. Thus, if there is a medical emergency, the cloud 2507 could provide the location of the patient to the healthcare provider 2509 or other designated recipients 2510. Moreover, the digitized data in the cloud 2507 may help to move toward what is often called "personalized medicine." Based on the physiological parameter data history, medication or medical therapies may be prescribed that are customized to the particular patient.

Beyond the above benefits, the cloud application 2507 and application on the device 2505 may also have financial value for companies developing devices 2501 such as a non-invasive blood constituent monitor. In the case of glucose monitors, the companies make the majority of their revenue on the measurement strips. However, with a noninvasive monitor, there is no need for strips, so there is less of an opportunity for recurring costs (e.g., the razor/razor blade model does not work for non-invasive devices). On the other hand, people may be willing to pay a periodic fee for the value-add services provided on the cloud 2507. Diabetic patients, for example, would probably be willing to pay a periodic fee for monitoring their glucose levels, storing the history of the glucose levels, and having alarm warnings when the glucose level falls out of range. Similarly, patients taking ketone bodies supplement for treatment of disorders characterized by impaired glucose metabolism (e.g., Alzheimer's, Parkinson's, Huntington's or ALS) may need to monitor their ketone bodies level. These patients would also probably be willing to pay a periodic fee for the value-add services provided on the cloud 2507. Thus, by leveraging the advances in wireless connectivity and the widespread use of handheld devices such as smart phones that can wirelessly connect to the cloud, businesses can build a recurring cost business model even using non-invasive measurement devices.

Although the present disclosure has been described in several embodiments, a myriad of changes, variations, alterations, transformations, and modifications may be suggested to one skilled in the art, and it is intended that the present disclosure encompass such changes, variations, alterations, transformations, and modifications as falling within the spirit and scope of the appended claims. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments described herein that are described as less desirable than other embodiments or prior art implementations with respect to one or more characteristics are not outside the scope of the disclosure and may be desirable for particular applications.

What is claimed is:

1. A diagnostic system comprising:
a light source configured to generate an output optical beam, comprising:
one or more semiconductor sources configured to generate an input beam;
one or more optical amplifiers configured to receive at least a portion of the input beam and to deliver an intermediate beam to an output end of the one or more optical amplifiers;
one or more optical fibers configured to receive at least a portion of the intermediate beam and to deliver at least the portion of the intermediate beam to a distal end of the one or more optical fibers to form a first optical beam;
a nonlinear element configured to receive at least a portion of the first optical beam and to broaden a spectrum associated with the at least a portion of the first optical beam to at least 10 nanometers through a nonlinear effect in the nonlinear element to form the output optical beam with an output beam broadened spectrum; and
wherein at least a portion of the output beam broadened spectrum comprises a near-infrared wavelength between 600 nanometers and 1000 nanometers;
and
an interface device configured to receive a received portion of the output optical beam and configured to deliver a delivered portion of the output optical beam to a tissue sample, wherein the interface device comprises a cap with one or more fiber leads configured to couple to at least one of the light source and a receiver, the receiver comprising one or more detectors;
wherein the receiver is configured to receive at least a portion of a diffuse spectroscopy output beam that results from light diffusion of the delivered portion of the output optical beam into a top two (2) millimeters or more of the tissue sample and configured to process the portion of the spectroscopy output beam to generate an output signal that monitors absorption or scattering features of the tissue sample;
wherein the tissue sample comprises at least in part brain tissue, and the output signal provides information related to oxy- and deoxy-hemoglobin, or related to metabolism.

2. The system of claim 1, wherein the light source is pulsed, and the receiver is further configured to perform time-gated detection and is configured to be synchronized with one or more pulses from the light source.

3. The system of claim 1, wherein the receiver is configured to:
generate a first signal responsive to light received while the light source is off; and
generate a second signal responsive to light received while the light source is on;
and wherein the diagnostic system is configured to improve a signal-to-noise ratio of the diffuse spectroscopy output beam by differencing the first signal and the second signal.

4. The system of claim 1, wherein the output optical beam is modulated at a modulation frequency, and wherein the receiver is configured to use a lock-in technique that detects at least one signal with a frequency around the modulation frequency.

5. The system of claim 1, wherein the interface device further comprises a monochromator configured to receive at least a portion of the received portion of the output optical beam and to form a filtered optical beam at least a portion of which forms the delivered portion of the output optical beam.

6. The system of claim 5, wherein the interface device is further configured to separate the filtered optical beam into a reference arm and a sample arm, wherein at least a portion of the sample arm forms the delivered portion of the output optical beam, and the reference arm is configured to be coupled to the receiver, and wherein the receiver is further configured to use the reference arm to at least partially cancel out effects from fluctuations in the light source.

7. The system of claim 5, wherein the monochromator is a dispersive spectrometer or a Fourier transform infrared (FTIR) spectrometer.

8. A diagnostic system comprising:
a light source configured to generate an output optical beam, comprising:
one or more semiconductor sources configured to generate an input beam;
one or more optical amplifiers configured to receive at least a portion of the input beam and to deliver an intermediate beam to an output end of the one or more optical amplifiers;
one or more optical fibers configured to receive at least a portion of the intermediate beam and to deliver at least the portion of the intermediate beam to a distal end of the one or more optical fibers to form a first optical beam;

a nonlinear element configured to receive at least a portion of the first optical beam and to broaden a spectrum associated with the at least a portion of the first optical beam to at least 10 nanometers through a nonlinear effect in the nonlinear element to form the output optical beam with an output beam broadened spectrum;

wherein at least a portion of the output beam broadened spectrum comprises a near-infrared wavelength between 600 nanometers and 1000 nanometers; and wherein the output optical beam is modulated at a modulation frequency;

an interface device configured to receive a received portion of the output optical beam and configured to deliver a delivered portion of the output optical beam to a tissue sample, wherein the interface device comprises a monochromator configured to receive at least a portion of the received portion of the output optical beam and to form a filtered optical beam as the delivered portion of the output optical beam; and a receiver configured to receive at least a portion of a diffuse spectroscopy output beam from the tissue sample that results from light diffusion of the delivered portion of the output optical beam into a top two (2) millimeters or more of the tissue sample, wherein the receiver is configured to process the portion of the spectroscopy output beam to generate an output signal that monitors absorption or scattering features of the tissue sample, wherein the receiver is configured to use a lock-in technique that detects at least one signal with a frequency around the modulation frequency.

9. The system of claim 8, wherein the light source is pulsed, and the receiver is further configured to perform time-gated detection, and to be synchronized with one or more pulses from the light source.

10. The system of claim 8, wherein the receiver is configured to:
generate a first signal in response to light received while the light source is off; and
generate a second signal in response to light received while the light source is on;
and wherein the diagnostic system is configured to improve a signal-to-noise ratio of the diffuse spectroscopy output beam by differencing the first signal and the second signal.

11. The system of claim 8, wherein the interface device is further configured to separate the filtered optical beam into a reference arm and a sample arm, wherein at least a portion of the sample arm forms the delivered portion of the output optical beam, and wherein the reference arm is configured to be coupled to the receiver, and wherein the receiver is further configured to use the reference arm to at least partially cancel out effects from fluctuations in the light source.

12. The system of claim 8, wherein the monochromator is a dispersive spectrometer or a Fourier transform infrared (FTIR) spectrometer.

13. The system of claim 8, wherein the interface device further comprises a cap with one or more fiber leads configured to couple to at least one of the light source and to the receiver wherein the receiver comprises one or more detectors, and wherein the tissue sample comprises at least in part brain tissue, and wherein the output signal provides information related to oxy- and deoxy-hemoglobin or related to metabolism.

14. A diagnostic system comprising:
a light source configured to generate an output optical beam, comprising:
one or more semiconductor sources configured to generate an input beam;
one or more optical amplifiers configured to receive at least a portion of the input beam and to deliver an intermediate beam to an output end of the one or more optical amplifiers;
one or more optical fibers configured to receive at least a portion of the intermediate beam and to deliver at least the portion of the intermediate beam to a distal end of the one or more optical fibers to form a first optical beam;
a nonlinear element configured to receive at least a portion of the first optical beam and to broaden a spectrum associated with the at least a portion of the first optical beam to at least 10 nanometers through a nonlinear effect in the nonlinear element to form the output optical beam with an output beam broadened spectrum;
wherein at least a portion of the output beam broadened spectrum comprises a near-infrared wavelength between 600 nanometers and 1000 nanometers; and
wherein the output optical beam is modulated at a modulation frequency;
an interface device configured to receive a received portion of the output optical beam and configured to deliver a delivered portion of the output optical beam to a tissue sample; and
a receiver configured to receive at least a portion of a diffuse spectroscopy output beam that results from light diffusion of the delivered portion of the output optical beam into a top two (2) millimeters or more of the tissue sample, and configured to process the portion of the spectroscopy output beam to generate an output signal that monitors absorption or scattering by the tissue sample, wherein the receiver is configured to use a lock-in technique that detects at least one signal with a frequency around the modulation frequency, and wherein the receiver is configured to:
generate a first signal in response to light received while the light source is off; and
generate a second signal in response to light received while the light source is on;
wherein the diagnostic system is configured to improve a signal-to-noise ratio of the diffuse spectroscopy output beam by differencing the first signal and the second signal.

15. The system of claim 14, wherein the light source is pulsed, and the receiver is further configured to perform time-gated detection and to be synchronized with one or more pulses from the light source.

16. The system of claim 14, wherein the interface device further comprises a monochromator configured to receive at least a portion of the received portion of the output optical beam and to form a filtered optical beam at least a portion of which forms the delivered portion of the output optical beam.

17. The system of claim 16, wherein the interface device is further configured to separate the filtered optical beam into a reference arm and a sample arm, wherein at least a portion of the sample arm forms the delivered portion of the output optical beam, and wherein the reference arm is configured to be coupled to the receiver, and wherein the receiver is further configured to use the reference arm to at least partially cancel out effects from fluctuations in the light source.

18. The system of claim 16, wherein the monochromator is a dispersive spectrometer or a Fourier transform infrared (FTIR) spectrometer.

19. The system of claim 14, wherein the interface device further comprises a cap with one or more fiber leads configured to couple to at least one of the light source and the receiver, wherein the receiver comprises one or more detectors.

20. The system of claim 14, wherein the tissue sample comprises at least in part brain tissue, and the output signal provides information related to oxy- and deoxy-hemoglobin, or related to metabolism.

* * * * *